United States Patent
Elenitoba-Johnson et al.

(10) Patent No.: US 9,284,594 B2
(45) Date of Patent: Mar. 15, 2016

(54) COMPOSITIONS AND METHODS RELATING TO FUSION PROTEIN BIOMARKERS

(71) Applicant: The Regents of the University of Michigan, Ann Arbor, MI (US)

(72) Inventors: Kojo Elenitoba-Johnson, Ann Arbor, MI (US); Delphine Rolland, Ann Arbor, MI (US); Venkatesha Basrur, Sylvania, OH (US); Kevin P. Conlon, Ann Arbor, MI (US); Megan S. Lim, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/317,606

(22) Filed: Jun. 27, 2014

(65) Prior Publication Data

US 2015/0031061 A1    Jan. 29, 2015

Related U.S. Application Data

(60) Provisional application No. 61/857,481, filed on Jul. 23, 2013.

(51) Int. Cl.
*C12Q 1/48* (2006.01)
*C12Q 1/37* (2006.01)
*G01N 33/68* (2006.01)

(52) U.S. Cl.
CPC .............. *C12Q 1/37* (2013.01); *G01N 33/6848* (2013.01); *G01N 2800/7028* (2013.01)

(58) Field of Classification Search
CPC ............. C12Q 1/37; G01N 2800/7028; G01N 33/6848
See application file for complete search history.

(56) References Cited

U.S. PATENT DOCUMENTS 6,174,674 B1 * 1/2001 Morris et al. ................ 435/6.11

OTHER PUBLICATIONS

Yang et al. A Multiple Reaction Monitoring (MRM) Method to Detect Bcr-Abl Kinase Activity in CML Using a Peptide Biosensor. PLOS ONE. Feb. 2013. vol. 8, No. 2, pp. 1-10.*
Liebler et al. Targeted Quantitation of Proteins by Mass Spectrometry. Biochemistry, Jun. 2014. Published online Mar. 21, 2013, pp. 3797-3806.*
Rowley, J.D., "Chromosome translocations: dangerous liaisons revisited," Nat Rev Cancer 1: 245-50, 2001.
Stratton, M.R., et al., The Cancer Genome, Nature 458: 719-24 (2009).
Mitelman, F., et al., "The impact of translocations and gene fusions on cancer causation," Nat Rev Cancer 7: 233-45 (2007).
Druker, B.J., et al.: Effects of a selective inhibitor of the Abl tyrosine kinase on the growth of Bcr-Abl positive cells, Nat Med 2: 561-6 (1996).
Druker B.J., et al.: "efficacy and safety of a specific inhibitor of the BCR-ABL tyrosine kinase in chronic myeloid leukemia," N Engl J Med 344: 1031-7 (2001).
Kwak, EL, et al.: "Anaplastic lymphoma kinase inhibition in non-small-cell lung cancer," N Engl J Med 363: 1693-703 (2010).
Carr, SA, et al., "Protein quantitation through targeted mass spectrometry: the way out of biomarker purgatory?" Clin Chem 54: 1749-52 (2008).
Domon, B., and Aebersold, R., "Mass spectrometry and protein analysis," Science 312: 212-7 (2006).
Yates, J.R., et al., "Proteomics by mass spectrometry: approaches, advances, and applications," Annu Rev Biomed Eng 11: 49-79 (2009).
Anderson, L. and Hunter, Cl: "Quantitative mass spectrometric multiple reaction monitoring assays for major plasma proteins," Mol Cell Proteomics 5: 573-88 (2006).
Keshishian, H., et al.: "Quantitative, multiplexed assays for low abundance proteins in plasma by targeted mass spectrometry and stable isotope dilution," Mol Cell Proteomics 6: 2212-29 (2007).
Wang, Q., et al., "Mutant proteins as cancer-specific biomarkers," Proc Natl Acad Sci USA 108: 2444-9 (2011).
Morris, SW, et al., "Fusion of a kinase gene, ALK, to a nucleolar protein gene, NPM, in non-Hodgkin's lymphoma," Science 263: 1281-4 (1994).
Kojo S.J. Elenitoba-Johnson, et al., "Proteomic identification of oncogenic chromosomal translocation partners encoding chimeric anaplastic lymphoma kinase fusion proteins," PNAS, vol. 103, No. 19, May 9, 2006, pp. 7402-07407.
Picotti, P and Aebersold R., "Selected reaction monitoring-based proteomics: workflows, potential, pitfalls and future directions," Nat Methods 9: 555-66 (2012).
Geoghegan, KF, et al., "Cyclization of N-terminal S-carbamoylmethylcysteine causing loss of 17 Da from peptides and extra peaks in peptide maps," J. Proteome Res 1: 181-7 (2002).
Keshishian H., et al., "Quantification of cardiovascular biomarkers in patient plasma by targeted mass spectrometry and stable isotope dilution," Mol Cell Proteomics, 8: 2339-49 (2009).
Kuzyk MA, et al., Multiple reaction monitoring-based, multiplexed, absolute quantitation of 45 proteins in human plasma Mol Cell Proteomics 8: 1860-77 (2009).

* cited by examiner

*Primary Examiner* — Marcela M Cordero Garcia
(74) *Attorney, Agent, or Firm* — Casimir Jones, SC

(57) ABSTRACT

The present invention provides fusion proteins as biomarkers specific for chromosomal translocation-based conditions (e.g., cancer), related methods for detecting fusion protein biomarkers associated with chromosomal translocation-based conditions, related methods for quantifying amount of fusion protein expression, and related methods for diagnosing chromosomal translocation-based conditions through detection of such fusion protein biomarkers. Such fusion protein biomarkers and related methods additionally find use in research settings.

5 Claims, 26 Drawing Sheets

A

| Cell lysate 2 μg/μL | Endogenous NPM-ALK fmole/μL | LOQ fmole/μL | LOD fmole/μL | %CV | Technical Replicate |
|---|---|---|---|---|---|
| NPM-ALK + | | | | | |
| SUD-HL-1 | 9.30 | 0.439 | 0.439 | 19 | 9 |
| Del | 4.99 | 0.879 | 0.439 | 15 | 9 |
| Karpas-299 | 3.40 | 1.76 | 0.439 | 15 | 9 |
| SUP-M2 | 8.68 | 0.879 | 0.439 | 19 | 8 |
| SR786 | 5.41 | 0.439 | 0.439 | 16 | 9 |
| | | | | | |
| NPM-ALK − | | | | | |
| HH | < LOD | 3.52 | 0.439 | NA | 9 |
| Mac-1 | < LOD | 3.52 | 0.879 | NA | 9 |
| Mac-2A | < LOD | 1.76 | 0.439 | NA | 9 |
| Jurkat | < LOD | 0.439 | 0.439 | NA | 9 |

NA = Not applicable
LOQ = Lowest heavy NPM-ALK standard observed with
S/N > 10 and % difference from theoretical ≤ 20%
LOD = Lowest heavy NPM-ALK standard observed with S/N > 10

B

Percentage of SUD-HL-1 in Mac-1

| Patient ID | Endogenous NPM-ALK fmole/µL | FP-MRM Interpretation (Blind) | LOQ fmole/µL | LOD fmole/µL | %CV | Technical Replicate |
|---|---|---|---|---|---|---|
| 1 | 3.08 | + | 0.879 | 0.439 | 13 | 9 |
| 2 | 5.88 | + | 0.879 | 0.439 | 11 | 9 |
| 3 | 5.79 | + | 0.439 | 0.439 | 8 | 9 |
| 4 | 2.56 | + | 1.76 | 0.879 | 28 | 9 |
| 5* | ND | - | - | - | NA | 3 |
| 6 | < LOD | - | 0.439 | 0.439 | NA | 9 |
| 7 | < LOD | - | 1.76 | 1.76 | NA | 9 |
| 8 | < LOD | - | 0.879 | 0.879 | NA | 9 |
| 9* | ND | - | - | - | NA | 3 |
| 10* | ND | - | - | - | NA | 3 |
| 11* | ND | - | - | - | NA | 3 |
| 12* | ND | - | - | - | NA | 3 |
| 13 | < LOD | - | 0.439 | 0.439 | NA | 9 |
| 14 | < LOD | - | 0.879 | 0.879 | NA | 9 |
| 15 | < LOD | - | 0.879 | 0.439 | NA | 8 |
| 16 | < LOD | - | 3.52 | 0.439 | NA | 9 |
| 17 | 5.92 | + | 1.76 | 0.439 | 9 | 9 |
| 18 | 7.1 | + | 0.879 | 0.439 | 13 | 9 |
| 19 | 2.86 | + | 0.879 | 0.439 | 18 | 9 |
| 20 | 4.62 | + | 0.879 | 0.439 | 14 | 9 |
| 21 | 3.01 | + | 0.879 | 0.439 | 22 | 9 |
| 22 | 13.7 | + | 1.76 | 1.76 | 11 | 9 |
| 23 | 12.2 | + | 1.76 | 0.879 | 18 | 9 |

* = Patients evaluated using 50 fmole/µl heavy & double heavy NPM-ALK
ND = Not detected
NA = Not applicable
LOQ = Lowest heavy NPM-ALK standard observed with S/N > 10
       and % difference from theoretical ≤ 20%
LOD = Lowest heavy NPM-ALK standard observed with S/N > 10

SEQUENCE LISTING

```
<160> NUMBER OF SEQ ID NOS: 35

<210> SEQ ID NO 1
<211> LENGTH: 17
<212> TYPE: PRT
<213> ORGANISM: Artificial sequence
<220> FEATURE:
<223> OTHER INFORMATION: Synthetic

<400> SEQUENCE: 1

Cys Gly Ser Gly Pro Val His Ile Ser Gly Gln His Leu Val Val Tyr
1               5                   10                  15

Arg

<210> SEQ ID NO 2
<211> LENGTH: 8
<212> TYPE: PRT
<213> ORGANISM: Artificial sequence
<220> FEATURE:
<223> OTHER INFORMATION: Synthetic

<400> SEQUENCE: 2

Thr Ile Asn Lys Glu Glu Ala Leu
1               5

<210> SEQ ID NO 3
<211> LENGTH: 7
<212> TYPE: PRT
<213> ORGANISM: Artificial sequence
<220> FEATURE:
<223> OTHER INFORMATION: Synthetic

<400> SEQUENCE: 3

His Gly Asp Ala Glu Ala Leu
1               5

<210> SEQ ID NO 4
<211> LENGTH: 9
<212> TYPE: PRT
<213> ORGANISM: Artificial sequence
<220> FEATURE:
<223> OTHER INFORMATION: Synthetic

<400> SEQUENCE: 4

Ser Arg Ser Val Asp Gly Val Ser Glu
1               5

<210> SEQ ID NO 5
<211> LENGTH: 12
<212> TYPE: PRT
<213> ORGANISM: Artificial sequence
<220> FEATURE:
<223> OTHER INFORMATION: Synthetic
```

```
<400> SEQUENCE: 5

Glu Ser Arg Ser Val Asp Gly Val Ser Glu Ser Lys
1               5                   10

<210> SEQ ID NO 6
<211> LENGTH: 14
<212> TYPE: PRT
<213> ORGANISM: Artificial sequence
<220> FEATURE:
<223> OTHER INFORMATION: Synthetic

<400> SEQUENCE: 6

Glu Ser Asn Glu Leu Asn Asn Leu Gly His Pro Asp Asn Lys
1               5                   10

<210> SEQ ID NO 7
<211> LENGTH: 9
<212> TYPE: PRT
<213> ORGANISM: Artificial sequence
<220> FEATURE:
<223> OTHER INFORMATION: Synthetic

<400> SEQUENCE: 7

Thr Ile Asp Asp Leu Glu Val Tyr Arg
1               5

<210> SEQ ID NO 8
<211> LENGTH: 16
<212> TYPE: PRT
<213> ORGANISM: Artificial sequence
<220> FEATURE:
<223> OTHER INFORMATION: Synthetic

<400> SEQUENCE: 8

Asn Val Gly Glu Ser Val Ala Ala Ala Leu Ser Pro Leu Val Tyr Arg
1               5                   10                  15

<210> SEQ ID NO 9
<211> LENGTH: 8
<212> TYPE: PRT
<213> ORGANISM: Artificial sequence
<220> FEATURE:
<223> OTHER INFORMATION: Synthetic

<400> SEQUENCE: 9

Phe Lys Gln Thr Tyr Ser Asn Glu
1               5

<210> SEQ ID NO 10
<211> LENGTH: 15
<212> TYPE: PRT
<213> ORGANISM: Artificial sequence
<220> FEATURE:
<223> OTHER INFORMATION: Synthetic

<400> SEQUENCE: 10

Ser Asp Phe Val Tyr Cys Gln Val Cys Cys Glu Pro Phe His Lys
1               5                   10                  15

<210> SEQ ID NO 11
<211> LENGTH: 15
<212> TYPE: PRT
<213> ORGANISM: Artificial sequence
<220> FEATURE:
<223> OTHER INFORMATION: Synthetic
```

<400> SEQUENCE: 11

Ile Thr Val Asp Gly Pro Arg Glu Pro Arg Asn Arg Thr Glu Lys
1               5                   10                  15

<210> SEQ ID NO 12
<211> LENGTH: 12
<212> TYPE: PRT
<213> ORGANISM: Artificial sequence
<220> FEATURE:
<223> OTHER INFORMATION: Synthetic

<400> SEQUENCE: 12

Gly Ala Pro Gln Ala Pro Val Gly Asp Val Ala Leu
1               5                   10

<210> SEQ ID NO 13
<211> LENGTH: 10
<212> TYPE: PRT
<213> ORGANISM: Artificial sequence
<220> FEATURE:
<223> OTHER INFORMATION: Synthetic

<400> SEQUENCE: 13

Val Asp Phe Lys Asp Ser Val Ser Leu Arg
1               5                   10

<210> SEQ ID NO 14
<211> LENGTH: 12
<212> TYPE: PRT
<213> ORGANISM: Artificial sequence
<220> FEATURE:
<223> OTHER INFORMATION: Synthetic

<400> SEQUENCE: 14

Leu Ser Ser Cys Ile Thr Gln Gly Lys Ala Ile Glu
1               5                   10

<210> SEQ ID NO 15
<211> LENGTH: 16
<212> TYPE: PRT
<213> ORGANISM: Artificial sequence
<220> FEATURE:
<223> OTHER INFORMATION: Synthetic

<400> SEQUENCE: 15

Pro Thr Pro Gly Lys Gly Pro Lys Val Tyr Arg Arg Lys His Gln Glu
1               5                   10                  15

<210> SEQ ID NO 16
<211> LENGTH: 16
<212> TYPE: PRT
<213> ORGANISM: Artificial sequence
<220> FEATURE:
<223> OTHER INFORMATION: Synthetic

<400> SEQUENCE: 16

Tyr Ile Met Ser Asn Ser Gly Asp Tyr Glu Ile Leu Tyr Leu Tyr Arg
1               5                   10                  15

<210> SEQ ID NO 17
<211> LENGTH: 12
<212> TYPE: PRT
<213> ORGANISM: Artificial sequence
<220> FEATURE:
<223> OTHER INFORMATION: Synthetic

```
<400> SEQUENCE: 17

Lys Asn Ser Gln Val Tyr Arg Arg Lys His Gln Glu
1               5                   10

<210> SEQ ID NO 18
<211> LENGTH: 7
<212> TYPE: PRT
<213> ORGANISM: Artificial sequence
<220> FEATURE:
<223> OTHER INFORMATION: Synthetic

<400> SEQUENCE: 18

Ser Glu Gln Asp Leu Ile Arg
1               5

<210> SEQ ID NO 19
<211> LENGTH: 9
<212> TYPE: PRT
<213> ORGANISM: Artificial sequence
<220> FEATURE:
<223> OTHER INFORMATION: Synthetic

<400> SEQUENCE: 19

Gln Ile Met Pro Lys Lys Pro Ala Glu
1               5

<210> SEQ ID NO 20
<211> LENGTH: 10
<212> TYPE: PRT
<213> ORGANISM: Artificial sequence
<220> FEATURE:
<223> OTHER INFORMATION: Synthetic

<400> SEQUENCE: 20

Gly Gln Gln Ser Ser Gly Gln Ile Gln Leu
1               5                   10

<210> SEQ ID NO 21
<211> LENGTH: 10
<212> TYPE: PRT
<213> ORGANISM: Artificial sequence
<220> FEATURE:
<223> OTHER INFORMATION: Synthetic

<400> SEQUENCE: 21

Ser Pro Gln Asn Ser Ile Arg His Asn Leu
1               5                   10

<210> SEQ ID NO 22
<211> LENGTH: 8
<212> TYPE: PRT
<213> ORGANISM: Artificial sequence
<220> FEATURE:
<223> OTHER INFORMATION: Synthetic

<400> SEQUENCE: 22

Gly Gln Gln Ser Glu Lys Pro Tyr
1               5

<210> SEQ ID NO 23
<211> LENGTH: 16
<212> TYPE: PRT
<213> ORGANISM: Artificial sequence
<220> FEATURE:
<223> OTHER INFORMATION: Synthetic
```

<400> SEQUENCE: 23

Gly Gly Met Gly Lys Ile Leu Lys Asp Leu Ser Ser Glu Asp Thr Arg
1               5                   10                  15

<210> SEQ ID NO 24
<211> LENGTH: 12
<212> TYPE: PRT
<213> ORGANISM: Artificial sequence
<220> FEATURE:
<223> OTHER INFORMATION: Synthetic

<400> SEQUENCE: 24

Gly Gln Gln Ile Ala Ile Ala Pro Asn Gly Ala Leu
1               5                   10

<210> SEQ ID NO 25
<211> LENGTH: 15
<212> TYPE: PRT
<213> ORGANISM: Artificial sequence
<220> FEATURE:
<223> OTHER INFORMATION: Synthetic

<400> SEQUENCE: 25

Gln Gly Pro Ser Gly Ala Ser Gly Pro Ala Gly Pro Arg Gly Asp
1               5                   10                  15

<210> SEQ ID NO 26
<211> LENGTH: 15
<212> TYPE: PRT
<213> ORGANISM: Artificial sequence
<220> FEATURE:
<223> OTHER INFORMATION: Synthetic

<400> SEQUENCE: 26

Leu Pro Gly His Val Ala Ala Asp His Pro Pro Ala Val Tyr Arg
1               5                   10                  15

<210> SEQ ID NO 27
<211> LENGTH: 27
<212> TYPE: DNA
<213> ORGANISM: Artificial sequence
<220> FEATURE:
<223> OTHER INFORMATION: Synthetic

<400> SEQUENCE: 27
cagtgcatat tagtggacag cacttag                                            27

<210> SEQ ID NO 28
<211> LENGTH: 18
<212> TYPE: DNA
<213> ORGANISM: Artificial sequence
<220> FEATURE:
<223> OTHER INFORMATION: Synthetic

<400> SEQUENCE: 28
tgatggtcga ggtgcgga                                                      18

<210> SEQ ID NO 29
<211> LENGTH: 23
<212> TYPE: DNA
<213> ORGANISM: Artificial sequence
<220> FEATURE:
<223> OTHER INFORMATION: Synthetic

<400> SEQUENCE: 29
caccaggagc tgcaagccat gca                                                23

```
<210> SEQ ID NO 30
<211> LENGTH: 21
<212> TYPE: DNA
<213> ORGANISM: Artificial sequence
<220> FEATURE:
<223> OTHER INFORMATION: Synthetic

<400> SEQUENCE: 30
caacactgct tctgatggca a                                              21

<210> SEQ ID NO 31
<211> LENGTH: 20
<212> TYPE: DNA
<213> ORGANISM: Artificial sequence
<220> FEATURE:
<223> OTHER INFORMATION: Synthetic

<400> SEQUENCE: 31
ctggataatg gagcgtggtg                                                20

<210> SEQ ID NO 32
<211> LENGTH: 25
<212> TYPE: DNA
<213> ORGANISM: Artificial sequence
<220> FEATURE:
<223> OTHER INFORMATION: Synthetic

<400> SEQUENCE: 32
caacaccctg gccgagttgg ttcat                                          25

<210> SEQ ID NO 33
<211> LENGTH: 16
<212> TYPE: PRT
<213> ORGANISM: Artificial sequence
<220> FEATURE:
<223> OTHER INFORMATION: Synthetic

<400> SEQUENCE: 33

Gly Ser Gly Pro Val His Ile Ser Gly Gln His Leu Val Val Tyr Arg
1               5                   10                  15

<210> SEQ ID NO 34
<211> LENGTH: 13
<212> TYPE: PRT
<213> ORGANISM: Artificial sequence
<220> FEATURE:
<223> OTHER INFORMATION: Synthetic

<400> SEQUENCE: 34

Gly Ser Gly Pro Val His Ile Ser Gly Gln His Leu Val
1               5                   10

<210> SEQ ID NO 35
<211> LENGTH: 19
<212> TYPE: PRT
<213> ORGANISM: Artificial sequence
<220> FEATURE:
<223> OTHER INFORMATION: Synthetic

<400> SEQUENCE: 35

Lys Cys Gly Ser Gly Pro Val His Ile Ser Gly Gln His Leu Val Val
1               5                   10                  15

Tyr Arg Arg
```

US 9,284,594 B2

COMPOSITIONS AND METHODS RELATING TO FUSION PROTEIN BIOMARKERS

CROSS-REFERENCE TO RELATED APPLICATIONS

This application claims priority to U.S. Provisional Patent Application No. 61/857,481, filed Jul. 23, 2013, the contents of which are incorporated by reference in its entirety.

STATEMENT REGARDING FEDERALLY SPONSORED RESEARCH OR DEVELOPMENT

This application was made with government support under DE019249, CA140806 and CA136905 awarded by the National Institutes of Health. The government has certain rights in the invention.

FIELD OF THE INVENTION

The present invention provides fusion proteins as biomarkers specific for chromosomal translocation-based conditions (e.g., cancer), related methods for detecting fusion protein biomarkers associated with chromosomal translocation-based conditions, related methods for quantifying amount of fusion protein expression, and related methods for diagnosing chromosomal translocation-based conditions through detection of such fusion protein biomarkers. Such fusion protein biomarkers and related methods additionally find use in research settings.

BACKGROUND OF THE INVENTION

Cancer affects millions of people worldwide. Mortality is substantially due to diagnosis at stages that are too late for therapies to be effective. Advances in screening methods have improved the early diagnosis, prognosis, and survival for some cancers. Several validated biomarkers are currently used to diagnose and monitor the progression of cancer, but none of them shows adequate specificity, sensitivity, and predictive value for population screening. Accordingly, there is an urgent need to isolate novel sensitive, specific biomarkers to detect the disease early and improve prognosis.

SUMMARY

Chromosomal translocations encoding chimeric fusion proteins constitute one of the most common mechanisms underlying oncogenic transformation in human cancer. Fusion peptides resulting from such oncogenic chimeric fusions though unique to specific cancer subtypes are unexplored as cancer biomarkers. Experiments conducted during the course of developing embodiments for the present invention innovated an approach termed fusion peptide multiple reaction monitoring (FP-MRM) mass spectrometry (MS), the direct identification of different cancer-specific fusion peptides arising from protein chimeras that are generated from juxtaposition of heterologous genes fused by recurrent chromosomal translocations. Using FP-MRM-MS in a clinically relevant scenario, specific, sensitive and unambiguous detection of a specific diagnostic fusion peptide in clinical samples of anaplastic large cell lymphoma (ALCL) was demonstrated, but not in a diverse array of benign lymph nodes or other forms of primary malignant lymphomas and cancer-derived cell lines. Such experiments highlight the utility of fusion peptides as cancer biomarkers and carry broad implications for the use of protein biomarkers in cancer detection and monitoring.

As described in Examples I-V, experiments conducted during the course of developing embodiments for the present invention demonstrate utilization of MRM-MS for the detection of fusion chimeras resulting from recurrent chromosomal translocations characteristic of specific forms of cancer. In particular, five unique fusion peptides from 5 distinct chimeric fusion proteins that are characteristic of 3 different types of cancer (NPM-ALK in ALCL, API2-MALT1 in MALT lymphoma and BCR-ABL in CML) were detected. Using FP-MRM-MS detailed analysis of the specific NPM-ALK fusion encoded by t(2;5)(p23;q35) was performed for the detection of ALCL in a clinically relevant context. Using this approach, NPM-ALK positive and negative cell lines and a large cohort of clinical samples including those carrying the NPM-ALK fusion (FIGS. 6 and 8) were correctly identified. NPM-ALK fusion peptide MRM results show excellent qualitative correlation with orthogonal assays such as western blotting and quantitative real-time polymerase chain reaction (FIGS. 6, 7, 8). Delusional studies revealed that fusion peptide MRM exhibited sensitivity comparable to western blotting and quantitative real-time polymerase chain reaction, approximating 250 fmole/mg of tumor protein (FIG. 7). Using cellular dilution studies, the ability to detect NPM-ALK fusion peptides when the NPM-ALK positive lymphoma cells comprise only 5% of the cellular composition of the interrogated protein extract (FIG. 7) was demonstrated. Indeed, such a level of sensitivity is well-suited for the detection of tumor cells in clinical biopsy specimens with >5% tumor involvement. Moreover, fusion peptide MRM using actual clinical samples of anaplastic large cell lymphoma carrying the t(2;5)(p23;q35) aberration and expressing the NPM-ALK chimeric protein yielded 100% specificity with no false positives or negatives (FIG. 8).

Indeed, the implementation of accurate protein biomarkers in clinically useful scenarios has been challenging because many biomarker candidates are expressed in non-disease states and thus the establishment of universal quantitative threshold levels for unequivocal diagnosis of disease is difficult. In this regard, chimeric fusion proteins arising from chromosomal translocations are ideal biomarkers because of their qualitative nature and pathognomonic specificity in several forms of cancer. Overall, the methods of the present invention are fairly simple to implement and scalable for analysis of multiple samples and specimen types.

Accordingly, the present invention provides fusion proteins as biomarkers specific for chromosomal translocation-based conditions (e.g., cancer), related methods for detecting fusion protein biomarkers associated with chromosomal translocation-based conditions, related methods for quantifying amount of fusion protein expression, and related methods for diagnosing chromosomal translocation-based conditions through detection of such fusion protein biomarkers. Such fusion protein biomarkers and related methods additionally find use in research settings.

In certain embodiments, the present invention provides methods for detecting the presence of a fusion protein within a biological sample (e.g., blood sample, tissue sample, etc.) (e.g., a biological sample from a human subject) (e.g., a biological sample from a human subject suspected of having a chromosomal translocation-based condition). In some embodiments, such methods involve providing a biological sample and labeled peptides having an amino acid sequence that spans the fusion junction of a fusion protein encoded by a fusion of a first nucleic acid (e.g., gene) to a second nucleic acid (e.g., gene). In some embodiments, the labeled peptides comprise peptides having one isotopically labeled amino acid residue and peptides having two isotopically labeled amino acid residues. In some embodiments, the amino acid sequence of the labeled peptides is identical with an amino acid sequence of a fusion protein peptide fragment generated through digestion of the fusion protein with a protease, wherein the protease is known to generate upon digestion of the fusion protein a fusion protein peptide fragment having an amino acid sequence identical with the labeled peptides. The methods are not limited to use of a particular protease. In some embodiments, the protease is selected from the group consisting of trypsin, chymotrypsin, V8-DE, Lys-C, and Arg-C. In some embodiments, the fusion protein encoded by a fusion of a first nucleic acid to a second nucleic acid is the result of a chromosomal translocation.

In some embodiments, the methods further comprise digesting the biological sample with the protease resulting in generation of biological sample-based peptide fragments.

In some embodiments, the methods further comprise combining the labeled peptides with the generated biological sample-based peptide fragments.

In some embodiments, the methods further comprise purifying the labeled peptides combined with the generated biological sample-based peptide fragments.

In some embodiments, the methods further comprise conducting a multiple reaction monitoring mass-spectrometry (MRM-MS) analysis of the purified biological sample-based peptide fragments combined with the labeled peptides. In some embodiments, the MRM-MS is conducted with a triple quadrupole mass spectrometer. In some embodiments, the MRM-MS analysis comprises an ionization technique such as, for example, photoioinization, electrospray ionization, atmospheric pressure chemical ionization, and electron capture ionization. In some embodiments, the ionization is performed in positive or negative mode.

In some embodiments, the methods further comprise analyzing the results of the MRM-MS analysis, wherein the analyzing comprises detecting the presence or absence of a biological sample-based fusion protein peptide fragment having an amino acid sequence identical with the labeled peptides, wherein detected co-elution of i) a biological sample-based fusion protein peptide fragment having an amino acid sequence identical with the labeled peptides, and ii) the labeled peptides, indicates the presence of the fusion protein within the biological sample. In some embodiments, the analyzing further comprises quantifying the amount of expression of said fusion protein within said biological sample. In some embodiments, the quantified amount of expression of the fusion protein is compared with a quantified amount of expression of the fusion protein measured at an earlier time point (e.g., for purposes of assessing the efficacy of a particular treatment and/or therapy). The methods of the present invention permit a high sensitivity for detecting and quantifying fusion protein expression at sub-femtomole levels (e.g., attomole levels; zeptomole levels; yoctomole levels) per mg lysate. For example, in some embodiments, such detection and/or quantitation methods permit a high sensitivity detection of fusion proteins at levels as low as, for example, 0.4 fmole μL (222 fmoles/mg lysate).

In some embodiments, the fusion protein, protease and amino acid sequence of the labeled peptides is one or more of NPM-ALK, trypsin, CGSGPVHISGQHLVVYR (SEQ ID NO: 1); BCR-ABL1 (E13a2), chymotrypsin, TINKEEAL (SEQ ID NO: 2); BCR-ABL1 (E1a2), chymotrypsin, HGDAEAL (SEQ ID NO: 3); API2-MALT1 (ex7-ex5), V8-DE, SRSVDGVSE (SEQ ID NO: 4); API2-MALT1 (ex7-ex8), Lys-C, ESRSVDGVSESK (SEQ ID NO: 5); TPM3-ALK, trypsin, ESNELNNLGHPDNK (SEQ ID NO: 6); CLTC-ALK, trypsin, TIDDLEVYR (SEQ ID NO: 7); SQSTM1-ALK, trypsin, NVGESVAAALSPLVYR (SEQ ID NO: 8); MLL-AF4, V8-DE, FKQTYSNE (SEQ ID NO: 9); MLL-AF9, trypsin, SDFVYCQVCCEPFHK (SEQ ID NO: 10); AML1-MTG8, Lys-C, ITVDGPREPRNRTEK (SEQ ID NO: 11); NUP98-HOXD13, chymotrypsin, GAPQAPVGD-VAL (SEQ ID NO: 12); MLL-ELL, Arg-C, VDFKDSVSLR (SEQ ID NO: 13); PML-RARA, V8-DE, LSSCITQGKAIE (SEQ ID NO: 14); EML4-ALK (variant 1), V8-DE, PTPGKGPKVYRRKHQE (SEQ ID NO: 15); EML4-ALK (variant 2), trypsin, YIMSNSGDYEILYLYR (SEQ ID NO: 16); EML4-ALK (variant 3a), V8-DE, KNSQVYRRKHQE (SEQ ID NO: 17); AKAP9-BRAF, trypsin, SEQDLIR (SEQ ID NO: 18); SYT-SSX1, V8-DE, QIMPKKPAE (SEQ ID NO: 19); SYT-SSX2, V8-DE, QIMPKKPAE (SEQ ID NO: 19); EWSR1-ERG, chymotrypsin, GQQSSGQIQL (SEQ ID NO: 20); PAX3-FOXO1, chymotrypsin, SPQNSIRHNL (SEQ ID NO: 21); EWS/WT1, chymotrypsin, GQQSEKPY (SEQ ID NO: 22); EWSR1/ATF1 (fusion type 1), Arg-C, GGMGKILKDLSSEDTR (SEQ ID NO: 23); EWSR1/ATF1 (fusion type 2), chymotrypsin, GQQIAIAPNGAL (SEQ ID NO: 24); and COL1A1-PDGFB, V8-DE, GPSGASGPAG-PRGD (SEQ ID NO: 25).

In some embodiments, the detected presence of NPM-ALK fusion protein corresponds with a t(2;5)(p23;q35) cytogenetic abnormality; BCR-ABL1 (E13a2) fusion protein corresponds with a (9;22)(q34;q11.2) cytogenetic abnormality; BCR-ABL1 (E1a2) fusion protein corresponds with a t(9;22)(q34;q11.2) cytogenetic abnormality; API2-MALT1 (ex7-ex5) fusion protein corresponds with a t(11;18)(q21;q21) cytogenetic abnormality; API2-MALT1 (ex7-ex8) fusion protein corresponds with a t(11;18)(q21;q21) cytogenetic abnormality; TPM3-ALK fusion protein corresponds with a t(1;2)(q25;p23) cytogenetic abnormality; CLTC-ALK fusion protein corresponds with a t(2;17)(p23;q23) cytogenetic abnormality; SQSTM1-ALK fusion protein corresponds with a t(2;5)(p23;q35) cytogenetic abnormality; MLL-AF4 fusion protein corresponds with a t(4;11)(q21;23) cytogenetic abnormality; MLL-AF9 fusion protein corresponds with a t(9;11)(p22;q23) cytogenetic abnormality; AML1-MTG8 fusion protein corresponds with a t(8;21)(q22;q22) cytogenetic abnormality; NUP98-HOXD13 fusion protein corresponds with a t(2;11)(q31;p15) cytogenetic abnormality; MLL-ELL fusion protein corresponds with a t(11;19)(q23;p13.3) cytogenetic abnormality; PML-RARA fusion protein corresponds with a t(15;17)(q22;q21) cytogenetic abnormality; EML4-ALK (variant 1, 2 or 3a) fusion protein corresponds with a inv(2)(p21;p23) cytogenetic abnormality; AKAP9-BRAF fusion protein corresponds with a inv(7)(q21;q34) cytogenetic abnormality; SYT-SSX1 or SYT-SSX2 fusion protein corresponds with a t(X;18)(p11.2;q11.2) cytogenetic abnormality; EWSR1-ERG fusion protein corresponds with a t(21;22)(q21;q12) cytogenetic abnormality; PAX3-FOXO1 fusion protein corresponds with a t(2;13)(q35;q14) cytogenetic abnormality; EWS/WT1 fusion protein corresponds with a t(11;22)(p13;q12) cytogenetic abnormality; EWSR1/ATF1 (fusion type 1 or 2) fusion protein corresponds with a t(12;22)(a13;q12) cytogenetic abnormality; and COL1A1-PDGFB fusion protein corresponds with a t(17;22)(q22;q13) cytogenetic abnormality.

In certain embodiments, the present invention provides methods for detecting the presence of two or more fusion proteins within a biological sample. For example, in some embodiments, separate biological samples digested with different proteases are combined prior to MRM-MS analysis.

In certain embodiments, the present invention provides methods for detecting the presence of a chromosomal translocation-based condition within a subject, comprising providing a biological sample from a subject (e.g., a human subject) (e.g., a human subject suspected of having a chromosomal translocation-based condition) (e.g., blood sample, tissue sample, etc.) and labeled peptides having an amino acid sequence that spans the fusion junction of a fusion protein encoded by a fusion of a first nucleic acid (e.g., gene) to a second nucleic acid (e.g., gene). In some embodiments, the labeled peptides comprise peptides having one isotopically labeled amino acid residue and peptides having two isotopically labeled amino acid residues. In some embodiments, the amino acid sequence of the labeled peptides is identical with an amino acid sequence of a fusion protein peptide fragment generated through digestion of the fusion protein with a protease, wherein the protease is known to generate upon digestion of the fusion protein a fusion protein peptide fragment having an amino acid sequence identical with the labeled peptides. The methods are not limited to use of a particular protease. In some embodiments, the protease is selected from the group consisting of trypsin, chymotrypsin, V8-DE, Lys-C, and Arg-C. In some embodiments, the fusion protein encoded by a fusion of a first nucleic acid to a second nucleic acid is the result of a chromosomal translocation.

In some embodiments, the methods further comprise digesting the biological sample with the protease resulting in generation of biological sample-based peptide fragments.

In some embodiments, the methods further comprise combining the labeled peptides with the generated biological sample-based peptide fragments.

In some embodiments, the methods further comprise purifying the labeled peptides combined with the generated biological sample-based peptide fragments.

In some embodiments, the methods further comprise conducting a multiple reaction monitoring mass-spectrometry (MRM-MS) analysis of the purified biological sample-based peptide fragments combined with the labeled peptides. In some embodiments, the MRM-MS is conducted with a triple quadrupole mass spectrometer. In some embodiments, the MRM-MS analysis comprises an ionization technique such as, for example, photoioinization, electrospray ionization, atmospheric pressure chemical ionization, and electron capture ionization. In some embodiments, the ionization is performed in positive or negative mode.

In some embodiments, the methods further comprise analyzing the results of the MRM-MS analysis, wherein the analyzing comprises detecting the presence or absence of a biological sample-based fusion protein peptide fragment having an amino acid sequence identical with the labeled peptides, wherein detected co-elution of i) a biological sample-based fusion protein peptide fragment having an amino acid sequence identical with the labeled peptides, and ii) the labeled peptides, indicates the presence of the fusion protein within the biological sample, wherein a detected presence of the fusion protein within the biological sample indicates the presence of the chromosomal translocation-based condition within the subject. In some embodiments, the analyzing further comprises quantifying the amount of expression of said fusion protein within said biological sample. In some embodiments, the quantified amount of expression of the fusion protein is compared with a quantified amount of expression of the fusion protein measured at an earlier time point (e.g., for purposes of assessing the efficacy of a particular treatment and/or therapy). The methods of the present invention permit a high sensitivity for detecting and quantifying fusion protein expression at sub-femtomole levels (e.g., attomole levels; zeptomole levels; yoctomole levels) per mg lysate. For example, in some embodiments, such detection and/or quantitation methods permit a high sensitivity detection of fusion proteins at levels as low as, for example, 0.4 fmole μL (222 fmoles/mg lysate).

In some embodiments, the chromosomal translocation-based condition, fusion protein, protease and amino acid sequence of the labeled peptides is selected from ALK-positive anaplastic large cell lymphoma, NPM-ALK, trypsin, CGSGPVHISGQHLVVYR (SEQ ID NO: 1); chronic myeloid leukemia or B-cell acute lymphoblastic leukemia, BCR-ABL1 (E13a2), chymotrypsin, TINKEEAL (SEQ ID NO: 2); chronic myeloid leukemia or B-cell acute lymphoblastic leukemia, BCR-ABL1 (E1a2), chymotrypsin, HGDAEAL (SEQ ID NO: 3); mucosa associated lymphoid tissue lymphoma, API2-MALT1 (ex7-ex5), V8-DE, SRS-VDGVSE (SEQ ID NO: 4); mucosa associated lymphoid tissue lymphoma; API2-MALT1 (ex7-ex8), Lys-C, ESRS-VDGVSESK (SEQ ID NO: 5); ALK-positive anaplastic large cell lymphoma, TPM3-ALK, trypsin, ESNELNNLGHP-DNK (SEQ ID NO: 6); ALK-positive diffuse large B-cell lymphoma or ALCL, CLTC-ALK, trypsin, TIDDLEVYR (SEQ ID NO: 7); ALK-positive diffuse large B-cell lymphoma, SQSTM1-ALK, trypsin, NVGESVAAALSPLVYR (SEQ ID NO: 8); biphenotypic acute lymphoblastic leukemia or B-cell acute lymphoblastic leukemia, MLL-AF4, V8-DE, FKQTYSNE (SEQ ID NO: 9); acute myeloid leukemia, MLL-AF9, trypsin, SDFVYCQVCCEPFHK (SEQ ID NO: 10); acute myeloid leukemia, AML1-MTG8, Lys-C, ITVDG-PREPRNRTEK (SEQ ID NO: 11); acute myeloid leukemia, NUP98-HOXD13, chymotrypsin, GAPQAPVGDVAL (SEQ ID NO: 12); acute myeloid leukemia, MLL-ELL, Arg-C, VDFKDSVSLR (SEQ ID NO: 13); acute promyelocytic leukemia, PML-RARA, V8-DE, LSSCITQGKAIE (SEQ ID NO: 14); non-small cell lung cancer, EML4-ALK (variant 1), V8-DE, PTPGKGPKVYRRKHQE (SEQ ID NO: 15); non-small cell lung cancer, EML4-ALK (variant 2), trypsin, YIM-SNSGDYEILYLYR (SEQ ID NO: 16); non-small cell lung cancer, EML4-ALK (variant 3a), V8-DE, KNSQVYR-RKHQE (SEQ ID NO: 17); papillary thyroid carcinoma, AKAP9-BRAF, trypsin, SEQDLIR; synovial sarcoma, SYT-SSX1, V8-DE, QIMPKKPAE (SEQ ID NO: 19); synovial sarcoma, SYT-SSX2, V8-DE, QIMPKKPAE (SEQ ID NO: 19); Ewing sarcoma, EWSR1-ERG, chymotrypsin, GQQSS-GQIQL (SEQ ID NO: 20); alveolar rhabdomyosarcoma, PAX3-FOXO1, chymotrypsin, SPQNSIRHNL (SEQ ID NO: 21); desmoplastic small round cell tumor, EWS/WT1, chymotrypsin, GQQSEKPY (SEQ ID NO: 22); clear cell sarcoma, EWSR1/ATF1 (fusion type 1), Arg-C, GGMGKILKDLSSEDTR (SEQ ID NO: 23); clear cell sarcoma, EWSR1/ATF1 (fusion type 2), chymotrypsin, GQQIAIAPNGAL (SEQ ID NO: 24); and dermatofibrosarcoma protuberans, COL1A1-PDGFB, V8-DE, QGPSGAS-GPAGPRGD (SEQ ID NO: 25).

In some embodiments, the detected presence of NPM-ALK fusion protein corresponds with a t(2;5)(p23;q35) cytogenetic abnormality; BCR-ABL1 (E13a2) fusion protein corresponds with a (9;22)(q34;q11.2) cytogenetic abnormality; BCR-ABL1 (E1a2) fusion protein corresponds with a t(9;22) (q34;q11.2) cytogenetic abnormality; API2-MALT1 (ex7-ex5) fusion protein corresponds with a t(11;18)(q21;q21) cytogenetic abnormality; API2-MALT1 (ex7-ex8) fusion protein corresponds with a t(11;18)(q21;q21) cytogenetic abnormality; TPM3-ALK fusion protein corresponds with a t(1;2)(q25;p23) cytogenetic abnormality; CLTC-ALK fusion protein corresponds with a t(2;17)(p23;q23) cytogenetic abnormality; SQSTM1-ALK fusion protein corresponds with a t(2;5)(p23;q35) cytogenetic abnormality; MLL-AF4 fusion protein corresponds with a t(4;11)(q21;23) cytogenetic abnormality; MLL-AF9 fusion protein corresponds with a t(9;11)(p22;q23) cytogenetic abnormality; AML1-MTG8 fusion protein corresponds with a t(8;21)(q22;q22) cytogenetic abnormality; NUP98-HOXD13 fusion protein corresponds with a t(2;11)(q31;p15) cytogenetic abnormality; MLL-ELL fusion protein corresponds with a t(11;19) (q23;p13.3) cytogenetic abnormality; PML-RARA fusion protein corresponds with a t(15;17)(q22;q21) cytogenetic abnormality; EML4-ALK (variant 1, 2 or 3a) fusion protein corresponds with a inv(2)(p21;p23) cytogenetic abnormality; AKAP9-BRAF fusion protein corresponds with a inv(7)(q21; q34) cytogenetic abnormality; SYT-SSX1 or SYT-SSX2 fusion protein corresponds with a t(X;18)(p11.2;q11.2) cytogenetic abnormality; EWSR1-ERG fusion protein corresponds with a t(21;22)(q21;q12) cytogenetic abnormality; PAX3-FOXO1 fusion protein corresponds with a t(2;13) (q35;q14) cytogenetic abnormality; EWS/WT1 fusion protein corresponds with a t(11;22)(p13;q12) cytogenetic abnormality; EWSR1/ATF1 (fusion type 1 or 2) fusion protein corresponds with a t(12;22)(a13;q12) cytogenetic abnormality; and COL1A1-PDGFB fusion protein corresponds with a t(17;22)(q22;q13) cytogenetic abnormality.

In certain embodiments, the present invention provides methods for detecting the presence one or more chromosomal translocation-based conditions within a subject.

In certain embodiments, the present invention provides kits facilitating the performing of any of the methods of the present invention. For example, in some embodiments, the present invention provides a kit comprising labeled peptides having an amino acid sequence that spans the fusion junction of a fusion protein encoded by a fusion of a first nucleic acid to a second nucleic acid, wherein the labeled peptides comprise peptides having one isotopically labeled amino acid residue and peptides having two isotopically labeled amino acid residues, wherein the amino acid sequence of the labeled peptides is identical with an amino acid sequence of a fusion protein peptide fragment generated through digestion of the fusion protein with a protease, wherein the protease is known to generate upon digestion of the fusion protein a fusion protein peptide fragment having an amino acid sequence identical with the labeled peptides. In some embodiments, the present invention provides a kit comprising two or more distinct groups of labeled peptides, wherein each distinct group of labeled peptides is specific for a particular fusion protein, wherein the labeled peptides within each distinct group have labeled peptides having an amino acid sequence that spans the fusion junction of the particular fusion protein encoded by a fusion of a first nucleic acid to a second nucleic acid, wherein the labeled peptides within each group comprise peptides having one isotopically labeled amino acid residue and peptides having two isotopically labeled amino acid residues, wherein the amino acid sequence of the labeled peptides within each distinct group is identical with an amino acid sequence of a particular fusion protein peptide fragment generated through digestion of the particular fusion protein with a protease, and a protease known to generate upon digestion of the two or more fusion proteins to be detected particular fusion protein peptide fragments.

In certain embodiments, the present invention provides methods for monitoring a therapy for a chromosomal translocation-based condition comprising comparing quantified fusion protein levels at different time points with the fusion protein quantitation methods described herein.

Additional embodiments will be apparent to persons skilled in the relevant art based on the teachings contained herein.

DEFINITIONS

Figure 1:
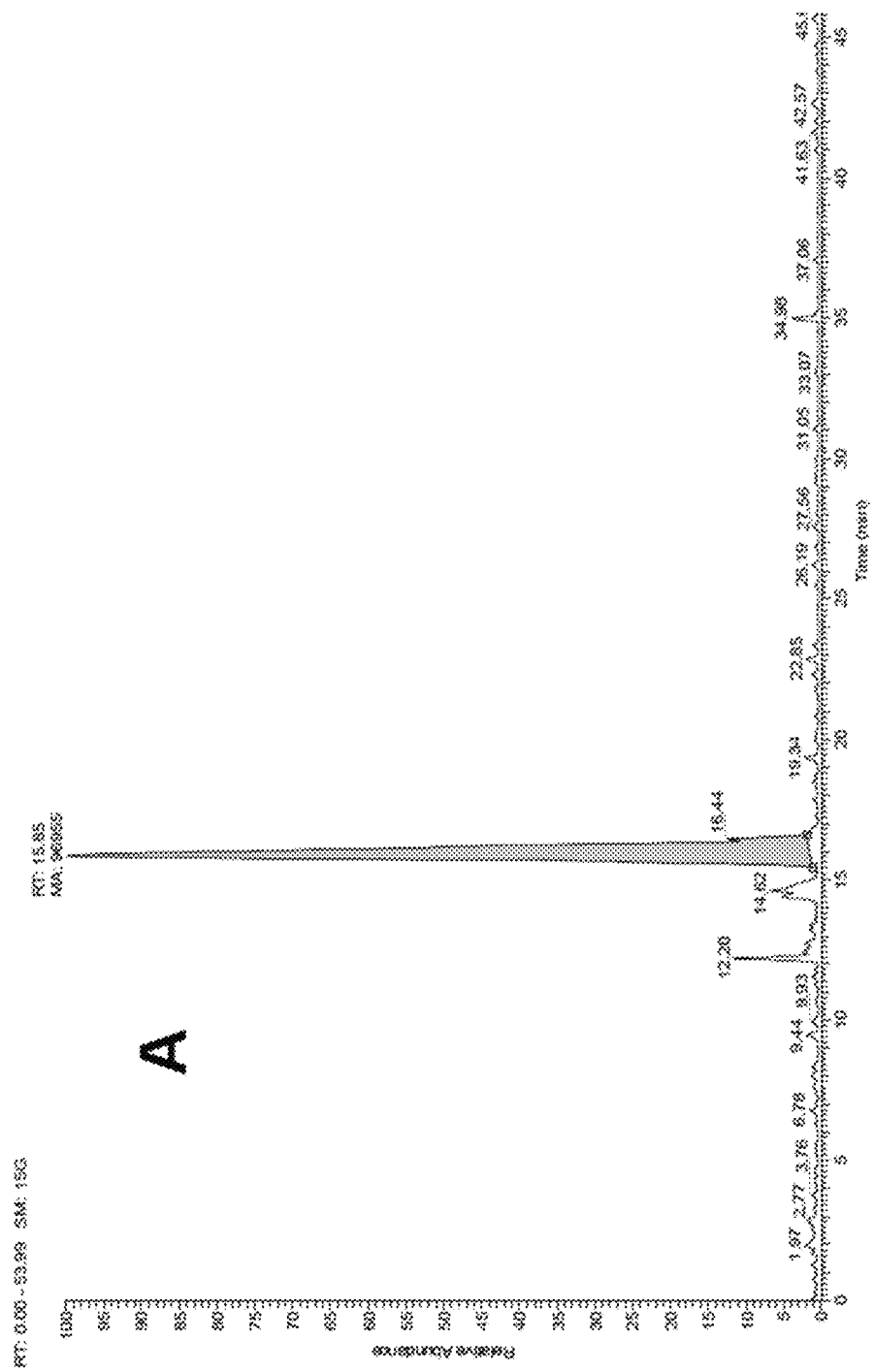
FIG. 1 shows API2-MALT1 and BCR-ABL1 extracted ion chromatograms and calibration curves. Extracted ion chromatograms of API2-MALT1 fusion peptides (A) SRS-VDGVSE (SEQ ID NO: 4) (468.23 m/z) and (B) ESRS-VDGVSESK (SEQ ID NO: 5) (640.31 m/z) and BCR-ABL1 fusion peptides (C) TINKEEAL (SEQ ID NO: 2) (459.25 m/z) and (D) HGDAEAL (SEQ ID NO: 3) (356.667 m/z) using HILIC chromatography showing a summed response for the monitored transitions. Calibration curves of the API2-MALT1 fusion peptides (E) SRSVDGVSE (SEQ ID NO: 4) (468.23 m/z) 0.375 to 60 fmole/µL and (F) ESRSVDGVS-ESK (SEQ ID NO: 5) (640.31 m/z) 0.063 to 30 fmole/µL in a BSA background and BCR-ABL1 fusion peptides (G) TIN-KEEAL (SEQ ID NO: 2) (459.25 m/z) 7.82 to 500 fmole/µL and (H) HGDAEAL (SEQ ID NO: 3) (356.667 m/z) 15.6 to 250 fmole/µL in a chymotrypsin digested plasma background.
Figure 1:
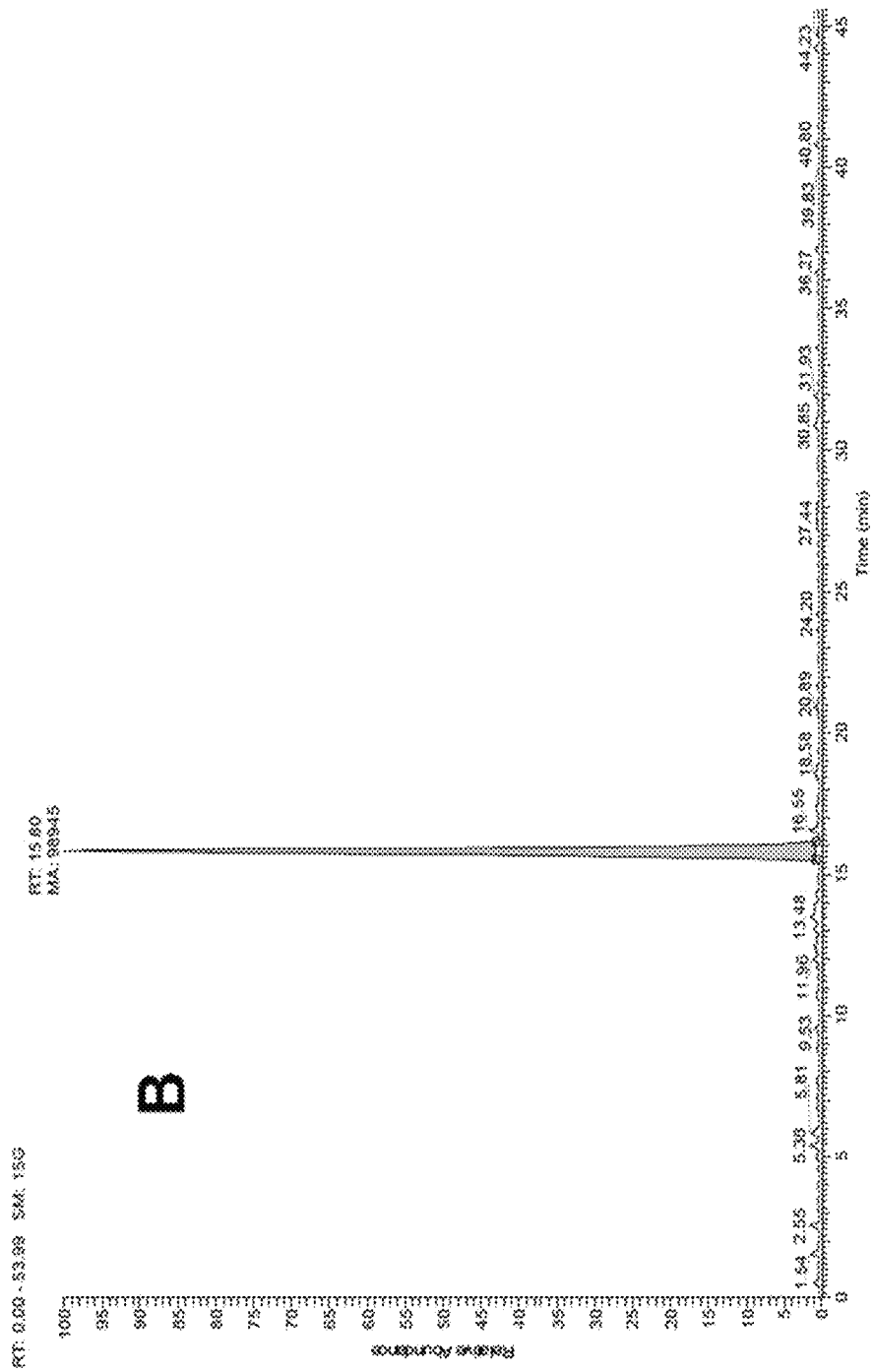
Figure 1:
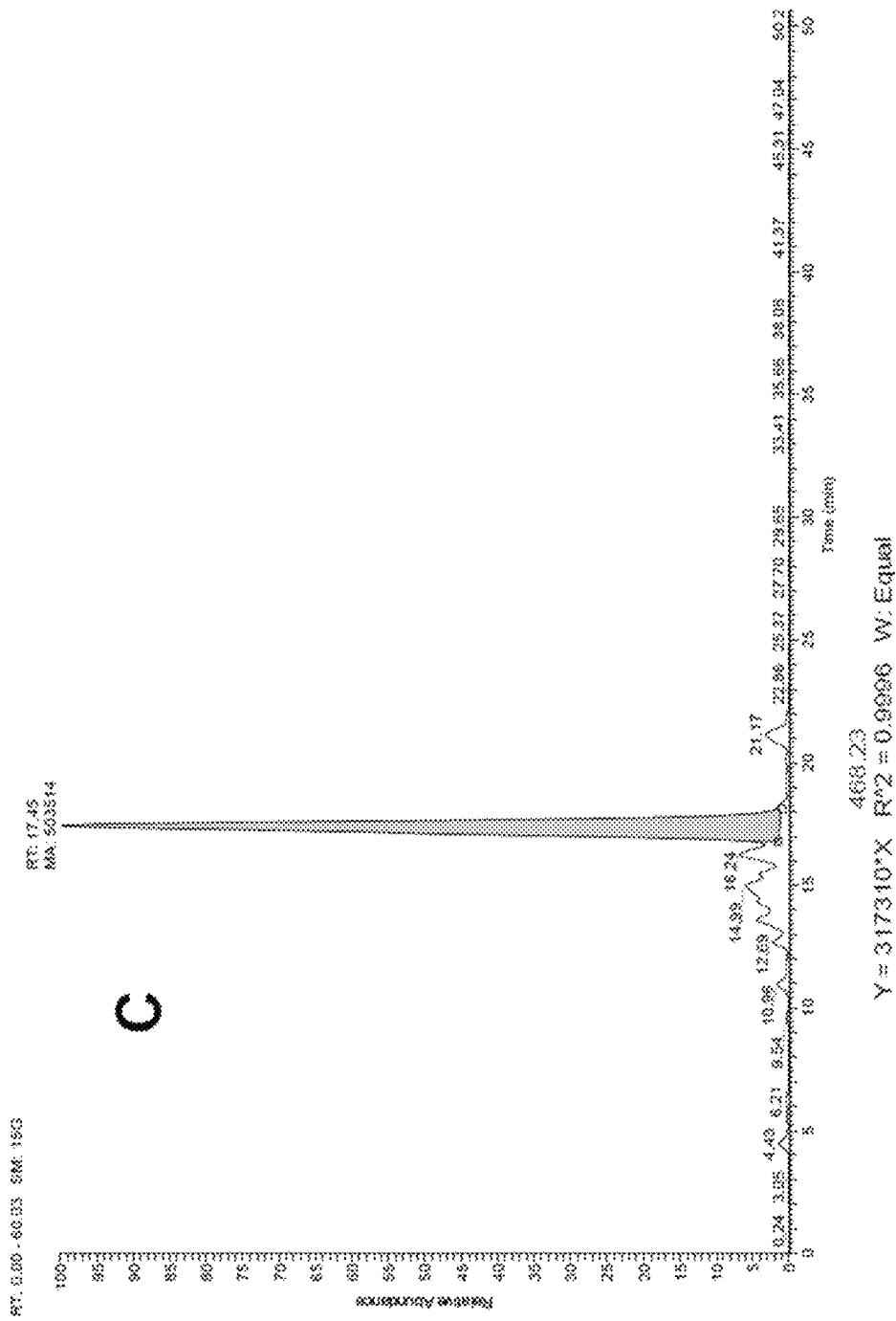
Figure 1:
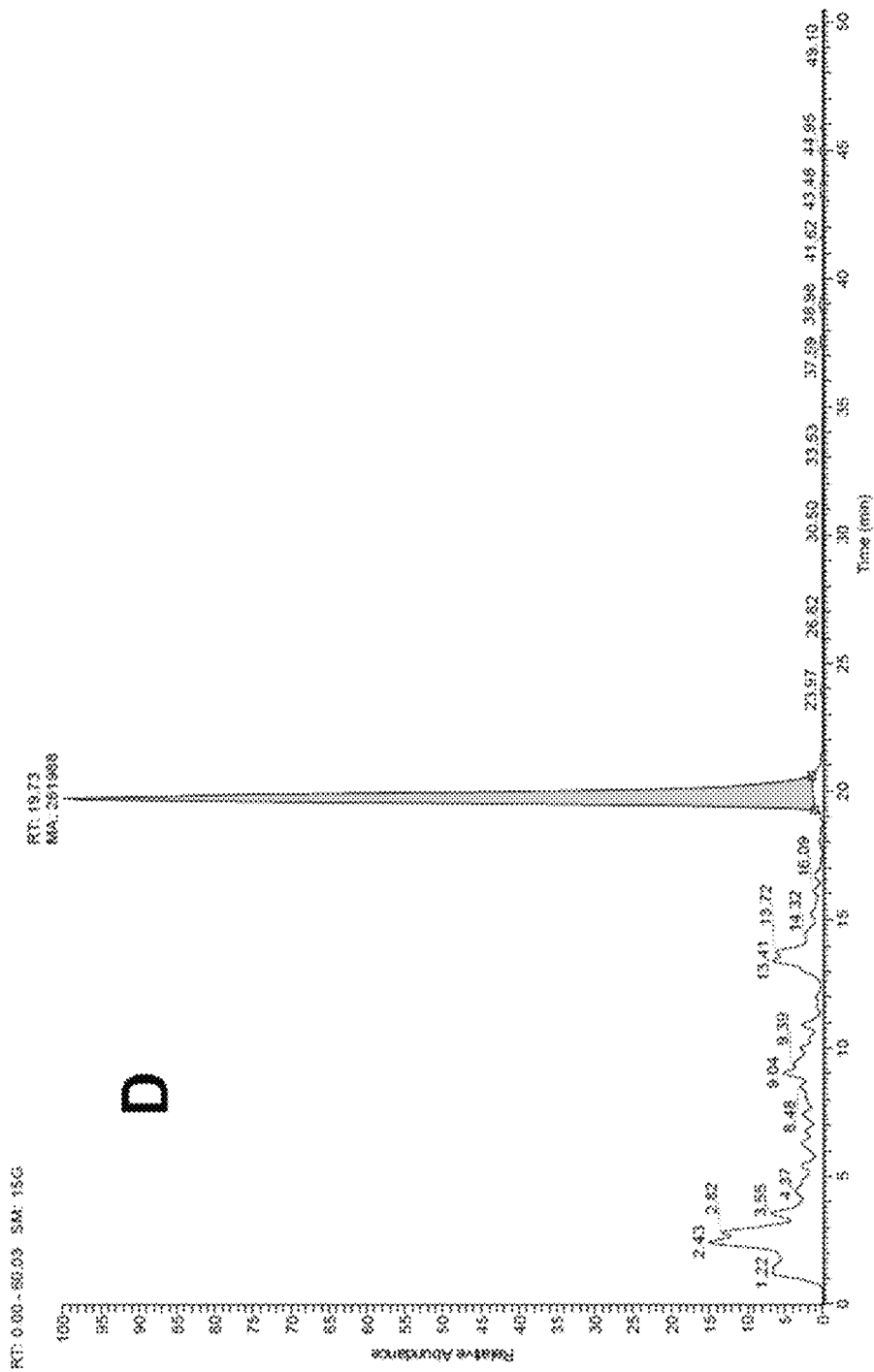
Figure 1:
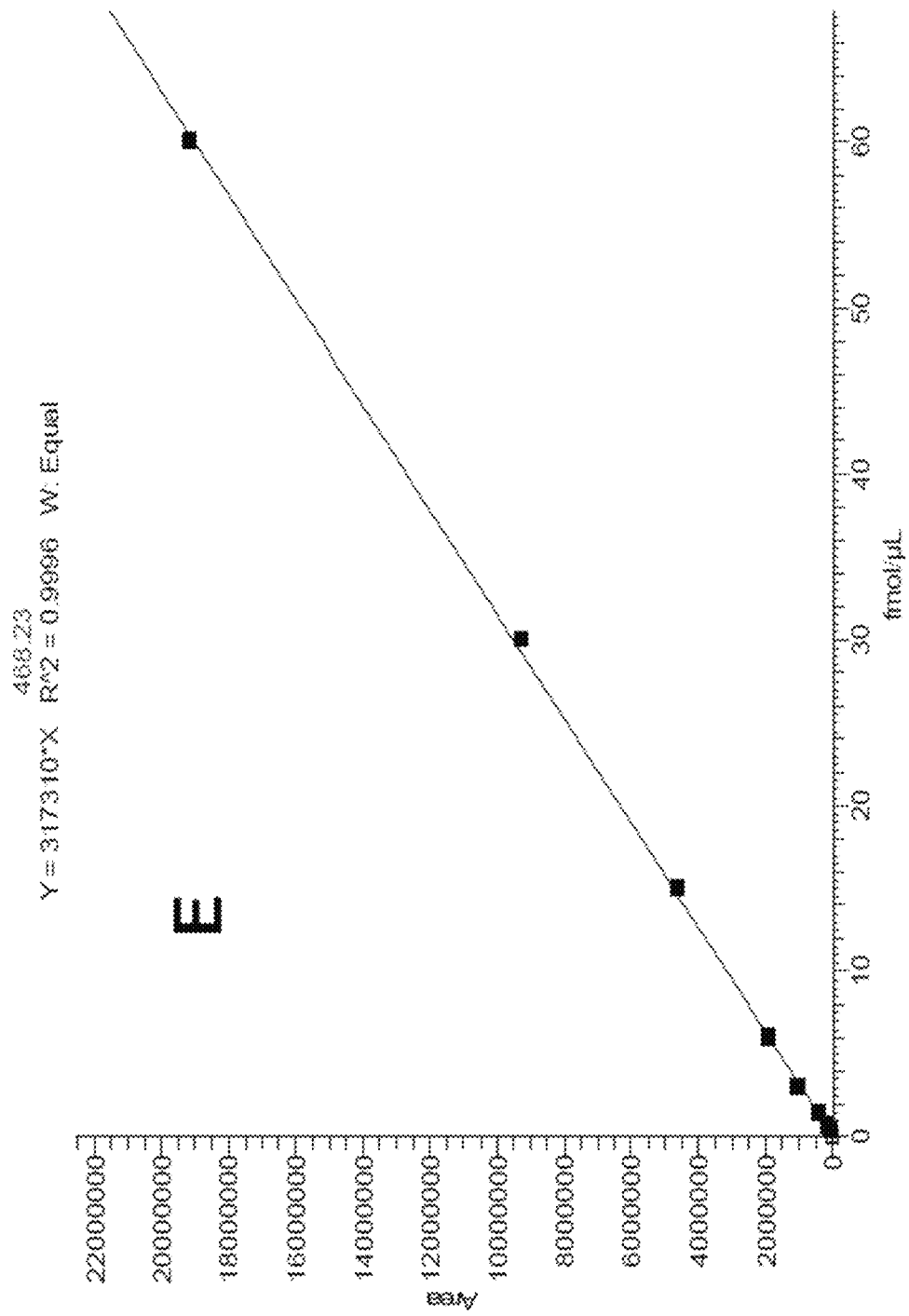
Figure 1:
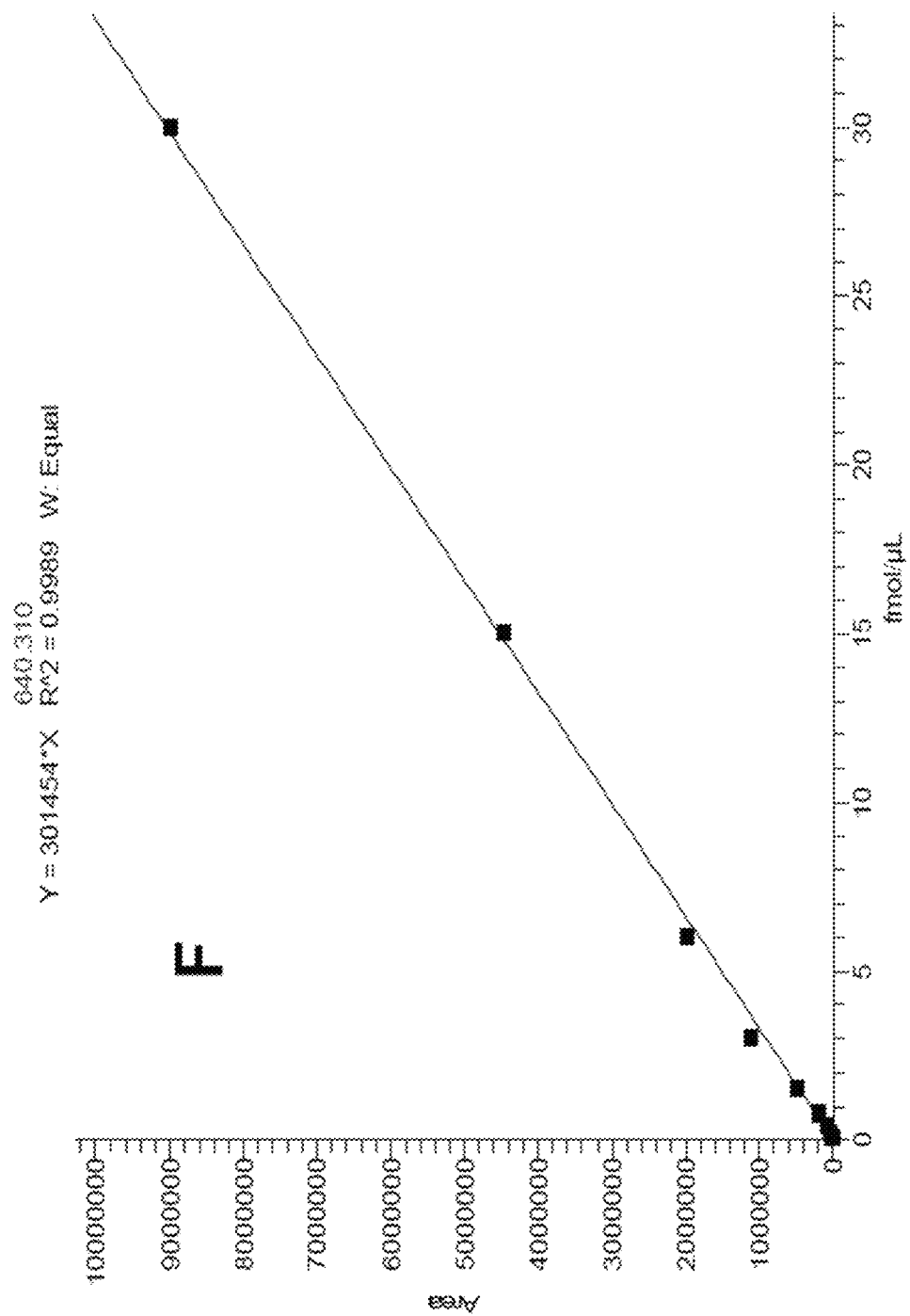
Figure 1:
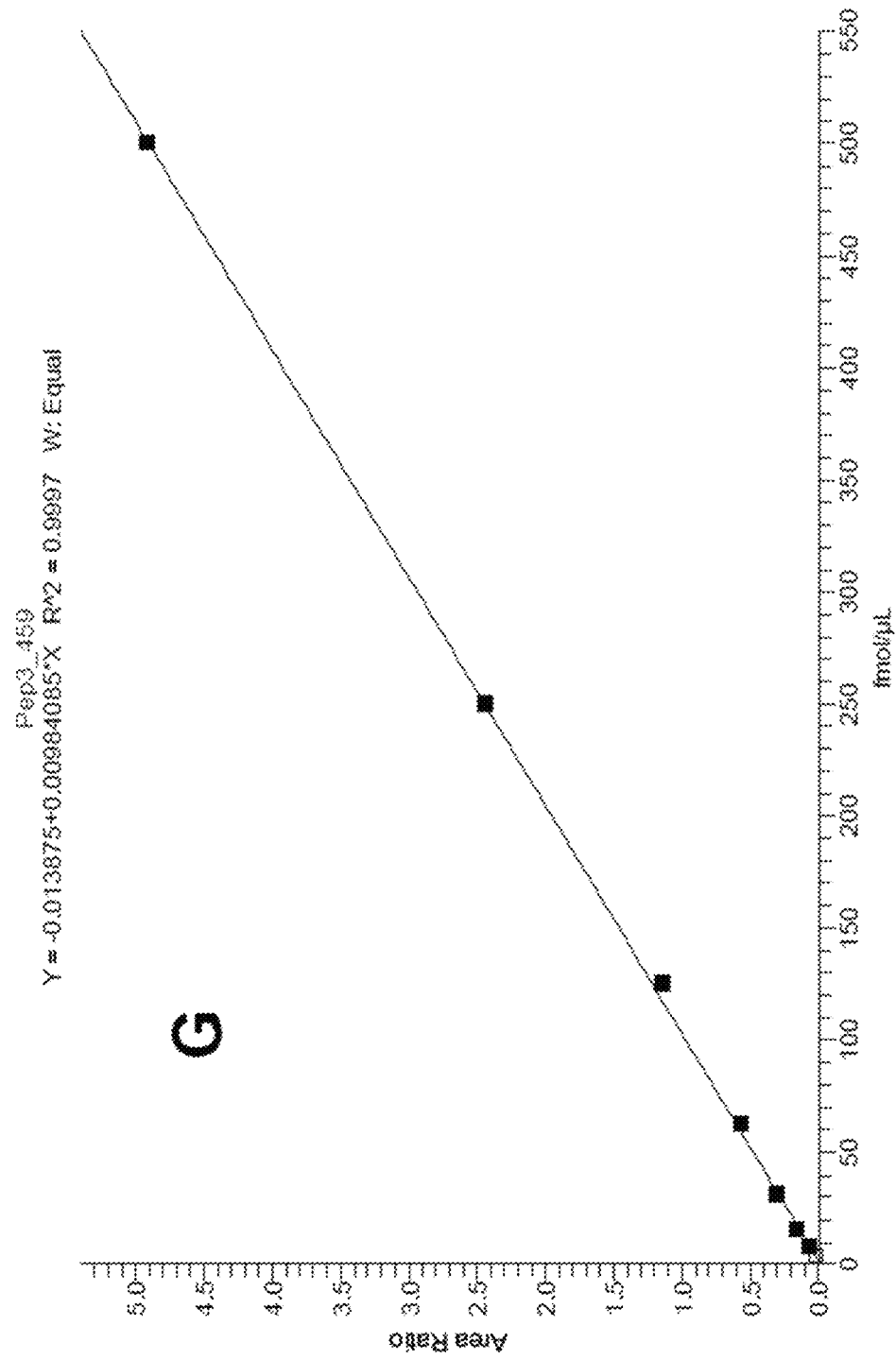
Figure 1:
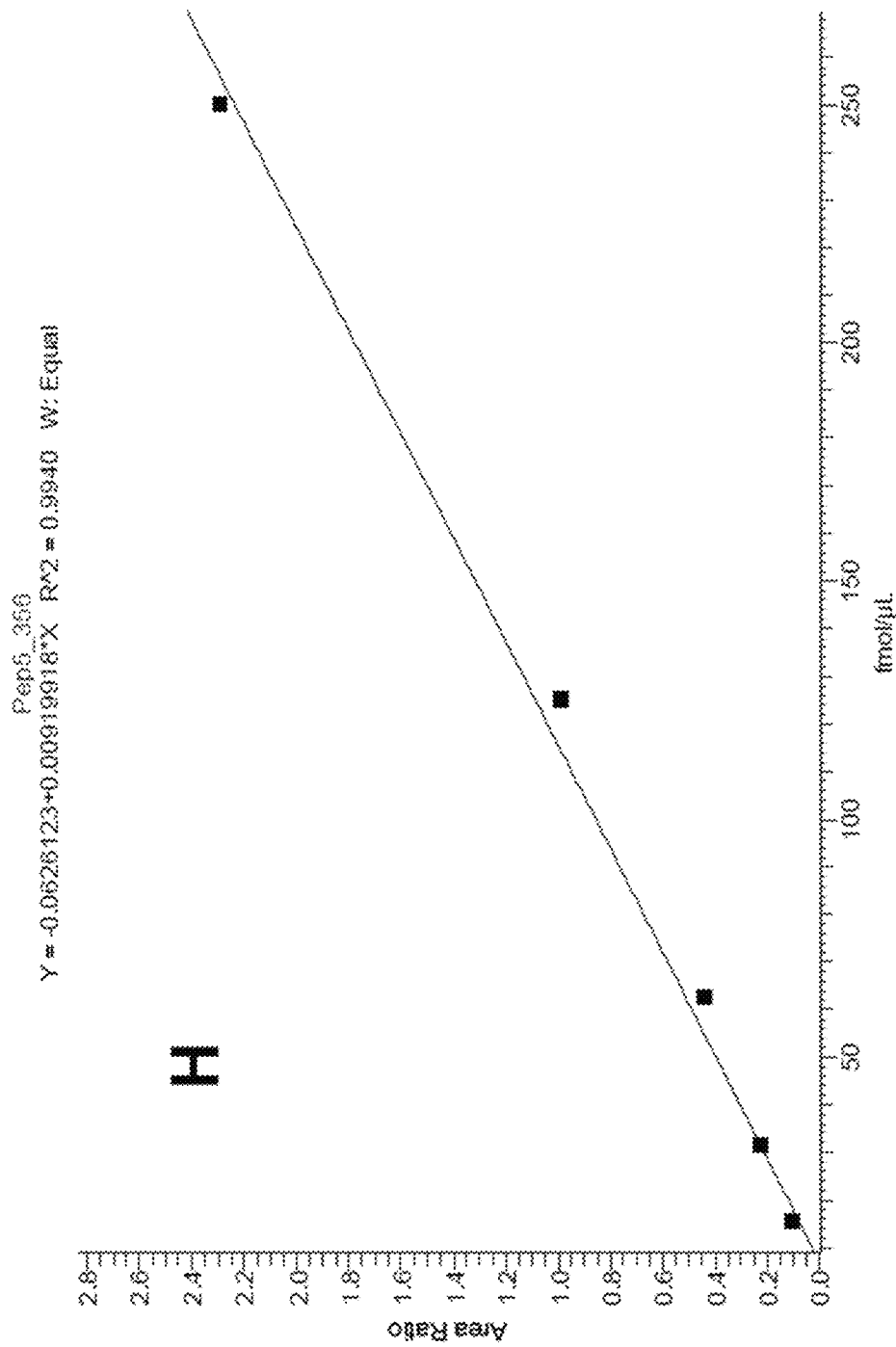

To facilitate an understanding of the present invention, a number of terms and phrases are defined below.

As used herein, the term "sensitivity" is defined as a statistical measure of performance of an assay (e.g., method, test), calculated by dividing the number of true positives by the sum of the true positives and the false negatives.

As used herein, the term "specificity" is defined as a statistical measure of performance of an assay (e.g., method, test), calculated by dividing the number of true negatives by the sum of true negatives and false positives.

As used herein, the term "informative" or "informativeness" refers to a quality of a marker or panel of markers, and specifically to the likelihood of finding a marker (or panel of markers) in a positive sample.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body.

The term "neoplasm" as used herein refers to any new and abnormal growth of tissue. Thus, a neoplasm can be a premalignant neoplasm or a malignant neoplasm. The term "neoplasm-specific marker" refers to any biological material that can be used to indicate the presence of a neoplasm. Examples of biological materials include, without limitation, nucleic acids, polypeptides, carbohydrates, fatty acids, cellular components (e.g., cell membranes and mitochondria), and whole cells.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "chromosomal translocation" refers to an event wherein a fragment of one chromosome is broken off and is then attached to another chromosome, which may be of a different pair. The translocations are generally between non-homologous chromosomes but can be between homologous chromosomes. In particular, the fusion gene products generated by the chromosomal translocation are intracellularly located. Polynucleotides (which may be referred to herein as genes) that may be affected by chromosomal translations include gene fusions wherein the breakpoints reside within introns of the affected genes on the two chromosomes of concern, for example.

As used herein, the term "chromosomal translocation-based condition" refers to any type of health status, disorder or disease associated with and/or resulting from a chromosomal translocation. Examples include, but are not limited to, ALK-positive anaplastic large cell lymphoma, chronic myeoloid leukemia, B-cell acute lymphoblastic leukemia, mucosa associated lymphoid tissue, ALK-positive diffuse large B-cell lymphoma, anaplastic large cell lymphoma, biphenotypic acute lymphoblastic leukemia, acute myeloid leukemia, non small cell lung cancer, papillary thyroid carcinoma, synovial sarcoma, Ewing sarcoma, alveolar rhabdomyosarcoma, desmoplastic small round cell tumor, clear cell sarcoma, and dermatofibrosarcoma protuberans. In some embodiments, detection of a fusion protein resulting from such a chromosomal translocation is a biomarker for such a chromosomal translocation-based condition.

As used herein, the term "fusion protein" refers to a polypeptide encoded by a polynucleotide wherein the polynucleotide is the result of fusion between at least two polynucleotides, such as from two different genes, including the polynucleotides that result upon chromosomal translocation.

In other words, the fusion protein comprises at least two different regions: one region encoded from one polynucleotide or gene or nucleic acid and a second region encoded from another polynucleotide or gene or nucleic acid. In some embodiments, the fusion protein is the result of a chromosomal translocation. In some embodiments, the fusion protein is the result of a splice variation.

As used herein, the term "splice variants" or "splice variation," is the result of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

As used herein, the term "sample" refers to a representative entity from any organism, including humans, animals, and plants, as well as cell cultures, recombinant cells, cell components, and environmental sources, for example. They may comprise a biological tissue, fluid, or specimen. Samples may be obtained from any animal, including, a mammal, for example, human, horse, dog, cat, sheep, goat, cow, and pig. Samples may include, but are not limited to, amniotic fluid, blood, blood cells, perspiration, cerebrospinal fluid, fine needle biopsy samples, peritoneal fluid, plasma, pleural fluid, saliva, semen, serum, sputum, tissue or tissue homogenates, tissue culture media, urine, and the like. Samples may also be processed, such as sectioning of tissues, fractionation, purification, or cellular organelle separation.

As used herein, the term "purification" or "purifying" refers generally to a procedure that enriches the amount of one or more analytes of interest (e.g., peptides, labeled peptides) relative to other components in a biological sample that may interfere with detection of the analyte of interest. Purification of the sample by various means may allow relative reduction of one or more interfering substances, e.g., one or more substances that may or may not interfere with the detection of a selected peptide or labeled peptide.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

As used herein, the term "high performance liquid chromatography" or "HPLC" refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography (HTLC) or high throughput liquid chromatography) refers to a form of chromatography that utilizes turbulent flow of the material being assayed through the column packing as the basis for performing the separation.

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 μm. As used in this context, the term "about" means±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means±10%. In a preferred embodiment the analytical column contains particles of about 4 μm in diameter.

As used herein, the term "tumor load" refers to the amount of cancer cells, the tumor size, or the amount of cancer in a subject (e.g., a human patient). In specific embodiments, the tumor load may be referred to as "tumor burden."

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z") (see, e.g., U.S. Pat. Nos. 6,204,500, 6,107,623, 6,268,144, 6,124,137, Wright et al., Prostate Cancer and Prostatic Diseases 1999, 2:264-76; Merchant and Weinberger, Electrophoresis 2000, 21: 1164-67).

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photoionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photoionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which may be heated to prevent condensation and to facilitate solvent evaporation. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heats causes the sample to transfer into the gas phase. The gas phase sample is then drawn into the mass spectrometer.

As used herein, the term "selective ion monitoring" is a detection mode for a mass spectrometric instrument in which only ions within a relatively narrow mass range, typically about one mass unit, are detected.

As used herein, "multiple reaction monitoring," sometimes known as "selected reaction monitoring," is a detection mode for a mass spectrometric instrument in which a precursor ion and one or more fragment ions are selectively detected.

As used herein, the term "limit of quantification", "limit of quantitation" or "LOQ" refers to the point where measurements become quantitatively meaningful. The analyte response at this LOQ is identifiable, discrete and reproducible with a relative standard deviation (RSD %) of 20% and an accuracy of 80% to 120%.

As used herein, the term "limit of detection" or "LOD" is the point at which the measured value is larger than the uncertainty associated with it. The LOD is the point at which a value is beyond the uncertainty associated with its measurement and is defined as two times the RSD of the mean at the zero concentration.

As used herein, an "amount" of an analyte in a biological sample (e.g., body fluid) refers generally to an absolute value reflecting the mass of the analyte detectable in volume of biological sample. However, an amount also contemplates a relative amount in comparison to another analyte amount. For example, an amount of analyte in a biological sample (e.g., body fluid) can be an amount which is greater than a control or normal level of analyte normally present.

DETAILED DESCRIPTION OF THE INVENTION

A cancer biomarker is generally an analyte that indicates the presence or extent of a specific form of cancer. A useful cancer biomarker should reliably distinguish between benign and malignant states, and ideally, distinguish one form of cancer from other related differential diagnoses. Many human cancers contain recurrent chromosomal translocations and chimeric gene fusions that could be exploited as cancer-specific biomarkers (see, e.g., Rowley J D: Nat Rev Cancer 1: 245-50, 2001; Stratton M R, Campbell P J and Futreal P A: The cancer genome. Nature 458: 719-24, 2009; each herein incorporated by reference in its entirety).

Chromosomal translocations bring two previously unlinked regions of the genome together and in certain cases can result in disease by inducing synthesis of a novel fusion protein. This phenomenon is significant when the breakpoint of the translocation affects an oncogene, for example, and results in cancer. Indeed, several of the structural aberrations associated with chromosomal translocations are specific and pathognomonic for distinct types of cancer (see, e.g., Mitelman F, Johansson B and Mertens F: Nat Rev Cancer 7: 233-45, 2007; herein incorporated by reference in its entirety). Moreover, since new molecular therapies increasingly target oncogenic fusion proteins, the detection and quantitation of these proteins may also provide important, direct therapeutic guidance (see, e.g., Druker B J, et al.: Nat Med 2: 561-6, 1996; Druker B J, et al.: N Engl J Med 344: 1031-7, 2001; Kwak E L, et al.: N Engl J Med 363: 1693-703, 2010; each herein incorporated by reference in its entirety).

While genomic techniques targeting fusion partner genes are routinely used for diagnosing cancers, fusion peptides resulting from oncogenic chimeric fusions are unexplored as biomarker candidates for cancer detection. The specificity and qualitative/binary nature (i.e. present or absent) of fusion proteins in specific tumor types, renders these analytes attractive candidates for cancer detection. Despite their enormous potential as biomarkers, however, fusion peptides resulting from oncogenic chimeric fusions have not been exploited for specific and sensitive detection of cancer. Indeed, the use of fusion protein biomarkers has been limited by the availability of suitable techniques for their accurate detection (see, e.g., Carr S A and Anderson L: Clin Chem 54: 1749-52, 2008; herein incorporated by reference in its entirety). The high false-discovery rates of large scale methods of analyte interrogation, the low levels of the candidate biomarkers, and the inherently variable signal to noise ratios of immunologic assays have remained significant barriers.

The present invention addresses such limitations. Indeed, experiments conducted during the course of developing embodiments for the present invention demonstrate the detection of use of fusion peptides resulting from oncogenic chimeric fusions specific for various forms of cancer (e.g., chromosomal translation-based cancers), and as such, demonstrate the use of fusion peptides resulting from oncogenic chimeric fusions as specific and sensitive biomarkers of cancer. Moreover, such experiments demonstrate the utility, in a clinically relevant scenario, of a multiple reaction monitoring via mass spectrometry (MRM-based MS) approach combined with an innovative double stable isotope strategy for the identification of fusion peptides as biomarkers specific for various forms of cancer.

Accordingly, the present invention provides fusion proteins as biomarkers specific for chromosomal translocation-based conditions (e.g., cancer), related methods for detecting fusion protein biomarkers associated with chromosomal translocation-based conditions, related methods for quantifying amount of fusion protein expression, and related methods for diagnosing chromosomal translocation-based conditions through detection of such fusion protein biomarkers. Such fusion protein biomarkers and related methods additionally find use in research settings.

Suitable samples for use in the methods of the present invention include any sample that may contain the analyte of interest (e.g., a fusion protein). In some embodiments, a sample is a biological sample; that is, an aqueous sample obtained from any biological source, such as an animal, a cell culture, an organ culture, etc. In some embodiments, samples are obtained from a mammalian animal, such as a dog, cat, horse, etc. In some embodiments, the mammalian animals are primates, most preferably male or female humans. In some embodiments, the samples include bodily fluids such as urine, blood, plasma, serum, saliva, cerebrospinal fluid, or tissue samples. Such samples may be obtained, for example, from a patient; that is, a living person, male or female, presenting oneself in a clinical setting for diagnosis, prognosis, or treatment of a disease or condition. Such samples may be obtained from a human patient suspected of having a chromosomal translocation-based condition (e.g., cancer). In some embodiments, such samples may be obtained from a human undergoing a cancer screening.

In some embodiments, the methods utilize labeled peptides matching peptide fragments from a fusion protein of interest so as to increase specificity and sensitivity associated with fusion protein detection and/or quantitation associated with mass spectrometry techniques (e.g., MRM-MS). For example, in some embodiments, the methods provide labeled peptides having an amino acid sequence that spans the fusion junction of a fusion protein encoded by a fusion of a first nucleic acid (e.g., gene) to a second nucleic acid (e.g., gene) (e.g., resulting from a chromosomal translocation) for purposes of characterizing, detecting and/or quantitating such a fusion protein within a biological sample. Such labeled peptides are not limited to a particular amino acid sequence length.

The labeled peptides are not limited to a particular manner of labeling. In some embodiments, the labeled peptides comprise labeled peptides having one isotopically labeled amino acid within its amino acid sequence ("heavy labeled peptides"), and labeled peptides having two isotopically labeled amino acids within its amino acid sequence ("double-heavy labeled peptide"). The labeled peptides are not limited to a particular manner of isotopic labeling. In some embodiments wherein the labeled peptide contains one isotopically labeled amino acid residue, one amino acid residue is "heavy" (e.g., $^{13}C/^{15}N$) (e.g., $^{13}C_6/^{15}N_4$). In some embodiments wherein the labeled peptide contains two isotopically labeled amino acid residues, two of the amino acid residues are "heavy" (e.g., $^{13}C/^{15}N$) (e.g., $^{13}C_6/^{15}N$ and $^{13}C_6/^{15}N_4$) (e.g., "double heavy").

In some embodiments, the amino acid sequence of the labeled peptides is identical with an amino acid sequence of a fusion protein peptide fragment generated through digestion of the fusion protein with a protease. The methods are not limited to the use of a particular protease (e.g., trypsin, chymotrypsin, V8-DE, Lys-C, and Arg-C). In some embodiments, the protease is known to generate upon digestion of the fusion protein a fusion protein peptide fragment having an amino acid sequence identical with the amino acid sequence of the labeled peptides. The use of "heavy" and "double-heavy" labeled peptides having an amino acid sequence identical with an amino acid sequence of a fusion protein peptide fragment generated through digestion of the fusion protein with such a protease creates an internal reference point for such a fusion protein fragment upon analysis with MRM-MS, thereby increasing detection specificity and sensitivity.

Such methods further involve digestion and purification of the biological sample prior to analysis with mass spectrometry techniques (e.g., MRM-MS). The methods are not limited to a particular manner of digesting and purifying the biological sample. In some embodiments the methods involve the use of a protease (e.g., a protease is known to generate upon digestion of a fusion protein of interest a fusion protein peptide fragment having an amino acid sequence identical with the amino acid sequence of the labeled peptides) to digest a biological sample from a subject so as to generate biological sample-based peptide fragments. In some embodiments, following such digestion, the methods further involve combining with the biological sample-based peptide fragments the labeled peptides. In some embodiments, following such combination, the biological sample-based peptide fragments and labeled peptides are purified.

The methods are not limited to a particular manner of purifying the combined biological sample-based peptide fragments and labeled peptides. In some embodiments, the combined biological sample-based peptide fragments and labeled peptides are purified via chromatography methods. The methods are not limited to utilizing a particular chromatography method. In some embodiments, for example, high performance liquid chromatography is utilized. In some embodiments, the methods utilize HPLC to perform a purification of selected analytes (e.g., biological sample-based peptide fragments, fusion protein peptide fragments, labeled peptides).

The methods of the present invention are not limited to a particular manner of characterizing (e.g., detecting and quantifying) the purified biological sample-based peptide fragments combined with the labeled peptides. In some embodiments, such characterizing involves mass spectrometry techniques. For example, in some embodiments, the purified biological sample-based peptides combined with labeled peptides is used with methods of mass spectrometry (MRM-MS), thereby providing a high-throughput assay system for detecting and quantifying one or more selected analytes (e.g., fusion protein peptide fragments, labeled peptides). In some embodiments, the methods are particularly well suited for application in large clinical laboratories for automated assay.

The methods of the present invention are not limited to a particular manner of conducting mass spectrometry techniques. In some embodiments, mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. The skilled artisan will understand that the choice of ionization method may be determined based on the analyte to be measured, type of sample, the type of detector, the choice of positive versus negative mode, etc.

In some embodiments, the mass spectrometry techniques are performed in positive ion mode. Alternatively, in some embodiments, the mass spectrometry techniques are performed in negative ion mode. Various ionization sources, including for example atmospheric pressure chemical ionization (APCI) or electrospray ionization (ESI), may be used in embodiments of the present invention. In mass spectrometry techniques generally, after the sample has been ionized, the positively charged or negatively charged ions thereby created may be analyzed to determine a mass-to-charge ratio. Suitable analyzers for determining mass-to-charge ratios include quadrupole analyzers, ion trap analyzers, and time-of-flight analyzers.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion is subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of filtration/fragmentation may be used to eliminate interfering substances, and may be particularly useful in complex samples, such as biological samples.

The ions may be detected using several detection modes. For example, selected ions may be detected, i.e. using a selective ion monitoring mode (SIM), or alternatively, ions may be detected using a scanning mode, e.g., multiple reaction monitoring (MRM) or selected reaction monitoring (SRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected. Thus, quadrupole instruments may act as both a "mass filter" and as a "mass detector" for the ions injected into the instrument.

The mass spectrometer typically provides the user with an ion scan; that is, the relative abundance of each ion with a particular mass/charge over a given range (e.g., 90 to 1000 amu). The results of an analyte assay, that is, a mass spectrum, may be related to the amount of the analyte in the original sample by numerous methods known in the art. For example, given that sampling and analysis parameters are carefully controlled, the relative abundance of a given ion may be compared to, for example, a table that converts that relative abundance to an absolute amount of the original molecule. Alternatively, molecular standards may be run with the samples, and a standard curve constructed based on ions generated from those standards. Using such a standard curve, the relative abundance of a given ion may be converted into an absolute amount of the original molecule. In some embodiments, one or more internal standards may be used to generate standard curves for calculating the quantity of a peptide of interest or a labeled peptide. Methods of generating and using such standard curves are well known in the art and one of ordinary skill is capable of selecting appropriate internal standards.

Advances in mass spectrometry permit direct and unbiased interrogation of proteins and peptides in complex mixtures with unambiguous identification of specific proteins (see, e.g., Domon B and Aebersold R: Science 312: 212-7, 2006; Yates J R, Ruse C I and Nakorchevsky A: Annu Rev Biomed Eng 11: 49-79, 2009; each herein incorporated by reference in its entirety). Multiple reaction monitoring (MRM) via mass spectrometry is a powerful approach for the targeted detection of biomarker candidates in a complex background (see, e.g., Picotti P and Aebersold R: Nat Methods 9: 555-66, 2012; herein incorporated by reference in its entirety). MRM involves the focused interrogation of specific m/z windows for the precursor analyte as well as selected fragment ions following MS/MS analysis. By focusing only on specific m/z windows, the sensitivity of detection is dramatically increased and within the context of a complex mixture has the potential for a reproducible dynamic range spanning ≥4 orders of magnitude (see, e.g., Anderson L and Hunter C L: Mol Cell Proteomics 5: 573-88, 2006; Keshishian H, et al.: Mol Cell Proteomics 6: 2212-29, 2007; each herein incorporated by reference in its entirety).

Experiments conducted during the course of developing embodiments for the present invention demonstrated the utility, in a clinically relevant scenario, of an MRM-based MS approach combined with a double stable isotope strategy for the identification of fusion peptides arising from a corresponding fusion protein resulting from a chromosomal translocation. This simple "heavy/double heavy" labeled internal standards strategy permits standard curve construction for every sample and an area ratio (heavy/double heavy) may be calculated for each point on the calibration curve. With this approach, accurate determination of the levels of endogenous analyte are thus possible even at the limit of detection, since potential matrix effect differences between samples are essentially negated. Indeed, such experiments demonstrated, for example, the use of nucleophosmin-anaplastic lymphoma kinase (NPM-ALK) fusion peptides arising from the corresponding chimeric fusion protein for the identification of NPM-ALK positive anaplastic large cell lymphoma (ALCL). Such experiments further demonstrated exquisite specificity and sensitivity of this fusion peptide multiple reaction monitoring (MRM) approach and its application in clinical biopsy material with extraordinary accuracy.

Such multiple reaction monitoring via mass spectrometry-based methods for detecting the presence of a fusion protein within a biological sample offers several advantages that are apparent from the results of the experiments conducted during the course of developing embodiments of the present invention. By targeted monitoring of multiple transitions, the approach provides exquisite specificity as observed in such experiments. For example, the methods of the present invention permitted high sensitivity detection of the NPM-ALK fusion at levels as low as 0.439 fmole/µL (220 fmoles/mg lysate) without the need for fusion-protein specific antibody enrichment or target amplification strategies (as are typically employed for immunophenotypic or polymerase chain reaction (PCR) based detection of oncogenic chimeric fusions). Specifically in this regard, the lack of necessity for nucleic acid amplification is advantageous as it avoids PCR-associated contamination issues (see, e.g., Wang Q, et al.: Proc Natl Acad Sci USA 108: 2444-9, 2011; herein incorporated by reference in its entirety). The implementation of accurate protein biomarkers in clinically useful scenarios has been challenging because many biomarker candidates are expressed in non-disease states and thus the establishment of universal quantitative threshold levels for unequivocal diagnosis of disease is difficult. In this regard, chimeric fusion proteins arising from chromosomal translocations are ideal biomarkers because of their qualitative nature and pathognomonic specificity in several forms of cancer. Overall, the approach is fairly simple to implement and scalable for analysis of multiple samples and specimen types.

As such, in some embodiments, multiple reaction monitoring via mass spectrometry techniques are utilized to characterize the purified biological sample-based peptide fragments combined with the labeled peptides. In some embodiments, the MRM-MS analysis comprises an ionization technique such as, for example, photoioinization, electrospray ionization, atmospheric pressure chemical ionization, and electron capture ionization. In some embodiments, the ionization is performed in positive or negative mode. Use of the labeled peptides (the two mass discriminable synthetic stable isotope labeled peptides) with the assay design facilitates accurate detection and quantification of an endogenous peptide specific for a fusion protein within the biological sample. Determining the presence of a particular fusion protein within the biological sample is accomplished through analysis of the results of the mass spectrometry (e.g., multiple reaction monitoring via mass spectrometry) characterization (e.g., analysis of the extracted ion chromatogram for the detected peptides). For example, in some embodiments, detected co-elution of i) a biological sample-based fusion protein peptide fragment having an amino acid sequence identical with said labeled peptides, and ii) said labeled peptides, indicates the presence of the fusion protein within the biological sample. Conversely, for example, in some embodiments, a lack of detected co-elution of i) a biological sample-based fusion protein peptide fragment having an amino acid sequence identical with said labeled peptides, and ii) said labeled peptides indicates the absence of the fusion protein within the biological sample. In some embodiments, the levels of fusion protein to be detected and/or quantitated within said biological sample are approximately as low as 0.4 fmole µL (222 fmoles/mg lysate).

In some embodiments, the quantity of fusion protein expression may be determined through analysis of the results of the mass spectrometry (e.g., multiple reaction monitoring via mass spectrometry) characterization (e.g., analysis of the extracted ion chromatogram for the detected peptides). For example, in some embodiments, through detecting the quantity of fusion protein expression, the tumor burden associated with such fusion protein may be quantified. Such quantification of tumor burden may be used, in some embodiments, in characterizing a subject's response to a particular therapy, a subject's prognosis, etc.

In some embodiments, fusion proteins may not only be detected within a sample through use of mass spectrometry techniques (e.g., multiple reaction monitoring via mass spectrometry), but may also be quantified. For example, in some embodiments, the amount of a particular fusion peptide within a biological sample is determined through subjecting the digested biological sample peptide fragments and labeled peptides to ionization under conditions suitable to produce one or more ions detectable by mass spectrometry, and determining the amount of particular biological sample peptide fragment(s) by, for example, tandem mass spectrometry, and using the detect amount of such ion specific for the particular biological sample peptide fragment(s) to determine the amount of the actual fusion protein within the biological sample.

The methods are not limited to identifying and/or detecting particular types of fusion proteins resulting from chromosomal translocations. Indeed, any type of fusion protein can be detected through use of the methods of the present invention. Examples include, but are not limited to, the fusion proteins recited in Table 3. In some embodiments, the fusion protein is the result of a chromosomal translocation. In some embodiments, the fusion protein is the result of a splice variation.

The methods of the present invention may further be used to determine if a subject (e.g., a human patient suspected of having a chromosomal translocation-based condition) has a chromosomal translocation-based condition through detection of a fusion protein associated with such a condition. Any kind of chromosomal translocation-based condition associated with fusion protein expression can be determined with such methods. Indeed, the present invention is not limited to particular types or kinds of chromosomal translocation-based conditions. Examples of such chromosomal translocation-based conditions include, but are not limited to, Burkitt's lymphoma (t(8;14)(q24;q32)) (fusion of c-myc and IGH@), mantle cell lymphoma (t(11;14)(q13;q32)) (fusion of cyclin D1 and IGH@), follicular lymphoma (t(14;18)(q32;q21) (fusion of IGH@ and Bcl-2), papillary thyroid cancer (t(10; (various))(q11; (various))) (fusion of RET proto-oncogene and NTRK1), follicular thyroid cancer (t(2;3)(q13;p25) (fusion of PAX8 and PPARγ1), acute myeloblastic leukemia with maturation (t(8;21)(q22;q22)) (fusion of ETO and AML1), chronic myelogenous leukemia (CML)/acute lymphoblastic leukemia (AML) (t(9;22)(q34;q11)) (fusion of Abl1 and BCR), acute promyelocytic leukemia (t(15;17) (q22;q21)) (fusion of PML protein and RAR-α), acute myeloid leukemia/congenital fibrosarcoma/secretory breast carcinoma (t(12;15)(p13;q25)) (fusion of TEL and TrkC receptor), CML/ALL (t(9;12)(p24;p13)) (fusion of JAK and TEL), ALL (t(12;21)(p12;q22)) (fusion of TEL and AML1), MALT lymphoma (t(11;18)(q21;q21)) (fusion of BCL-2 and MLT), schizophrenia (t(1;11)(q42.1;q14.3)), anaplastic large cell lymphoma (t(2;5)(p23;q35)), Ewing's sarcoma (t(11;22) (q24;q11.2-12)), DFSP (t17;22)) (fusion of collagen I and platelet derived growth factor B), acute myelogenous leukemia (t1;12)(q21;p13)), synovial sarcoma (t(X;18)(p11.2; q11.2)), oligodendroglioma/oligoastrocytoma (t(1;19)(q10; p10)), ALL (t17;19)(q22;p13)), low-grade fibromyxoid sarcoma (t(7,16) (q32-34;p11) or t(11,16) (p11;p11)) (fusion of FUS and CREB3L2 or CREB3L1). Additional examples of chromosomal translocation-based conditions include, but are not limited to, those shown in Table 3.

In some embodiments, the methods of the present invention are used for determining if a subject (e.g., a human patient) is afflicted with ALK-positive anaplastic large cell lymphoma (ALCL) through quantifying and/or detecting the presence of NPM-ALK fusion protein expression within a biological sample (e.g., a blood sample) from the subject (e.g., through quantifying and/or detecting the presence of a fusion peptide having an amino acid sequence that spans the fusion junction encoded by a fusion of NPM nucleic acid (e.g., gene) to ALK nucleic acid (e.g., gene)). In some embodiments, such a fusion peptide comprises the following amino acid sequence: CGSGPVHISGQHLVVYR (SEQ ID NO: 1) (e.g., generated through digestion of an NPM-ALK fusion protein with a trypsin protease). In some embodiments, the presence of NPM-ALK fusion protein with a biological sample corresponds with a t(2;5)(p23;q35) cytogenetic abnormality.

Similarly, in some embodiments, the methods of the present invention are used for determining if a subject (e.g., a human subject) is afflicted with chronic myeloid leukemia or B-cell acute lymphoblastic leukemia through quantifying and/or detecting the presence of BCR-ABL1 (E13a2) fusion protein expression within a biological sample (e.g., a blood sample) from the subject (e.g., through quantifying and/or detecting the presence of a fusion peptide having an amino acid sequence that spans the fusion junction encoded by a fusion of BCR nucleic acid (e.g., gene) to ABL1 (E13a2) nucleic acid (e.g., gene)) (e.g., through quantifying and/or detecting the presence of a fusion peptide having an amino acid sequence specific for a sequential portion of the BCR-ABL1 (E13a2) fusion protein amino acid sequence encoded from the BCR gene and encoded from ABL1 (E13a2) gene within the biological sample). In some embodiments, such a fusion peptide comprises the following amino acid sequence: TINKEEAL (e.g., generated through digestion of BCR-ABL1 (E13a2) fusion protein with a chymotrypsin protease). In some embodiments, the presence of BCR-ABL1 (E13a2) fusion protein with a biological sample corresponds with a (9;22)(q34;q11.2) cytogenetic abnormality.

In some embodiments, the methods of the present invention are used for determining if a subject (e.g., a human subject) is afflicted with chronic myeloid leukemia or B-cell acute lymphoblastic leukemia through quantifying and/or detecting the presence of BCR-ABL1 (E1a2) fusion protein expression within a biological sample (e.g., a blood sample) from the subject (e.g., through quantifying and/or detecting the presence of a fusion peptide having an amino acid sequence that spans the fusion junction encoded by a fusion of BCR nucleic acid (e.g., gene) to ABL1 (E1a2) nucleic acid (e.g., gene)). In some embodiments, such a fusion peptide comprises the following amino acid sequence: HGDAEAL (SEQ ID NO: 3) (e.g., generated through digestion of BCR-ABL1 (E1a2) fusion protein with a chymotrypsin protease). In some embodiments, the presence of BCR-ABL1 (E1a2) fusion protein with a biological sample corresponds with a t(9;22)(q34;q11.2) cytogenetic abnormality.

In some embodiments, the methods of the present invention are used for determining if a subject (e.g., a human subject) is afflicted with mucosa associated lymphoid tissue (MALT) lymphoma through detecting the presence of API2-MALT1 (ex7-ex5) fusion protein expression within a biological sample (e.g., a blood sample) from the subject (e.g., through quantifying and/or detecting the presence of a fusion peptide having an amino acid sequence that spans the fusion junction encoded by a fusion of API2 nucleic acid (e.g., gene) to MALT1 (ex7-ex5) nucleic acid (e.g., gene)). In some embodiments, such a fusion peptide comprises the following amino acid sequence: SRSVDGVSE (e.g., generated through digestion of API2-MALT1 (ex7-ex5) fusion protein with a V8-DE protease). In some embodiments, such a fusion peptide comprises the following amino acid sequence: ESRSVDGVSESK (e.g., generated through digestion of API2-MALT1 (ex7-ex5) fusion protein with a Lys-C protease). In some embodiments, the presence of API2-MALT1 (ex7-ex5) fusion protein with a biological sample corresponds with a t(11;18)(q21;q21) cytogenetic abnormality.

In some embodiments, the methods of the present invention are used for determining if a subject (e.g., a human subject) is afflicted with mucosa associated lymphoid tissue (MALT) lymphoma through detecting the presence of API2-MALT1 (ex7-ex8) fusion protein expression within a biological sample (e.g., a blood sample) from the subject (e.g., through quantifying and/or detecting the presence of a fusion peptide having an amino acid sequence that spans the fusion junction encoded by a fusion of API2 nucleic acid (e.g., gene) to MALT1 (ex7-ex8) nucleic acid (e.g., gene)). In some embodiments, such a fusion peptide comprises the following amino acid sequence: ESNELNNLGHPDNK (SEQ ID NO: 6) (e.g., generated through digestion of API2-MALT1 (ex7-ex8) fusion protein with a trypsin protease). In some embodiments, the presence of API2-MALT1 (ex7-ex8) fusion protein with a biological sample corresponds with a t(11;18) (q21;q21) cytogenetic abnormality.

In some embodiments, the methods of the present invention are used for determining if a subject (e.g., a human subject) is afflicted with ALK-positive ALCL through quantifying and/or detecting the presence of TPM3-ALK fusion protein expression within a biological sample (e.g., a blood sample) from the subject (e.g., through quantifying and/or detecting the presence of a fusion peptide having an amino acid sequence that spans the fusion junction encoded by a fusion of TPM3 nucleic acid to ALK nucleic acid). In some embodiments, such a fusion peptide comprises the following amino acid sequence: TIDDLEVYR (e.g., generated through digestion of TPM3-ALK fusion protein with a trypsin protease). In some embodiments, the presence of TPM3-ALK fusion protein with a biological sample corresponds with a t(1;2)(q25;p23) cytogenetic abnormality.

In some embodiments, the methods of the present invention are used for determining if a subject (e.g., a human subject) is afflicted with ALK-positive diffuse large B-cell lymphoma (DLBCL) or ALCL through quantifying and/or detecting the presence of CLTC-ALK fusion protein expression within a biological sample (e.g., a blood sample) from the subject (e.g., through quantifying and/or detecting the presence of a fusion peptide having an amino acid sequence that spans the fusion junction encoded by a fusion of CLTC nucleic acid to ALK nucleic acid). In some embodiments, such a fusion peptide comprises the following amino acid sequence: LPGHVAADHPPAVYR (SEQ ID NO: 26) (e.g., generated through digestion of CLTC-ALK fusion protein with a trypsin protease). In some embodiments, the presence of CLTC-ALK fusion protein with a biological sample corresponds with a t(2;17)(p23;q23) cytogenetic abnormality.

In some embodiments, the methods of the present invention are used for determining if a subject (e.g., a human subject) is afflicted with ALK-positive DLBCL through quantifying and/or detecting the presence of SQSTM1-ALK fusion protein expression within a biological sample (e.g., a blood sample) from the subject (e.g., through quantifying and/or detecting the presence of a fusion peptide having an amino acid sequence that spans the fusion junction encoded by a fusion of SQSTM1 nucleic acid to ALK nucleic acid). In some embodiments, such a fusion peptide comprises the following amino acid sequence: NVGESVAAALSPLVYR (SEQ ID NO: 8) (e.g., generated through digestion of SQSTM1-ALK fusion protein with a trypsin protease). In some embodiments, the presence of SQSTM1-ALK fusion protein with a biological sample corresponds with a t(2;5)(p23;q35) cytogenetic abnormality.

In some embodiments, the methods of the present invention are used for determining if a subject (e.g., a human subject) is afflicted with biphenotypic acute lymphoblastic leukemia or B-cell acute lymphoblastic leukemia through quantifying and/or detecting the presence of MLL-AF4 fusion protein expression within a biological sample (e.g., a blood sample) from the subject (e.g., through quantifying and/or detecting the presence of a fusion peptide having an amino acid sequence that spans the fusion junction encoded by a fusion of MLL nucleic acid to AF4 nucleic acid). In some embodiments, such a fusion peptide comprises the following amino acid sequence: FKQTYSNE (SEQ ID NO: 9) (e.g., generated through digestion of MLL-AF4 fusion protein with a V8-DE protease). In some embodiments, the presence of MLL-AF4 fusion protein with a biological sample corresponds with a t(4;11)(q21;23) cytogenetic abnormality.

In some embodiments, the methods of the present invention are used for determining if a subject (e.g., a human subject) is afflicted with acute myeloid leukemia (AML) through quantifying and/or detecting the presence of MLL-AF9 fusion protein expression within a biological sample (e.g., a blood sample) from the subject (e.g., through quantifying and/or detecting the presence of a fusion peptide having an amino acid sequence that spans the fusion junction encoded by a fusion of MLL nucleic acid to AF9 nucleic acid). In some embodiments, such a fusion peptide comprises the following amino acid sequence: SDFVYCQVCCEPFHK (SEQ ID NO: 10) (e.g., generated through digestion of MLL-AF9 fusion protein with a trypsin protease). In some embodiments, the presence of MLL-AF9 fusion protein with a biological sample corresponds with a t(9;11)(p22;q23) cytogenetic abnormality.

In some embodiments, the methods of the present invention are used for determining if a subject (e.g., a human subject) is afflicted with AML through quantifying and/or detecting the presence of AML1-MTG8 fusion protein expression within a biological sample (e.g., a blood sample) from the subject (e.g., through quantifying and/or detecting the presence of a fusion peptide having an amino acid sequence that spans the fusion junction encoded by a fusion of AML1 nucleic acid to MTG8 nucleic acid). In some embodiments, such a fusion peptide comprises the following amino acid sequence: ITVDGPREPRNRTEK (SEQ ID NO: 11) (e.g., generated through digestion of MLL-AF9 fusion protein with a Lys-C protease). In some embodiments, the presence of AML1-MTG8 fusion protein with a biological sample corresponds with a t(8;21)(q22;q22) cytogenetic abnormality.

In some embodiments, the methods of the present invention are used for determining if a subject (e.g., a human subject) is afflicted with AML through quantifying and/or detecting the presence of NUP98-HOXD13 fusion protein expression within a biological sample (e.g., a blood sample) from the subject (e.g., through quantifying and/or detecting the presence of a fusion peptide having an amino acid sequence that spans the fusion junction encoded by a fusion of NUP98 nucleic acid to HOXD13). In some embodiments, such a fusion peptide comprises the following amino acid sequence: GAPQAPVGDVAL (SEQ ID NO: 12) (e.g., generated through digestion of NUP98-HOXD13 fusion protein with a chymotrypsin protease). In some embodiments, the presence of NUP98-HOXD13 fusion protein with a biological sample corresponds with a t(2;11)(q31;p15) cytogenetic abnormality.

In some embodiments, the methods of the present invention are used for determining if a subject (e.g., a human subject) is afflicted with AML through quantifying and/or detecting the presence of MLL-ELL fusion protein expression within a biological sample (e.g., a blood sample) from the subject (e.g., through quantifying and/or detecting the presence of a fusion peptide having an amino acid sequence that spans the fusion junction encoded by a fusion of MLL nucleic acid to ELL nucleic acid). In some embodiments, such a fusion peptide comprises the following amino acid sequence: VDFKDSVSLR (SEQ ID NO: 13) (e.g., generated through digestion of MLL-ELL fusion protein with a Arg-C protease). In some embodiments, the presence of MLL-ELL fusion protein with a biological sample corresponds with a t(11;19)(q23;p13.3) cytogenetic abnormality.

In some embodiments, the methods of the present invention are used for determining if a subject (e.g., a human subject) is afflicted with acute promyelocytic leukemia through quantifying and/or detecting the presence of PML-RARA fusion protein expression within a biological sample (e.g., a blood sample) from the subject (e.g., through quantifying and/or detecting the presence of a fusion peptide having an amino acid sequence that spans the fusion junction encoded by a fusion of PML nucleic acid to RARA nucleic acid). In some embodiments, such a fusion peptide comprises the following amino acid sequence: LSSCITQGKAIE (SEQ ID NO: 14) (e.g., generated through digestion of PML-RARA fusion protein with a V8-DE protease). In some embodiments, the presence of PML-RARA fusion protein with a biological sample corresponds with a t(15;17)(q22;q21) cytogenetic abnormality.

In some embodiments, the methods of the present invention are used for determining if a subject (e.g., a human subject) is afflicted with non-small cell lung cancer (NSCLC) through quantifying and/or detecting the presence of EML4-ALK (variant 1, 2 or 3a) fusion protein expression within a biological sample (e.g., a blood sample) from the subject (e.g., through quantifying and/or detecting the presence of a fusion peptide having an amino acid sequence that spans the fusion junction encoded by a fusion of EML4 nucleic acid to ALK (variant 1, 2 or 3a) nucleic acid). In some embodiments, such a fusion peptide comprises the following amino acid sequence: PTPGKGPKVYRRKHQE (SEQ ID NO: 15) (e.g., generated through digestion of EML4-ALK (variant 1) fusion protein with a V8-DE protease). In some embodiments, such a fusion peptide comprises the following amino acid sequence: YIMSNSGDYEILYLYR (SEQ ID NO: 16) (e.g., generated through digestion of EML4-ALK (variant 2) fusion protein with a trypsin protease). In some embodiments, such a fusion peptide comprises the following amino acid sequence: KNSQVYRRKHQE (SEQ ID NO: 17) (e.g., generated through digestion of EML4-ALK (variant 3a) fusion protein with a V8-DE protease). In some embodiments, the presence of EML4-ALK (variant 1, 2 or 3a) fusion protein with a biological sample corresponds with a inv(2)(p21;p23) cytogenetic abnormality.

In some embodiments, the methods of the present invention are used for determining if a subject (e.g., a human subject) is afflicted with papillary thyroid carcinoma through quantifying and/or detecting the presence of AKAP9-BRAF fusion protein expression within a biological sample (e.g., a blood sample) from the subject (e.g., through quantifying and/or detecting the presence of a fusion peptide having an amino acid sequence that spans the fusion junction encoded by a fusion of AKAP9 nucleic acid to BRAF nucleic acid). In some embodiments, such a fusion peptide comprises the following amino acid sequence: SEQDLIR (SEQ ID NO: 18) (e.g., generated through digestion of AKAP9-BRAF fusion protein with a trypsin protease). In some embodiments, the presence of AKAP9-BRAF fusion protein with a biological sample corresponds with a inv(7)(q21;q34) cytogenetic abnormality.

In some embodiments, the methods of the present invention are used for determining if a subject (e.g., a human subject) is afflicted with synovial sarcoma through quantifying and/or detecting the presence of SYT-SSX1 or SYT-SSX2 fusion protein expression within a biological sample (e.g., a blood sample) from the subject (e.g., through quantifying and/or detecting the presence of a fusion peptide having an amino acid sequence that spans the fusion junction encoded by a fusion of SYT nucleic acid to SSX1 nucleic acid or SYT nucleic acid to SSX2 nucleic acid). In some embodiments, such a fusion peptide comprises the following amino acid sequence: QIMPKKPAE (SEQ ID NO: 19) (e.g., generated through digestion of SYT-SSX1 or SYT-SSX2 fusion protein with a V8-DE protease). In some embodiments, the presence of SYT-SSX1 or SYT-SSX2 fusion protein with a biological sample corresponds with a t(X;18)(p11.2;q11.2) cytogenetic abnormality.

In some embodiments, the methods of the present invention are used for determining if a subject (e.g., a human subject) is afflicted with Ewing sarcoma through quantifying and/or detecting the presence of EWSR1-ERG fusion protein expression within a biological sample (e.g., a blood sample) from the subject (e.g., through quantifying and/or detecting the presence of a fusion peptide having an amino acid sequence that spans the fusion junction encoded by a fusion of EWSR1 nucleic acid to ERG nucleic acid). In some embodiments, such a fusion peptide comprises the following amino acid sequence: GQQSSGQIQL (SEQ ID NO: 20) (e.g., generated through digestion of EWSR1-ERG fusion protein with a chymotrypsin protease). In some embodiments, the presence of EWSR1-ERG fusion protein with a biological sample corresponds with a t(21;22)(q21;q12) cytogenetic abnormality.

In some embodiments, the methods of the present invention are used for determining if a subject (e.g., a human subject) is afflicted with alveolar rhabdomyosarcoma through quantifying and/or detecting the presence of PAX3-FOXO1 fusion protein expression within a biological sample (e.g., a blood sample) from the subject (e.g., through quantifying and/or detecting the presence of a fusion peptide having an amino acid sequence that spans the fusion junction encoded by a fusion of PAX3 nucleic acid to FOXO1 nucleic acid). In some embodiments, such a fusion peptide comprises the following amino acid sequence: SPQNSIRHNL (SEQ ID NO: 21) (e.g., generated through digestion of PAX3-FOXO1 fusion protein with a chymotrypsin protease). In some embodiments, the presence of PAX3-FOXO1 fusion protein with a biological sample corresponds with a t(2;13)(q35;q14) cytogenetic abnormality.

In some embodiments, the methods of the present invention are used for determining if a subject (e.g., a human subject) is afflicted with desmoplastic small round cell tumor through quantifying and/or detecting the presence of EWS/WT1 fusion protein expression within a biological sample (e.g., a blood sample) from the subject (e.g., through quantifying and/or detecting the presence of a fusion peptide having an amino acid sequence that spans the fusion junction encoded by a fusion of EWS nucleic acid to WT1 nucleic acid). In some embodiments, such a fusion peptide comprises the following amino acid sequence: GQQSEKPY (SEQ ID NO: 22) (e.g., generated through digestion of EWS/WT1 fusion protein with a chymotrypsin protease). In some embodiments, the presence of EWS/WT1 fusion protein with a biological sample corresponds with a t(11;22)(p13;q12) cytogenetic abnormality.

In some embodiments, the methods of the present invention are used for determining if a subject (e.g., a human subject) is afflicted with clear cell sarcoma through quantifying and/or detecting the presence of EWSR1/ATF1 (fusion type 1 or 2) fusion protein expression within a biological sample (e.g., a blood sample) from the subject (e.g., through quantifying and/or detecting the presence of a fusion peptide having an amino acid sequence that spans the fusion junction encoded by a fusion of EWSR1 nucleic acid to ATF1 (fusion type 1 or 2) nucleic acid). In some embodiments, such a fusion peptide comprises the following amino acid sequence: GGMGKILKDLSSEDTR (SEQ ID NO: 23) (e.g., generated through digestion of EWSR1/ATF1 (fusion type 1) fusion protein with a Arg-C protease). In some embodiments, such a fusion peptide comprises the following amino acid sequence: GQQIAIAPNGAL (SEQ ID NO: 24) (e.g., generated through digestion of EWSR1/ATF1 (fusion type 2) fusion protein with a chymotrypsin protease). In some embodiments, the presence of EWSR1/ATF1 (fusion type 1 or 2) fusion protein with a biological sample corresponds with a t(12;22)(a13;q12) cytogenetic abnormality.

In some embodiments, the methods of the present invention are used for determining if a subject (e.g., a human subject) is afflicted with dermatofibrosarcoma protuberans through quantifying and/or detecting the presence of COL1A1-PDGFB fusion protein expression within a biological sample (e.g., a blood sample) from the subject (e.g., through quantifying and/or detecting the presence of a fusion peptide having an amino acid sequence that spans the fusion junction encoded by a fusion of COL1A1 nucleic acid to PDGFB nucleic acid). In some embodiments, such a fusion peptide comprises the following amino acid sequence: QGPSGASGPAGPRGD (SEQ ID NO: 25) (e.g., generated through digestion of COL1A1-PDGFB fusion protein with a V8-DE protease). In some embodiments, the presence of COL1A1-PDGFB fusion protein with a biological sample corresponds with a t(17;22)(q22;q13) cytogenetic abnormality.

The methods are not limited to detecting a particular number of fusion proteins within a biological sample. For example, in some embodiments, multiple types of different fusion proteins can be simultaneously detected within a biological sample. For example, the methods of the present invention may be used to screen a biological sample from a subject (e.g., a human subject) for the presence of one or more (e.g., screening for the presence of 1, 2, 3, 5, 10, 15, 20, 50, etc.) fusion proteins associated with chromosomal translocation-based conditions. The results of such a screen can then be used to assist a health professional in caring and/or treating such a subject.

In some embodiments, detection of a fusion protein associated with a chromosomal translocation-based condition may be used as a means for assessing the efficacy of a particular treatment for such a chromosomal translocation-based condition. For example, in some embodiments, detecting a quantity change between time points for a fusion protein with a subject's biological sample can be used in assessing the efficacy of a particular treatment. Similarly, in some embodiments, the methods may be used for monitoring a therapy, predicting a response to therapy, and/or detecting minimal residual disease and/or prognosis of disease of a subject (e.g., a human patient). For example, in some embodiments, the methods of the present invention may be used in monitoring a therapy in a subject (e.g., a human patient) having one or more cells with fusion protein expression. In monitoring treatment or progression of a disease, samples may be obtained from the subject (e.g., human patient) at different timepoints, such as before, during, and/or after a therapy for a disease (e.g., cancer). In some embodiments, the detected presence of a particular fusion or the quantified amount of fusion protein expression from a biological sample of the subject are compared to their respective counterparts obtained at a different timepoint. Detected differences is correlated to success of the therapy and/or progression of the disease.

Additional Embodiments of the Present Invention

Additional embodiments of the present invention include, but are not limited to, the following:
1. A method for detecting the presence of a fusion protein within a biological sample, comprising:
   a) providing:
      a biological sample,
      labeled peptides having an amino acid sequence that spans the fusion junction of a fusion protein encoded by a fusion of a first nucleic acid to a second nucleic acid, wherein said labeled peptides comprise peptides having one isotopically labeled amino acid residue and peptides having two isotopically labeled amino acid residues, wherein said amino acid sequence of said labeled peptides is identical with an amino acid sequence of a fusion protein peptide fragment generated through digestion of said fusion protein with a protease, wherein said protease is known to generate upon digestion of said fusion protein a fusion protein peptide fragment having an amino acid sequence identical with said labeled peptides,
   b) digesting said biological sample with said protease resulting in generation of biological sample-based peptide fragments,
   c) combining said labeled peptides with said generated biological sample-based peptide fragments,
   d) purifying said labeled peptides combined with said generated biological sample-based peptide fragments,
   e) conducting a multiple reaction monitoring mass-spectrometry (MRM-MS) analysis of said purified biological sample-based peptide fragments combined with said labeled peptides, and
   f) analyzing the results of said MRM-MS analysis, wherein said analyzing comprises detecting the presence or absence of a biological sample-based fusion protein peptide fragment having an amino acid sequence identical with said labeled peptides,
   wherein detected co-elution of
      i) a biological sample-based fusion protein peptide fragment having an amino acid sequence identical with said labeled peptides, and
      ii) said labeled peptides,
   indicates the presence of said fusion protein within said biological sample.
2. The method of claim 1, wherein said protease is selected from the group consisting of trypsin, chymotrypsin, V8-DE, Lys-C, and Arg-C.
3. The method of claim 1, wherein said biological sample is a blood sample and/or a tissue sample.
4. The method of claim 1, wherein said levels of fusion protein within said biological sample are approximately 0.4 fmole μL (222 fmoles/mg lysate) or higher.
5. The method of claim 1, wherein said fusion protein encoded by a fusion of a first nucleic acid to a second nucleic acid is the result of a chromosomal translocation or a splice variation.
6. The method of claim 1, wherein said biological sample is from a human subject.
7. The method of claim 6, wherein said human subject is suspected of having a chromosomal translocation-based condition.
8. The method of claim 7, wherein said chromosomal-translocation based condition is an oncogenic disorder.
9. The method of claim 1, wherein said MRM-MS is conducted with a triple quadrupole mass spectrometer.
10. The method of claim 1, wherein said fusion protein, protease and amino acid sequence of said labeled peptides is selected from the group consisting of
NPM-ALK, trypsin, CGSGPVHISGQHLVVYR (SEQ ID NO: 1);
BCR-ABL1 (E13a2), chymotrypsin, TINKEEAL (SEQ ID NO: 2);
BCR-ABL1 (E1a2), chymotrypsin, HGDAEAL (SEQ ID NO: 3);
API2-MALT1 (ex7-ex5), V8-DE, SRSVDGVSE (SEQ ID NO: 4);
API2-MALT1 (ex7-ex8), Lys-C, ESRSVDGVSESK (SEQ ID NO: 35);
TPM3-ALK, trypsin, ESNELNNLGHPDNK (SEQ ID NO: 6);
CLTC-ALK, trypsin, TIDDLEVYR (SEQ ID NO: 7);
SQSTM1-ALK, trypsin, NVGESVAAALSPLVYR (SEQ ID NO: 8);
MLL-AF4, V8-DE, FKQTYSNE (SEQ ID NO: 9);
MLL-AF9, trypsin, SDFVYCQVCCEPFHK (SEQ ID NO: 10);
AML1-MTG8, Lys-C, ITVDGPREPRNRTEK (SEQ ID NO: 11);
NUP98-HOXD13, chymotrypsin, GAPQAPVGDVAL (SEQ ID NO: 12);
MLL-ELL, Arg-C, VDFKDSVSLR(SEQ ID NO: 13);
PML-RARA, V8-DE, LSSCITQGKAIE (SEQ ID NO: 14);
EML4-ALK (variant 1), V8-DE, PTPGKGPKVYRRKHQE (SEQ ID NO: 15);

EML4-ALK (variant 2), trypsin, YIMSNSGDYEILYLYR (SEQ ID NO:16);
EML4-ALK (variant 3a), V8-DE, KNSQVYRRKHQE (SEQ ID NO: 17);
AKAP9-BRAF, trypsin, SEQDLIR (SEQ ID NO: 18);
SYT-SSX1, V8-DE, QIMPKKPAE (SEQ ID NO: 19);
SYT-SSX2, V8-DE, QIMPKKPAE (SEQ ID NO: 19);
EWSR1-ERG, chymotrypsin, GQQSSGQIQL (SEQ ID NO: 22);
PAX3-FOXO1, chymotrypsin, SPQNSIRHNL (SEQ ID NO: 21);
EWS/WT1, chymotrypsin, GQQSEKPY(SEQ ID NO: 22);
EWSR1/ATF1 (fusion type 1), Arg-C, GGMGKILKDLSSEDTR (SEQ ID NO: 23);
EWSR1/ATF1 (fusion type 2), chymotrypsin, GQQIAIAPNGAL (SEQ ID NO: 24); and
COL1A1-PDGFB, V8-DE, QGPSGASGPAGPRGD (SEQ ID NO: 25).

11. The method of claim 10, wherein the detected presence of:
NPM-ALK fusion protein corresponds with a t(2;5)(p23; q35) cytogenetic abnormality;
BCR-ABL1 (E13a2) fusion protein corresponds with a (9;22) (q34;q11.2) cytogenetic abnormality;
BCR-ABL1 (E1a2) fusion protein corresponds with a t(9;22) (q34;q11.2) cytogenetic abnormality;
API2-MALT1 (ex7-ex5) fusion protein corresponds with a t(11;18)(q21;q21) cytogenetic abnormality;
API2-MALT1 (ex7-ex8) fusion protein corresponds with a t(11;18)(q21;q21) cytogenetic abnormality;
TPM3-ALK fusion protein corresponds with a t(1;2)(q25; p23) cytogenetic abnormality;
CLTC-ALK fusion protein corresponds with a t(2;17)(p23; q23) cytogenetic abnormality;
SQSTM1-ALK fusion protein corresponds with a t(2;5)(p23; q35) cytogenetic abnormality;
MLL-AF4 fusion protein corresponds with a t(4;11)(q21;23) cytogenetic abnormality;
MLL-AF9 fusion protein corresponds with a t(9;11)(p22; q23) cytogenetic abnormality;
AML1-MTG8 fusion protein corresponds with a t(8;21)(q22; q22) cytogenetic abnormality;
NUP98-HOXD13 fusion protein corresponds with a t(2;11) (q31;p15) cytogenetic abnormality;
MLL-ELL fusion protein corresponds with a t(11;19)(q23; p13.3) cytogenetic abnormality;
PML-RARA fusion protein corresponds with a t(15;17)(q22; q21) cytogenetic abnormality;
EML4-ALK (variant 1, 2 or 3a) fusion protein corresponds with a inv(2)(p21;p23) cytogenetic abnormality;
AKAP9-BRAF fusion protein corresponds with a inv(7)(q21; q34) cytogenetic abnormality;
SYT-SSX1 or SYT-SSX2 fusion protein corresponds with a t(X;18)(p11.2;q11.2) cytogenetic abnormality;
EWSR1-ERG fusion protein corresponds with a t(21;22) (q21;q12) cytogenetic abnormality;
PAX3-FOXO1 fusion protein corresponds with a t(2;13) (q35;q14) cytogenetic abnormality;
EWS/WT1 fusion protein corresponds with a t(11;22)(p13; q12) cytogenetic abnormality;
EWSR1/ATF1 (fusion type 1 or 2) fusion protein corresponds with a t(12;22)(a13;q12) cytogenetic abnormality;
and COL1A1-PDGFB fusion protein corresponds with a t(17;22)(q22;q13) cytogenetic abnormality.

12. The method of claim 1, wherein said analyzing further comprises quantifying the amount of expression of said fusion protein within said biological sample.

13. A method for detecting the presence of a chromosomal translocation-based condition within a subject, comprising:
a) providing:
a biological sample from a subject,
labeled peptides having an amino acid sequence that spans the fusion junction of a fusion protein encoded by a fusion of a first nucleic acid to a second nucleic acid, wherein said labeled peptides comprise peptides having one isotopically labeled amino acid residue and peptides having two isotopically labeled amino acid residues, wherein said amino acid sequence of said labeled peptides is identical with an amino acid sequence of a fusion protein peptide fragment generated through digestion of said fusion protein with a protease, wherein said protease is known to generate upon digestion of said fusion protein a fusion protein peptide fragment having an amino acid sequence identical with said labeled peptides,
b) digesting said biological sample with said protease resulting in generation of biological sample-based peptide fragments,
c) combining said labeled peptides with said generated biological sample-based peptide fragments,
d) purifying said labeled peptides combined with said generated biological sample-based peptide fragments,
e) conducting a multiple reaction monitoring mass-spectrometry (MRM-MS) analysis of said purified biological sample-based peptide fragments combined with said labeled peptides, and
f) analyzing the results of said MRM-MS analysis, wherein said analyzing comprises detecting the presence or absence of a biological sample-based fusion protein peptide fragment having an amino acid sequence identical with said labeled peptides
wherein detected co-elution of
i) a biological sample-based fusion protein peptide fragment having an amino acid sequence identical with said labeled peptides, and
ii) said labeled peptides,
indicates the presence of said fusion protein within said biological sample,
wherein a detected presence of said fusion protein within said biological sample indicates the presence of said chromosomal translocation-based condition within said subject.

14. The method of claim 13, wherein said protease is selected from the group consisting of trypsin, chymotrypsin, V8-DE, Lys-C, and Arg-C.

15. The method of claim 13, wherein said subject is a human subject.

16. The method of claim 15, wherein said human subject is suspected of having a chromosomal translocation-based condition.

17. The method of claim 16, wherein said chromosomal translocation-based condition is an oncogenic disorder, wherein said fusion protein is an oncogenic fusion protein associated with a specific type of cancer.

18. The method of claim 13, wherein said levels of fusion protein within said biological sample are approximately 0.4 fmole μL (222 fmoles/mg lysate) or higher.

19. The method of claim 13, wherein said MRM-MS is conducted with a triple quadrupole mass spectrometer.

20. The method of claim 13, wherein said chromosomal translocation-based condition, fusion protein, protease and amino acid sequence of said labeled peptides is selected from the group consisting of
ALK-positive anaplastic large cell lymphoma, NPM-ALK, trypsin, CGSGPVHISGQHLVVYR (SEQ ID NO: 1);

chronic myeloid leukemia or B-cell acute lymphoblastic leukemia, BCR-ABL1 (E13a2), chymotrypsin, TINKEEAL (SEQ ID NO: 2);
chronic myeloid leukemia or B-cell acute lymphoblastic leukemia, BCR-ABL1 (E1a2), chymotrypsin, HGDAEAL (SEQ ID NO: 3);
mucosa associated lymphoid tissue lymphoma, API2-MALT1 (ex7-ex5), V8-DE, SRSVDGVSE (SEQ ID NO: 4);
mucosa associated lymphoid tissue lymphoma; API2-MALT1 (ex7-ex8), Lys-C, ESRSVDGVSESK (SEQ ID NO: 5);
ALK-positive anaplastic large cell lymphoma, TPM3-ALK, trypsin, ESNELNNLGHPDNK (SEQ ID NO: 6);
ALK-positive diffuse large B-cell lymphoma or ALCL, CLTC-ALK, trypsin, TIDDLEVYR (SEQ ID NO: 7);
ALK-positive diffuse large B-cell lymphoma, SQSTM1-ALK, trypsin, NVGESVAAALSPLVYR (SEQ ID NO: 8);
biphenotypic acute lymphoblastic leukemia or B-cell acute lymphoblastic leukemia, MLL-AF4, V8-DE, FKQTYSNE (SEQ ID NO: 9);
acute myeloid leukemia, MLL-AF9, trypsin, SDFVYCQVCCEPFHK (SEQ ID NO: 10);
acute myeloid leukemia, AML1-MTG8, Lys-C, ITVDGPREPRNRTEK (SEQ ID NO: 11);
acute myeloid leukemia, NUP98-HOXD13, chymotrypsin, GAPQAPVGDVAL (SEQ ID NO: 36);
acute myeloid leukemia, MLL-ELL, Arg-C, VDFKDSVSLR (SEQ ID NO: 13);
acute promyelocytic leukemia, PML-RARA, V8-DE, LSSCITQGKAIE (SEQ ID NO: 14);
non-small cell lung cancer, EML4-ALK (variant 1), V8-DE, PTPGKGPKVYRRKHQE (SEQ ID NO: 15);
non-small cell lung cancer, EML4-ALK (variant 2), trypsin, YIMSNSGDYEILYLYR (SEQ ID NO: 16);
non-small cell lung cancer, EML4-ALK (variant 3a), V8-DE, KNSQVYRRKHQE (SEQ ID NO: 17);
papillary thyroid carcinoma, AKAP9-BRAF, trypsin, SEQDLIR (SEQ ID NO: 18);
synovial sarcoma, SYT-SSX1, V8-DE, QIMPKKPAE (SEQ ID NO: 19);
synovial sarcoma, SYT-SSX2, V8-DE, QIMPKKPAE (SEQ ID NO: 19);
Ewing sarcoma, EWSR1-ERG, chymotrypsin, GQQSSGQIQL (SEQ ID NO: 20);
alveolar rhabdomyosarcoma, PAX3-FOXO1, chymotrypsin, SPQNSIRHNL (SEQ ID NO: 21);
desmoplastic small round cell tumor, EWS/WT1, chymotrypsin, GQQSEKPY (SEQ ID NO: 22);
clear cell sarcoma, EWSR1/ATF1 (fusion type 1), Arg-C, GGMGKILKDLSSEDTR(SEQ ID NO: 23);
clear cell sarcoma, EWSR1/ATF1 (fusion type 2), chymotrypsin, GQQIAIAPNGAL (SEQ ID NO: 24); and
dermatofibrosarcoma protuberans, COL1A1-PDGFB, V8-DE, QGPSGASGPAGPRGD (SEQ ID NO: 25).

21. The method of claim 20, wherein the detected presence of:
NPM-ALK fusion protein corresponds with a t(2;5)(p23;q35) cytogenetic abnormality;
BCR-ABL1 (E13a2) fusion protein corresponds with a (9;22)(q34;q11.2) cytogenetic abnormality;
BCR-ABL1 (E1a2) fusion protein corresponds with a t(9;22)(q34;q11.2) cytogenetic abnormality;
API2-MALT1 (ex7-ex5) fusion protein corresponds with a t(11;18)(q21;q21) cytogenetic abnormality;
API2-MALT1 (ex7-ex8) fusion protein corresponds with a t(11;18)(q21;q21) cytogenetic abnormality;
TPM3-ALK fusion protein corresponds with a t(1;2)(q25;p23) cytogenetic abnormality;
CLTC-ALK fusion protein corresponds with a t(2;17)(p23;q23) cytogenetic abnormality;
SQSTM1-ALK fusion protein corresponds with a t(2;5)(p23;q35) cytogenetic abnormality;
MLL-AF4 fusion protein corresponds with a t(4;11)(q21;23) cytogenetic abnormality;
MLL-AF9 fusion protein corresponds with a t(9;11)(p22;q23) cytogenetic abnormality;
AML1-MTG8 fusion protein corresponds with a t(8;21)(q22;q22) cytogenetic abnormality;
NUP98-HOXD13 fusion protein corresponds with a t(2;11)(q31;p15) cytogenetic abnormality;
MLL-ELL fusion protein corresponds with a t(11;19)(q23;p13.3) cytogenetic abnormality;
PML-RARA fusion protein corresponds with a t(15;17)(q22;q21) cytogenetic abnormality;
EML4-ALK (variant 1, 2 or 3a) fusion protein corresponds with a inv(2)(p21;p23) cytogenetic abnormality;
AKAP9-BRAF fusion protein corresponds with a inv(7)(q21;q34) cytogenetic abnormality;
SYT-SSX1 or SYT-SSX2 fusion protein corresponds with a t(X;18)(p11.2;q11.2) cytogenetic abnormality;
EWSR1-ERG fusion protein corresponds with a t(21;22)(q21;q12) cytogenetic abnormality;
PAX3-FOXO1 fusion protein corresponds with a t(2;13)(q35;q14) cytogenetic abnormality;
EWS/WT1 fusion protein corresponds with a t(11;22)(p13;q12) cytogenetic abnormality;
EWSR1/ATF1 (fusion type 1 or 2) fusion protein corresponds with a t(12;22)(a13;q12) cytogenetic abnormality;
and COL1A1-PDGFB fusion protein corresponds with a t(17;22)(q22;q13) cytogenetic abnormality.

22. The method of claim 13, wherein said analyzing further comprises quantifying the amount of expression of said fusion protein within said biological sample.

23. The method of claim 22, wherein said quantified amount of expression of said fusion protein is compared with a quantified amount of expression of said fusion protein measured at an earlier time point.

24. A method for detecting the presence of two or more fusion proteins within a biological sample, comprising:
a) providing:
a biological sample,
two or more distinct groups of labeled peptides, wherein each distinct group of labeled peptides is specific for a particular fusion protein to be detected, wherein the labeled peptides within each distinct group have labeled peptides having an amino acid sequence that spans the fusion junction of said particular fusion protein encoded by a fusion of a first nucleic acid to a second nucleic acid,
wherein said labeled peptides within each group comprise peptides having one isotopically labeled amino acid residue and peptides having two isotopically labeled amino acid residues,
wherein said amino acid sequence of said labeled peptides within each distinct group is identical with an amino acid sequence of a particular fusion protein peptide fragment generated through digestion of said particular fusion protein with a protease,
a protease known to generate upon digestion of said two or more fusion proteins to be detected particular fusion protein peptide fragments,
b) digesting said biological sample with said protease resulting in generation of biological sample-based peptide fragments,
c) combining said groups of labeled peptides with said generated biological sample-based peptide fragments, d) purifying said labeled peptides combined with said generated biological sample-based peptide fragments, e) conducting a multiple reaction monitoring mass-spectrometry (MRM-MS) analysis of said purified biological sample-based peptide fragments combined with said labeled peptides, and f) analyzing the results of said MRM-MS analysis, wherein said analyzing comprises detecting the presence or absence of a biological sample-based fusion protein peptide fragment having an amino acid sequence identical with the amino acid sequence for one of the distinct groups of labeled peptides specific for a particular fusion protein, wherein detected co-elution of
  i) a biological sample-based fusion protein peptide fragment having an amino acid sequence identical with the amino acid sequence for one of the distinct groups of labeled peptides specific for a particular fusion protein, and
  ii) said amino acid sequence for one of the distinct groups of labeled peptides specific for a particular fusion protein,
indicates the presence of said particular fusion protein within said biological sample.

25. The method of claim 24, wherein a detected presence of a particular fusion protein within said biological sample indicates the presence of a chromosomal translocation-based condition associated with said particular fusion protein within said subject.

26. The method of claim 24, wherein said biological sample is a blood sample and/or a tissue sample.

27. The method of claim 24, wherein said levels of fusion protein within said biological sample are approximately 0.4 fmole μL (222 fmoles/mg lysate) or higher.

28. The method of claim 24, wherein said biological sample is from a human subject.

29. The method of claim 28, wherein said human subject is suspected of having a chromosomal translocation-based condition.

30. The method of claim 29, wherein said chromosomal-translocation based condition is an oncogenic disorder.

31. The method of claim 30, wherein said MRM-MS is conducted with a triple quadrupole mass spectrometer.

32. The method of claim 24, wherein said protease is trypsin, and wherein said two or more fusion proteins and amino acid sequence resulting from digestion with said protease are selected from the group consisting of:
NPM-ALK, CGSGPVHISGQHLVVYR (SEQ ID NO: 1);
TPM3-ALK, ESNELNNLGHPDNK (SEQ ID NO: 6);
CLTC-ALK, TIDDLEVYR (SEQ ID NO: 3);
SQSTM1-ALK, NVGESVAAALSPLVYR (SEQ ID NO: 8);
MLL-AF9, SDFVYCQVCCEPFHK (SEQ ID NO: 10);
EML4-ALK (variant 2), YIMSNSGDYEILYLYR (SEQ ID NO: 16);
EML4-ALK (variant 3a), V8-DE, KNSQVYRRKHQE (SEQ ID NO: 17); and
AKAP9-BRAF, SEQDLIR (SEQ ID NO: 18).

33. The method of claim 24, wherein said protease is chmotrypsin, and wherein said two or more fusion proteins and amino acid sequence resulting from digestion with said protease are selected from the group consisting of:
BCR-ABL1 (E13a2), TINKEEAL (SEQ ID NO: 2);
BCR-ABL1 (E1a2), HGDAEAL (SEQ ID NO: 3);
NUP98-HOXD13, GAPQAPVGDVAL (SEQ ID NO: 12);
EWSR1-ERG, GQQSSGQIQL (SEQ ID NO: 20);
PAX3-FOXO1, SPQNSIRHNL (SEQ ID NO: 21);
EWS/WT1, GQQSEKPY (SEQ ID NO: 22); and
EWSR1/ATF1 (fusion type 2), GQQIAIAPNGAL (SEQ ID NO: 24).

34. The method of claim 24, wherein said protease is Arg-C, and wherein said fusion proteins and amino acid sequences resulting from digestion with said protease are:
EWSR1/ATF1 (fusion type 1), GGMGKILKDLSSEDTR (SEQ ID NO: 23); and
MLL-ELL, VDFKDSVSLR (SEQ ID NO: 13).

35. The method of claim 23, wherein said protease is V8-DE, and wherein said two or more fusion proteins and amino acid sequence resulting from digestion with said protease are selected from the group consisting of:
COL1A1-PDGFB, QGPSGASGPAGPRGD (SEQ ID NO: 25).
API2-MALT1 (ex7-ex5), SRSVDGVSE (SEQ ID NO: 4);
PML-RARA, LSSCITQGKAIE (SEQ ID NO: 14);
EML4-ALK (variant 1), PTPGKGPKVYRRKHQE (SEQ ID NO: 15);
MLL-AF4, FKQTYSNE (SEQ ID NO: 9);
SYT-SSX1, QIMPKKPAE (SEQ ID NO: 19); and
SYT-SSX2, QIMPKKPAE (SEQ ID NO: 19).

36. The method of claim 24, wherein said protease is Lys-C, and wherein said fusion proteins and amino acid sequences resulting from digestion with said protease are:
API2-MALT1 (ex7-ex8), Lys-C, ESRSVDGVSESK (SEQ ID NO: 5); and
AML1-MTG8, Lys-C, ITVDGPREPRNRTEK (SEQ ID NO: 11).

37. The method of claims 33-36, wherein the detected presence of:
NPM-ALK fusion protein corresponds with a t(2;5)(p23;q35) cytogenetic abnormality;
BCR-ABL1 (E13a2) fusion protein corresponds with a (9;22)(q34;q11.2) cytogenetic abnormality;
BCR-ABL1 (E1a2) fusion protein corresponds with a t(9;22)(q34;q11.2) cytogenetic abnormality;
API2-MALT1 (ex7-ex5) fusion protein corresponds with a t(11;18)(q21;q21) cytogenetic abnormality;
API2-MALT1 (ex7-ex8) fusion protein corresponds with a t(11;18)(q21;q21) cytogenetic abnormality;
TPM3-ALK fusion protein corresponds with a t(1;2)(q25;p23) cytogenetic abnormality;
CLTC-ALK fusion protein corresponds with a t(2;17)(p23;q23) cytogenetic abnormality;
SQSTM1-ALK fusion protein corresponds with a t(2;5)(p23;q35) cytogenetic abnormality;
MLL-AF4 fusion protein corresponds with a t(4;11)(q21;23) cytogenetic abnormality;
MLL-AF9 fusion protein corresponds with a t(9;11)(p22;q23) cytogenetic abnormality;
AML1-MTG8 fusion protein corresponds with a t(8;21)(q22;q22) cytogenetic abnormality;
NUP98-HOXD13 fusion protein corresponds with a t(2;11)(q31;p15) cytogenetic abnormality;
MLL-ELL fusion protein corresponds with a t(11;19)(q23;p13.3) cytogenetic abnormality;
PML-RARA fusion protein corresponds with a t(15;17)(q22;q21) cytogenetic abnormality;
EML4-ALK (variant 1, 2 or 3a) fusion protein corresponds with a inv(2)(p21;p23) cytogenetic abnormality;
AKAP9-BRAF fusion protein corresponds with a inv(7)(q21;q34) cytogenetic abnormality;
SYT-SSX1 or SYT-SSX2 fusion protein corresponds with a t(X;18)(p11.2;q11.2) cytogenetic abnormality;
EWSR1-ERG fusion protein corresponds with a t(21;22)(q21;q12) cytogenetic abnormality;

PAX3-FOXO1 fusion protein corresponds with a t(2;13)(q35;q14) cytogenetic abnormality;
EWS/WT1 fusion protein corresponds with a t(11;22)(p13;q12) cytogenetic abnormality;
EWSR1/ATF1 (fusion type 1 or 2) fusion protein corresponds with a t(12;22)(a13;q12) cytogenetic abnormality;
and COL1A1-PDGFB fusion protein corresponds with a t(17;22)(q22;q13) cytogenetic abnormality.

38. The method of claim 24, wherein said analyzing further comprises quantifying the amount of expression of said fusion proteins within said biological sample.

39. A method for detecting the presence one or more chromosomal translocation-based conditions within a subject, comprising:
   a) providing:
      a biological sample from a subject,
      two or more distinct groups of labeled peptides, wherein each distinct group of labeled peptides is specific for a particular fusion protein to be detected, wherein the labeled peptides within each distinct group have labeled peptides having an amino acid sequence that spans the fusion junction of said particular fusion protein encoded by a fusion of a first nucleic acid to a second nucleic acid, wherein said labeled peptides within each group comprise peptides having one isotopically labeled amino acid residue and peptides having two isotopically labeled amino acid residues,
      wherein said amino acid sequence of said labeled peptides within each distinct group is identical with an amino acid sequence of a particular fusion protein peptide fragment generated through digestion of said particular fusion protein with a protease,
      a protease known to generate upon digestion of said two or more fusion proteins to be detected particular fusion protein peptide fragments,
   b) digesting said biological sample with said protease resulting in generation of biological sample-based peptide fragments,
   c) combining said groups of labeled peptides with said generated biological sample-based peptide fragments,
   d) purifying said labeled peptides combined with said generated biological sample-based peptide fragments,
   e) conducting a multiple reaction monitoring mass-spectrometry (MRM-MS) analysis of said purified biological sample-based peptide fragments combined with said labeled peptides, and
   f) analyzing the results of said MRM-MS analysis, wherein said analyzing comprises detecting the presence or absence of a biological sample-based fusion protein peptide fragment having an amino acid sequence identical with the amino acid sequence for one of the distinct groups of labeled peptides specific for a particular fusion protein,
   wherein detected co-elution of
      i) a biological sample-based fusion protein peptide fragment having an amino acid sequence identical with the amino acid sequence for one of the distinct groups of labeled peptides specific for a particular fusion protein, and
      ii) said amino acid sequence for one of the distinct groups of labeled peptides specific for a particular fusion protein,
   indicates the presence of said particular fusion protein within said biological sample,
   wherein a detected presence of said particular fusion protein within said biological sample indicates the presence of said chromosomal translocation-based condition within said subject.

40. The method of claim 39, wherein said subject is a human subject.

41. The method of claim 40, wherein said human subject is suspected of having a chromosomal translocation-based condition.

42. The method of claim 41, wherein said chromosomal translocation-based condition is an oncogenic disorder, wherein said fusion protein is an oncogenic fusion protein associated with a specific type of cancer.

43. The method of claim 39, wherein said levels of fusion protein within said biological sample are approximately 0.4 fmole μL (222 fmoles/mg lysate) or higher.

44. The method of claim 39, wherein said MRM-MS is conducted with a triple quadrupole mass spectrometer.

45. The method of claim 39, wherein said protease is trypsin, and wherein said chromosomal translocation-based condition, said two or more fusion proteins, and amino acid sequence resulting from digestion with said protease are selected from the group consisting of:
ALK-positive anaplastic large cell lymphoma, NPM-ALK, CGSGPVHISGQHLVVYR (SEQ ID NO: 1);
ALK-positive anaplastic large cell lymphoma, TPM3-ALK, ESNELNNLGHPDNK (SEQ ID NO: 5);
ALK-positive diffuse large B-cell lymphoma or ALCL, CLTC-ALK, TIDDLEVYR (SEQ ID NO: 7);
ALK-positive diffuse large B-cell lymphoma, SQSTM1-ALK, NVGESVAAALSPLVYR (SEQ ID NO: 8);
biphenotypic acute lymphoblastic leukemia or B-cell acute lymphoblastic leukemia, MLL-AF4, FKQTYSNE (SEQ ID NO: 9);
acute myeloid leukemia, MLL-AF9, SDFVYCQVCCEPFHK (SEQ ID NO: 10);
non-small cell lung cancer, EML4-ALK (variant 2), YIMSNSGDYEILYLYR (SEQ ID NO: 16); and
papillary thyroid carcinoma, AKAP9-BRAF, SEQDLIR (SEQ ID NO: 18);

46. The method of claim 39, wherein said protease is chymotrypsin, and wherein said chromosomal translocation-based condition, said two or more fusion proteins, and amino acid sequence resulting from digestion with said protease are selected from the group consisting of:
chronic myeloid leukemia or B-cell acute lymphoblastic leukemia, BCR-ABL1 (E13a2), TINKEEAL (SEQ ID NO: 2);
chronic myeloid leukemia or B-cell acute lymphoblastic leukemia, BCR-ABL1 (E1a2), HGDAEAL (SEQ ID NO: 3);
acute myeloid leukemia, NUP98-HOXD13, GAPQAPVGDVAL (SEQ ID NO: 12);
Ewing sarcoma, EWSR1-ERG, GQQSSGQIQL (SEQ ID NO: 20);
alveolar rhabdomyosarcoma, PAX3-FOXO1, SPQNSIRHNL (SEQ ID NO: 21);
clear cell sarcoma, EWSR1/ATF1 (fusion type 2), GQQIAIAPNGAL (SEQ ID NO: 24); and
desmoplastic small round cell tumor, EWS/WT1, GQQSEKPY (SEQ ID NO: 22);

47. The method of claim 39, wherein said protease is Arg-C, and wherein said chromosomal translocation-based condition, said fusion proteins, and amino acid sequence resulting from digestion with said protease are:
acute myeloid leukemia, MLL-ELL, VDFKDSVSLR (SEQ ID NO: 13); and
clear cell sarcoma, EWSR1/ATF1 (fusion type 1), GGMGKILKDLSSEDTR (SEQ ID NO: 23).

48. The method of claim 39, wherein said protease is V8-DE, and wherein said chromosomal translocation-based condition, said two or more fusion proteins, and amino acid sequence resulting from digestion with said protease are selected from the group consisting of:

dermatofibrosarcoma protuberans, COL1A1-PDGFB, QGPSGASGPAGPRGD (SEQ ID NO: 25).

acute promyelocytic leukemia, PML-RARA, LSSCITQG-KAIE (SEQ ID NO: 14); non-small cell lung cancer, EML4-ALK (variant 1), V8-DE, PTPGKGPKVYRRKHQE (SEQ ID NO: 15);

mucosa associated lymphoid tissue lymphoma, API2-MALT1 (ex7-ex5), SRSVDGVSE (SEQ ID NO: 4);

non-small cell lung cancer, EML4-ALK (variant 3a), KNSQVYRRKHQE (SEQ ID NO: 17);

synovial sarcoma, SYT-SSX1, QIMPKKPAE (SEQ ID NO: 19); and synovial sarcoma, SYT-SSX2, QIMPKKPAE (SEQ ID NO: 19).

49. The method of claim 39, wherein said protease is Lys-C, and wherein said chromosomal translocation-based condition, said fusion proteins, and amino acid sequence resulting from digestion with said protease are:

mucosa associated lymphoid tissue lymphoma; API2-MALT1 (ex7-ex8), ESRSVDGVSESK (SEQ ID NO: 5); and acute myeloid leukemia, AML1-MTG8, ITVDGPREPRN-RTEK (SEQ ID NO: 11).

50. The method of claims 45-49, wherein the detected presence of:

NPM-ALK fusion protein corresponds with a t(2;5)(p23;q35) cytogenetic abnormality;

BCR-ABL1 (E13a2) fusion protein corresponds with a (9;22)(q34;q11.2) cytogenetic abnormality;

BCR-ABL1 (E1a2) fusion protein corresponds with a t(9;22)(q34;q11.2) cytogenetic abnormality;

API2-MALT1 (ex7-ex5) fusion protein corresponds with a t(11;18)(q21;q21) cytogenetic abnormality;

API2-MALT1 (ex7-ex8) fusion protein corresponds with a t(11;18)(q21;q21) cytogenetic abnormality;

TPM3-ALK fusion protein corresponds with a t(1;2)(q25;p23) cytogenetic abnormality;

CLTC-ALK fusion protein corresponds with a t(2;17)(p23;q23) cytogenetic abnormality;

SQSTM1-ALK fusion protein corresponds with a t(2;5)(p23;q35) cytogenetic abnormality;

MLL-AF4 fusion protein corresponds with a t(4;11)(q21;q23) cytogenetic abnormality;

MLL-AF9 fusion protein corresponds with a t(9;11)(p22;q23) cytogenetic abnormality;

AML1-MTG8 fusion protein corresponds with a t(8;21)(q22;q22) cytogenetic abnormality;

NUP98-HOXD13 fusion protein corresponds with a t(2;11)(q31;p15) cytogenetic abnormality;

MLL-ELL fusion protein corresponds with a t(11;19)(q23;p13.3) cytogenetic abnormality;

PML-RARA fusion protein corresponds with a t(15;17)(q22;q21) cytogenetic abnormality;

EML4-ALK (variant 1, 2 or 3a) fusion protein corresponds with a inv(2)(p21;p23) cytogenetic abnormality;

AKAP9-BRAF fusion protein corresponds with a inv(7)(q21;q34) cytogenetic abnormality;

SYT-SSX1 or SYT-SSX2 fusion protein corresponds with a t(X;18)(p11.2;q11.2) cytogenetic abnormality;

EWSR1-ERG fusion protein corresponds with a t(21;22)(q21;q12) cytogenetic abnormality;

PAX3-FOXO1 fusion protein corresponds with a t(2;13)(q35;q14) cytogenetic abnormality;

EWS/WT1 fusion protein corresponds with a t(11;22)(p13;q12) cytogenetic abnormality;

EWSR1/ATF1 (fusion type 1 or 2) fusion protein corresponds with a t(12;22)(a13;q12) cytogenetic abnormality;

and COL1A1-PDGFB fusion protein corresponds with a t(17;22)(q22;q13) cytogenetic abnormality.

51. The method of claim 39, wherein said analyzing further comprises quantifying the amount of expression of said fusion protein within said biological sample.

52. The method of claim 51, wherein said quantified amount of expression of said fusion protein is compared with a quantified amount of expression of said fusion protein measured at an earlier time point.

53. A kit comprising:

labeled peptides having an amino acid sequence that spans the fusion junction of a fusion protein encoded by a fusion of a first nucleic acid to a second nucleic acid, wherein said labeled peptides comprise peptides having one isotopically labeled amino acid residue and peptides having two isotopically labeled amino acid residues, wherein said amino acid sequence of said labeled peptides is identical with an amino acid sequence of a fusion protein peptide fragment generated through digestion of said fusion protein with a protease, wherein said protease is known to generate upon digestion of said fusion protein a fusion protein peptide fragment having an amino acid sequence identical with said labeled peptides.

54. The method of claim 53, wherein said fusion protein, protease and amino acid sequence of said labeled peptides are selected from the group consisting of:

NPM-ALK, trypsin, CGSGPVHISGQHLVVYR (SEQ ID NO: 1);

BCR-ABL1 (E13a2), chymotrypsin, TINKEEAL (SEQ ID NO: 2);

BCR-ABL1 (E1a2), chymotrypsin, HGDAEAL (SEQ ID NO: 3);

API2-MALT1 (ex7-ex5), V8-DE, SRSVDGVSE (SEQ ID NO: 4);

API2-MALT1 (ex7-ex8), Lys-C, ESRSVDGVSESK (SEQ ID NO: 35);

TPM3-ALK, trypsin, ESNELNNLGHPDNK (SEQ ID NO: 6);

CLTC-ALK, trypsin, TIDDLEVYR (SEQ ID NO: 7);

SQSTM1-ALK, trypsin, NVGESVAAALSPLVYR (SEQ ID NO: 8);

MLL-AF4, V8-DE, FKQTYSNE (SEQ ID NO: 9);

MLL-AF9, trypsin, SDFVYCQVCCEPFHK (SEQ ID NO: 10);

AML1-MTG8, Lys-C, ITVDGPREPRNRTEK (SEQ ID NO: 11);

NUP98-HOXD13, chymotrypsin, GAPQAPVGDVAL (SEQ ID NO: 12);

MLL-ELL, Arg-C, VDFKDSVSLR (SEQ ID NO: 13);

PML-RARA, V8-DE, LSSCITQGKAIE (SEQ ID NO: 14);

EML4-ALK (variant 1), V8-DE, PTPGKGPKVYRRKHQE (SEQ ID NO: 15);

EML4-ALK (variant 2), trypsin, YIMSNSGDYEILYLYR (SEQ ID NO: 16);

EML4-ALK (variant 3a), V8-DE, KNSQVYRRKHQE (SEQ ID NO: 17);

AKAP9-BRAF, trypsin, SEQDLIR (SEQ ID NO: 18);

SYT-SSX1, V8-DE, QIMPKKPAE (SEQ ID NO: 19);

SYT-SSX2, V8-DE, QIMPKKPAE (SEQ ID NO: 19);

EWSR1-ERG, chymotrypsin, GQQSSGQIQL (SEQ ID NO: 22);

PAX3-FOXO1, chymotrypsin, SPQNSIRHNL (SEQ ID NO: 21);

EWS/WT1, chymotrypsin, GQQSEKPY (SEQ ID NO: 22);

EWSR1/ATF1 (fusion type 1), Arg-C, GGMGKILKDLSSEDTR (SEQ ID NO: 23);

EWSR1/ATF1 (fusion type 2), chymotrypsin, GQQIAIAPN-GAL (SEQ ID NO: 24); and
COL1A1-PDGFB, V8-DE, QGPSGASGPAGPRGD (SEQ ID NO: 25).

55. A kit comprising
two or more distinct groups of labeled peptides, wherein each distinct group of labeled peptides is specific for a particular fusion protein, wherein the labeled peptides within each distinct group have labeled peptides having an amino acid sequence that spans the fusion junction of said particular fusion protein encoded by a fusion of a first nucleic acid to a second nucleic acid, wherein said labeled peptides within each group comprise peptides having one isotopically labeled amino acid residue and peptides having two isotopically labeled amino acid residues, wherein said amino acid sequence of said labeled peptides within each distinct group is identical with an amino acid sequence of a particular fusion protein peptide fragment generated through digestion of said particular fusion protein with a protease, and
a protease known to generate upon digestion of said two or more fusion proteins to be detected particular fusion protein peptide fragments.

56. The kit of claim 55, wherein said fusion proteins, proteases and amino acid sequences of said labeled peptides are selected from the group consisting of
NPM-ALK, trypsin, CGSGPVHISGQHLVVYR (SEQ ID NO: 1);
BCR-ABL1 (E13a2), chymotrypsin, TINKEEAL (SEQ ID NO: 2);
BCR-ABL1 (E1a2), chymotrypsin, HGDAEAL (SEQ ID NO: 3);
API2-MALT1 (ex7-ex5), V8-DE, SRSVDGVSE (SEQ ID NO: 4);
API2-MALT1 (ex7-ex8), Lys-C, ESRSVDGVSESK (SEQ ID NO: 35);
TPM3-ALK, trypsin, ESNELNNLGHPDNK (SEQ ID NO: 6);
CLTC-ALK, trypsin, TIDDLEVYR (SEQ ID NO: 7);
SQSTM1-ALK, trypsin, NVGESVAAALSPLVYR (SEQ ID NO: 8);
MLL-AF4, V8-DE, FKQTYSNE (SEQ ID NO: 9);
MLL-AF9, trypsin, SDFVYCQVCCEPFHK (SEQ ID NO: 10);
AML1-MTG8, Lys-C, ITVDGPREPRNRTEK (SEQ ID NO: 11);
NUP98-HOXD13, chymotrypsin, GAPQAPVGDVAL (SEQ ID NO: 12);
MLL-ELL, Arg-C, VDFKDSVSLR (SEQ ID NO: 13);
PML-RARA, V8-DE, LSSCITQGKAIE (SEQ ID NO: 14);
EML4-ALK (variant 1), V8-DE, PTPGKGPKVYRRKHQE (SEQ ID NO: 15);
EML4-ALK (variant 2), trypsin, YIMSNSGDYEILYLR (SEQ ID NO:16);
EML4-ALK (variant 3a), V8-DE, KNSQVYRRKHQE (SEQ ID NO: 17);
AKAP9-BRAF, trypsin, SEQDLIR (SEQ ID NO: 18);
SYT-SSX1, V8-DE, QIMPKKPAE (SEQ ID NO: 19);
SYT-SSX2, V8-DE, QIMPKKPAE (SEQ ID NO: 19);
EWSR1-ERG, chymotrypsin, GQQSSGQIQL (SEQ ID NO: 22);
PAX3-FOXO1, chymotrypsin, SPQNSIRHNL (SEQ ID NO: 21);
EWS/WT1, chymotrypsin, GQQSEKPY(SEQ ID NO: 22);
EWSR1/ATF1 (fusion type 1), Arg-C, GGMGKILKDLSSEDTR (SEQ ID NO: 23);
EWSR1/ATF1 (fusion type 2), chymotrypsin, GQQIAIAPN-GAL (SEQ ID NO: 24); and
COL1A1-PDGFB, V8-DE, QGPSGASGPAGPRGD (SEQ ID NO: 25).

57. A method of monitoring a therapy for a chromosomal translocation-based condition comprising comparing quantified fusion protein levels at different time points with the method described in claim 1.

EXPERIMENTAL

The following example is provided in order to demonstrate and further illustrate certain preferred embodiments and aspects of the present invention and is not to be construed as limiting the scope thereof.

Example I

This example describes the materials and methods for Examples II-V.

Materials:

Peptides were purchased from Thermo Scientific. The NPM-ALK fusion peptide (CGSGPVHISGQHLVVYR (SEQ ID NO: 1)) was procured in 3 isotopically labeled forms—light (i.e. endogenous peptide), heavy in which C-terminal arginine was $^{13}C_6/^{15}N_4$ labeled and double heavy in which C-terminal Arginine $^{13}C_6/^{15}N_4$ and an internal valine $^{13}C_5/^{15}N$ were labeled. The N-terminal cysteine was carbamidomethylated for all three. Concentration was determined by amino acid analysis and purity was >97%. Two API2-MALT1 fusion peptides were synthesized ESRS-VDGVSESK (SEQ ID NO: 5) and SRSVDGVSE (SEQ ID NO: 4) (AQUA, purity>97%). BCR-ABL1 fusion peptides TINKEEAL (SEQ ID NO: 2) and HGDAEAL (SEQ ID NO: 3) were also synthesized (purity>95%) along with the heavy isotopically labeled forms in which the C-terminal leucine was $^{13}C_6/^{15}N$ labeled (AQUA, purity>97%). All other reagents were of the highest grade available.

Cell Lines:

A total of 9 cell lines derived from human T-cell lymphoproliferative disorders were cultured in RPMI supplemented with 10% of fetal bovine serum, 2.05 mM L-glutamine, 1,000 UI/mL penicillin, 1,000 µg/mL streptomycin and 2.5 µg/mL amphotericin B. Five cell lines derived from ALK-positive anaplastic large cell lymphoma were investigated and characterized by the chromosomal translocation t(2;5)(p23;q35): Karpas-299, SUP-M2, SR-786, SUD-HL-1 and DEL. Three cell lines derived from ALK-negative cutaneous T-cell lymphoma: Mac-1, Mac-2A, and HH, were also studied. Additionally, the cell line Jurkat which is representative of T-cell lymphoblastic leukemia was analyzed.

Clinical Samples:

In all, 23 clinical samples were included in this study. All samples were collected at the time of diagnosis before any treatment. Cells were stored in liquid nitrogen until further analysis. After three washes with cold PBS to remove cryopreservative solution, samples were processed the same as the cell lines.

Detection and Quantitation of NPM-ALK by Quantitative Real-Time Polymerase Chain Reaction:

Total RNA was extracted by TRIzol (Invitrogen) and subjected to reverse transcription using the SuperScript II Reverse Transcriptase (Invitrogen) according to the manufacturer's instructions. Quantitative real-time polymerase chain reaction was performed with the Mastercycler® ep realplex thermal cycler (Eppendorf). The expression levels of NPM-ALK RNA were determined using TaqMan probe-based assay (forward primer: 5'-CAG-TGC-ATA-TTA-GTG-GAC-AGC-ACT-TAG-3'(SEQ ID NO: 27), reverse primer:

5'-TGA-TGG-TCG-AGG-TGC-GGA-3' (SEQ ID NO: 28), probe: 6-FAM-CAC-CAG-GAG-CTG-CAA-GCC-ATG-CA-TAMRA (SEQ ID NO: 29)). Data analysis was done by comparative Ct method with plasmid standard curve. Results were normalized to ABL (forward primer: 5'-CAA-CAC-TGC-TTC-TGA-TGG-CAA-3' (SEQ ID NO: 30), reverse primer: 5'-CTG-GAT-AAT-GGA-GCG-TGG-TG-3' (SEQ ID NO: 31), probe: 6-FAM-CAA-CAC-CCT-GGC-CGA-GTT-GGT-TCA-T-TAMRA (SEQ ID NO: 32)).

Detection and Quantitation of NPM-ALK by Western Blot:

Four micrograms of protein were resolved on 10% SDS-PAGE gels, transferred onto nitrocellulose membrane, probed with individual antibodies and visualized using enhanced chemiluminescence detection system. The primary antibodies were anti-ALK antibody (Invitrogen), anti-β-actin (Sigma). The relative expression of NPM-ALK was determined using ImageJ software.

Protein Extraction and Digestion:

Cells were lysed in 1 mL of lysis buffer containing 8M urea/0.4M ammonium bicarbonate/0.1% SDS with sonication on ice and then spun at 16,000 g for 10 min. For each sample, 0.5 mg of protein were reduced with 10 mM Tris(2-carboxylethyl)phosphine for 60 min at 60° C. and then alkylated with 12 mM iodoacetamide for 30 min at room temperature in the dark. Samples were diluted 4-fold with 100 mM potassium phosphate pH 8.0 and then digested with trypsin overnight at 37° C. using an enzyme-to-protein ratio of 1/50 (w/w). After acidification with 6N HCl, samples were desalted on a C18 cartridge (Sep-Pak plus C18 cartridge, Waters). Purified peptides were eluted with 30% acetonitrile/0.1% trifluoroacetic acid and dried before any further processing. Each sample was prepared in triplicate.

High Performance Liquid Chromatography:

Dried peptides (0.5 mg) from either cell lysates derived from cell lines or primary tumor samples were dissolved in 250 μL, 1% acetic acid and 2% acetonitrile to create a 2 μg/μL peptide solution. A standard curve was prepared by spiking heavy NPM-ALK peptide C (57.0215) GSGPVHISGQHLV-VYR ($^{13}C_6/^{15}N_4$) (SEQ ID NO: 33) into a portion of the peptide solution then serial diluting with unspiked peptide solution (0.439 to 113 fmole/μL). Another portion of the peptide solution was spiked with double heavy NPM-ALK peptide C (57.0215) GSGPVHISGQHLV ($^{13}C_5/^{15}N$) VYR ($^{13}C_6/^{15}N_4$) (SEQ ID NO: 33) to serve as an internal standard. This was added to each standard level prior to injection on the LC-MS/MS (43.9 fmole/μL). Peptide samples were separated using an in-house packed reversed-phase column (Magic C18 AQ, 200 Å, 5μ (Michrom Bioresources, Inc.), 150 μm ID×100 mm) on the liquid chromatography (LC) Paradigm MS4 system (Michrom Bioresources, Inc.). Samples were injected using a Paradigm AS1 autosampler (Michrom Bioresources, Inc.). After 2 μL of each peptide sample was loaded onto the column, the LC gradient was initiated at a 1.1 μL/min flow rate with 92% mobile phase A (1% acetic acid and 2% acetonitrile) and 8% mobile phase B (1% acetic acid and 96% acetonitrile). The flow rate was increased to 1.3 μL/min and mobile phase B was increased to 43% over the next 60 minutes. Mobile phase B was brought to 99% over the next 5 minutes and held there for an additional 5 minutes. The flow rate and mobile phase composition were then brought back to the initial conditions over 5 minutes and held there for an additional 15 minutes to equilibrate the column.

Fusion Peptide Multiple Reaction Monitoring Mass Spectrometry:

A TSQ Quantum Ultra triple quadrupole mass spectrometer (Thermo Scientific) with a Silver-TSQ Ultra-Exactive MS source (Michrom Bioresources, Inc.) was used for all experiments. A number of fusion peptides were screened by MRM-MS. To detect the API2-MALT1 (ex7/ex5), BCR-ABL1 (e13a2) and BCR-ABL1 (e1a2) fusion peptides, the parameters as described in Table 1 were utilized. Chromatography conditions and linearity were also established for each (FIG. 1). The NPM-ALK fusion peptide was selected for further analysis to establish the feasibility and robustness of FP-MRM-MS. MS parameters for the NPM-ALK fusion peptide were as follows: Spray voltage: 1600 V, capillary temperature: 220° C., skimmer offset: −5. Transitions and parameters for each NPM-ALK fusion peptide (Table 2) were initially selected using Pinpoint Quantitation Software (v 1.1.7) (Thermo Fisher Scientific).

TABLE 2

| MRM parameters for API2-MALT1 and BCR-ABL1 fusion peptides | | | | | | | | |
|---|---|---|---|---|---|---|---|---|
| Fusion Protein | Fusion Peptide Sequence | Charge State | Light | | Heavy* | | Collision Energy | Fragment ion |
| | | | Q1 | Q3 | Q1 | Q3 | | |
| API2/MALT1 (ex7/ex5) | ESRSVDFVSESK (SEQ ID NO: 5) (Protease: Lys-C) | +2 | 640.31 | 234.15 | NA | NA | 25 | $y_2$ |
| | | | | 450.22 | | | | $y_4$ |
| | | | | 606.31 | | | | $y_6$ |
| | | | | 674.31 | | | | $b_6$ |
| | | | | 731.33 | | | | $b_7$ |
| | | | | 830.40 | | | | $b_8$ |
| | | | | 917.43 | | | | $b_9$ |
| | | | | 1046.48 | | | | $b_{10}$ |
| API2/MALT1 (ex7/ex5) | SRSVDGVSE (SEQ ID NO: 4) (Protease: Glu-C) | +2 | 468.23 | 235.09 | NA | NA | 19 | $y_2$ |
| | | | | 545.27 | | | | $b_5$ |
| | | | | 602.29 | | | | $b_6$ |
| | | | | 701.36 | | | | $b_7$ |
| | | | | 788.39 | | | | $b_8$ |
| BCR/ABL1 (e13a2) | TINKEEAL (SEQ ID NO: 2) (Protease: Chymotrypsin) | +2 | 459.250 | 589.319 | 462.860 | 596.319 | 19 | $y_5$ |
| | | | | 703.362 | | 710.362 | | $y_6$ |
| | | | | 715.362 | | 715.362 | | $b_6$ |
| | | | | 786.399 | | 786.399 | | $b_7$ |
| | | | | 816.446 | | 823.446 | | $y_7$ |

TABLE 2-continued

MRM parameters for API2-MALT1 and BCR-ABL1 fusion peptides

| Fusion Protein | Fusion Peptide Sequence | Charge State | Light | | Heavy* | | Collision Energy | Fragment ion |
|---|---|---|---|---|---|---|---|---|
| | | | Q1 | Q3 | Q1 | Q3 | | |
| BCR/ABL1 (e1a2) | HGDAEAL (SEQ ID NO: 3) (Protease: Chymotrypsin) | +2 | 356.667 | 310.114 | 360.250 | 310.114 | 16 | $b_3$ |
| | | | | 381.151 | | 381.151 | | $b_4$ |
| | | | | 510.194 | | 510.194 | | $b_5$ |
| | | | | 581.231 | | 581.231 | | $b_6$ |

*"Heavy" refers to the isotopic version of the peptide.
The heavy peptides contain an isotopically labeled leucine ($^{13}C_6/^{15}N$) at the C-terminus making them 7 Da heavier than their light counterparts.
Red: Amino acid residues contributed by fusion partner 1
Blue: Amino acid residues contributed by fusion partner 2

Figure 2:
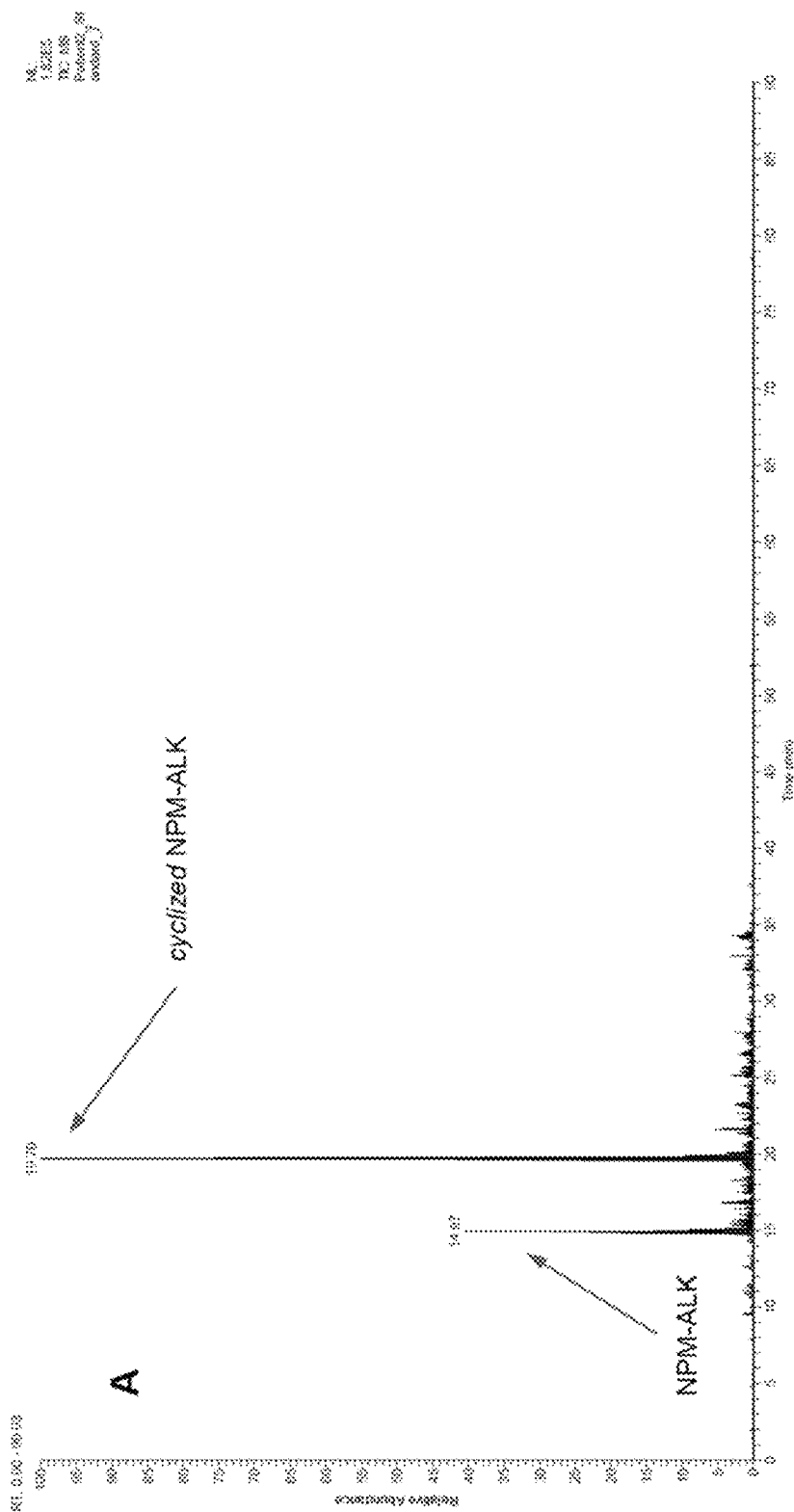
FIG. 2 shows NPM-ALK fusion peptide chromatography. (A) A representative total ion chromatogram showing retention time separation between the cyclized and uncyclized forms of the NPM-ALK fusion peptides by reverse phase chromatography. (B) Direct infusion of the NPM-ALK fusion peptide onto the mass spectrometer revealing a cyclized and uncyclized form in both a +2 and +3 charge state.
Figure 2:
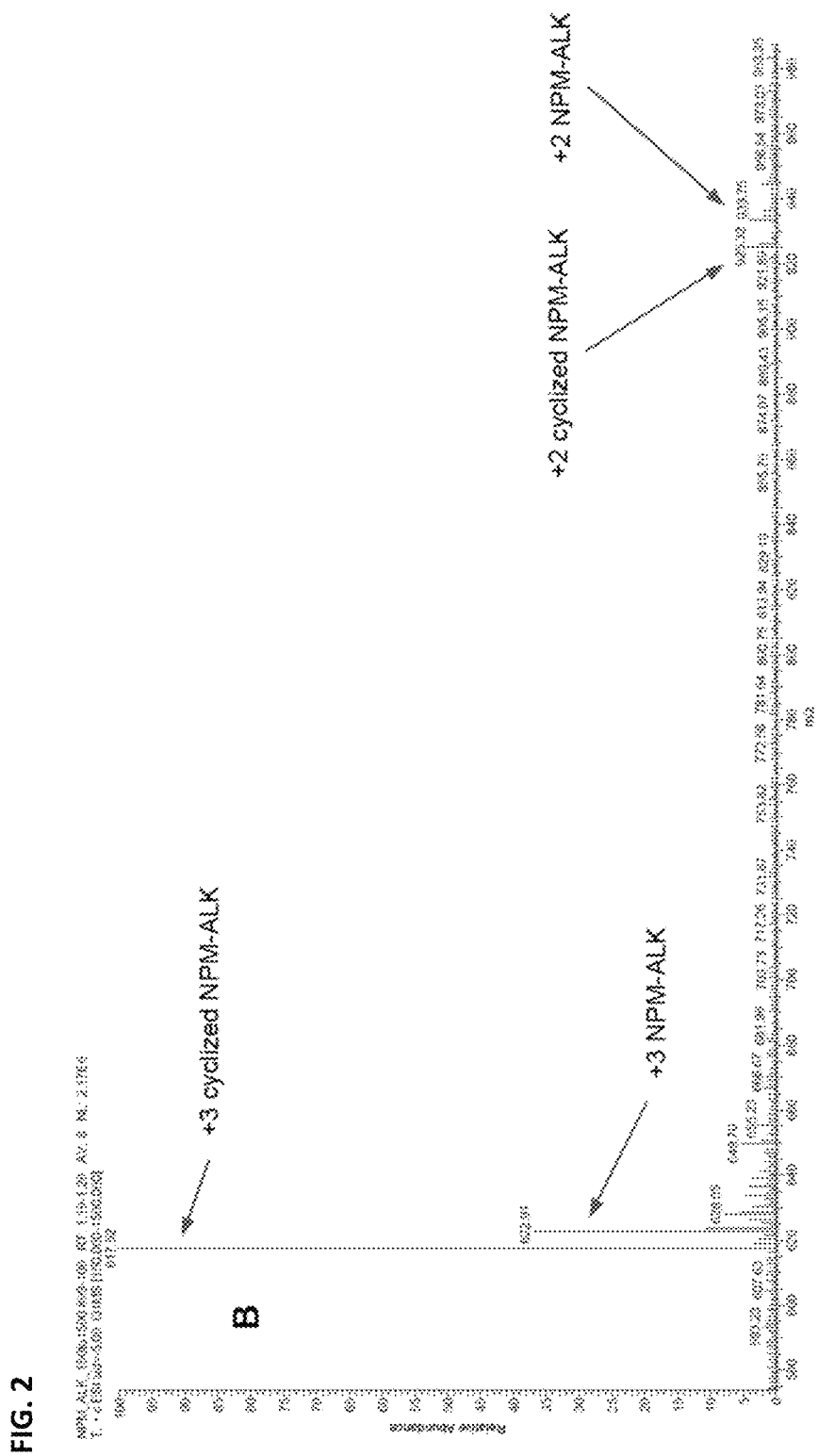

The NPM-ALK fusion peptide (CGSGPVHISGQHLV-VYR (SEQ ID NO: 1)) generated by digestion with trypsin contains an NH2-terminal cysteine. Carbamidomethylation of NH2-terminal cysteine can cause peptides to undergo spontaneous cyclization in a pH and time dependent manner, resulting in a cyclized and uncyclized form of the peptide (FIG. 2) (see, e.g., Geoghegan K F, et al.: J Proteome Res 1: 181-7, 2002; herein incorporated by reference in its entirety). LC-MS/MS analysis of the NPM-ALK fusion peptide indicated the presence of cyclized and uncyclized forms, with different hydrophobicity characteristics resulting in separate elution times in a standard reverse phase gradient system (FIG. 2A). The 3 peptides individually infused into a triple quadrupole mass spectrometer and observed +2 and +3 charge states, with the +3 charge state being the most abundant ion for both cyclized and uncyclized forms (FIG. 2B).

Figure 3:
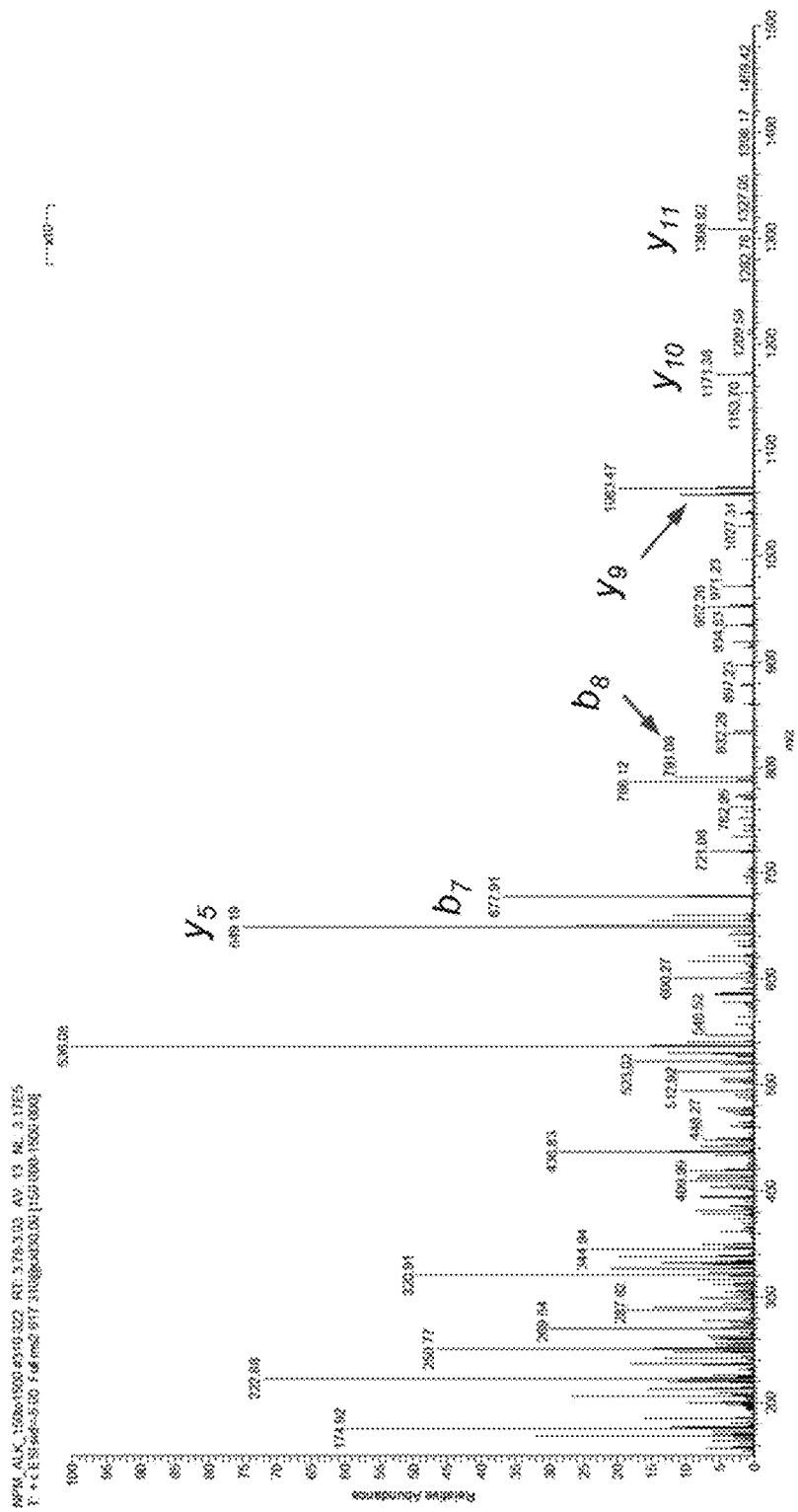
FIG. 3 shows MS/MS of NPM-ALK fusion peptide. (A-C) NPM-ALK, Heavy NPM-ALK and Double Heavy NPM-ALK were directly infused into the mass spectrometer at 1 picomole/µL. A Product Scan of the +3 cyclized form of each was collected and the MS/MS fragmentation shown. Ions monitored by MRM are labeled.
Figure 3:
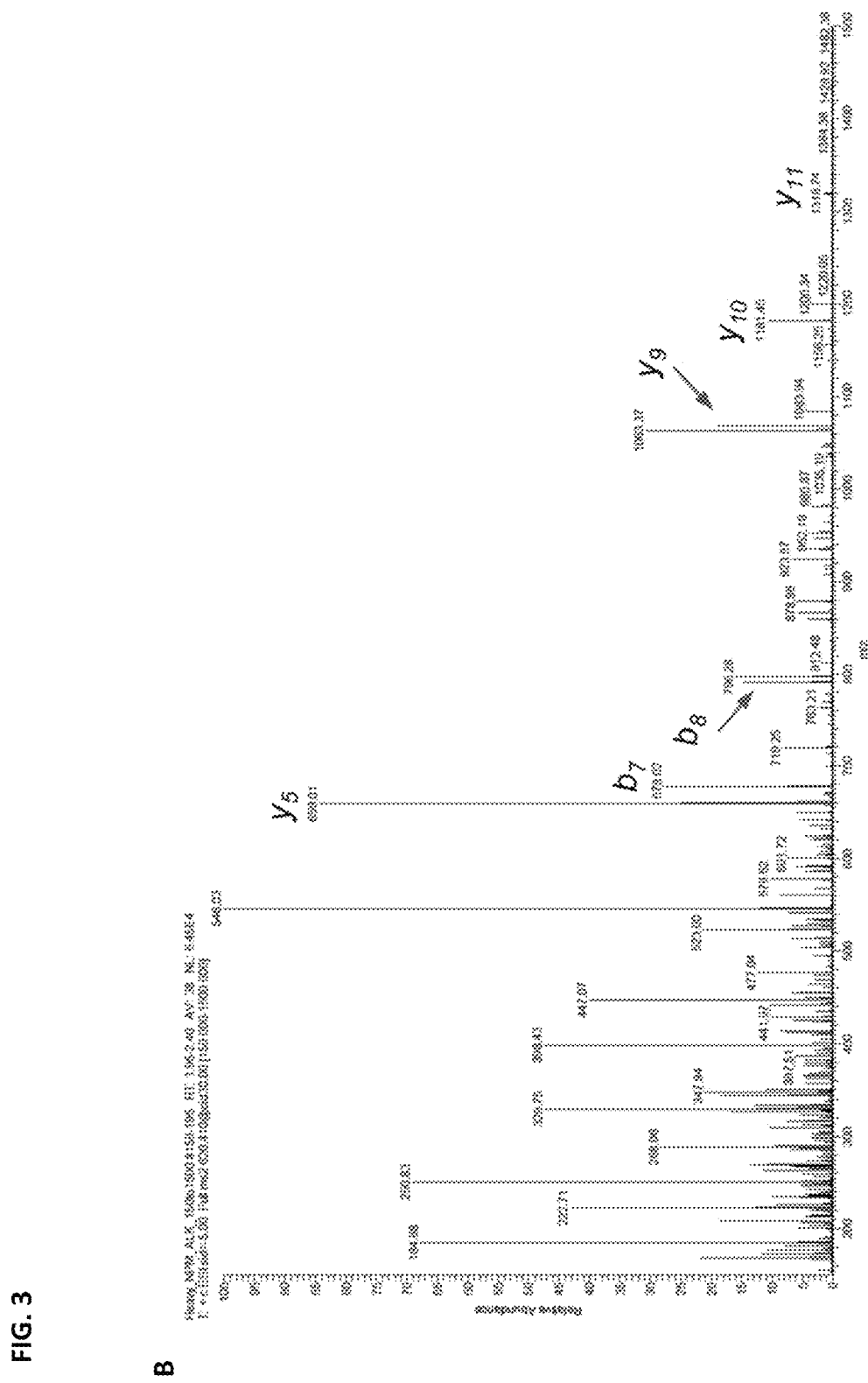
Figure 3:
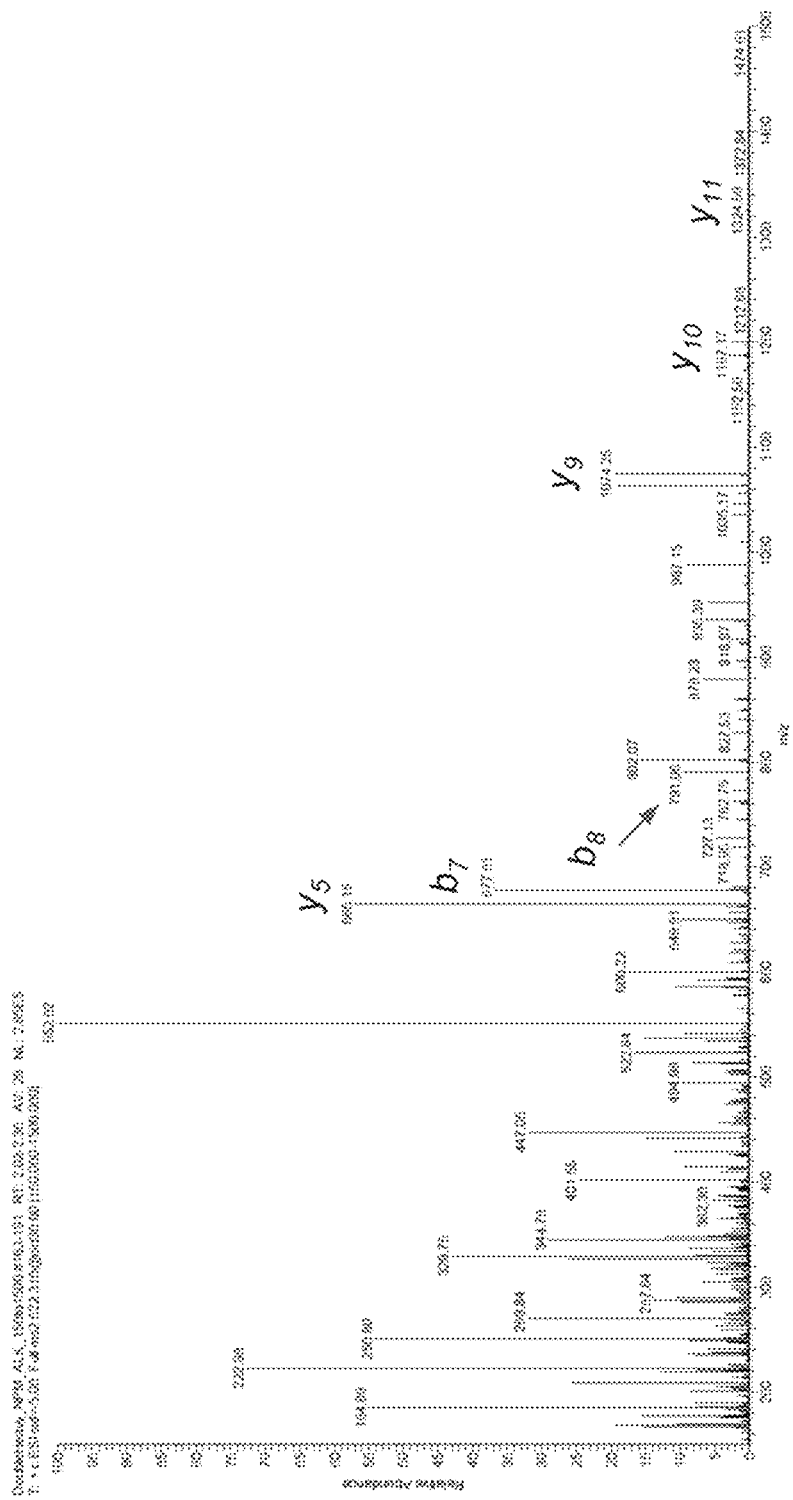
Figure 4:
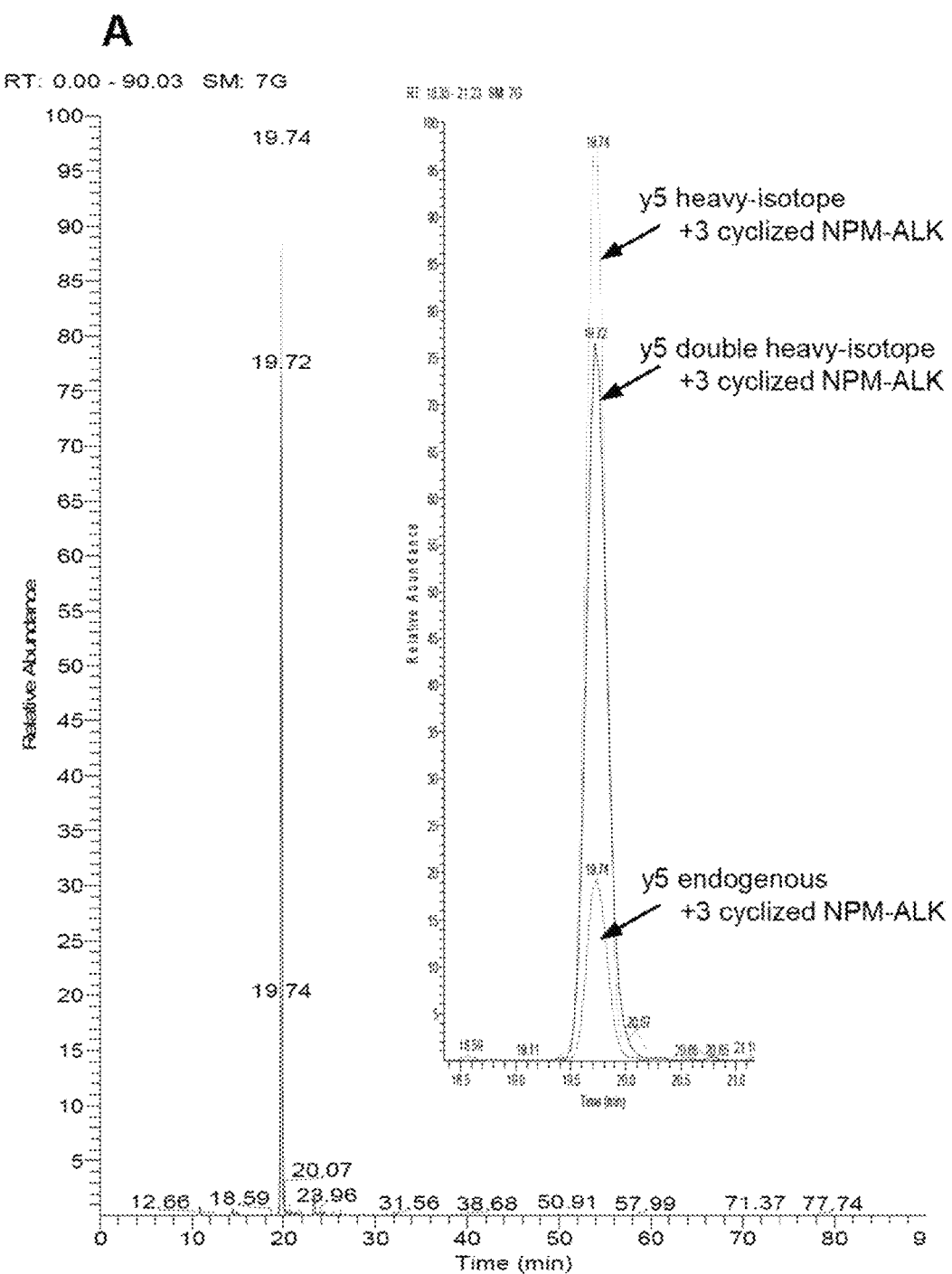
FIG. 4 shows extracted ion chromatogram of the NPM-ALK fusion peptide. The entire chromatographic run is shown with retention times indicated at the top of the peaks. The inset to the right of each represents an expanded view of the NPM-ALK fusion peptide. (A) An extracted ion chromatogram of the quantitation ion used for the NPM-ALK fusion peptide is shown. The ion ($y_5$) used for quantitation is displayed for the endogenous, heavy and double heavy NPM-ALK fusion peptide. Extracted ion chromatograms showing the ions monitored for (B) cyclized +3 charged endogenous NPM-ALK fusion peptide, (C) cyclized +3 charged heavy NPM-ALK fusion peptide and (D) cyclized +3 charged double heavy NPM-ALK fusion peptide.
Figure 4:
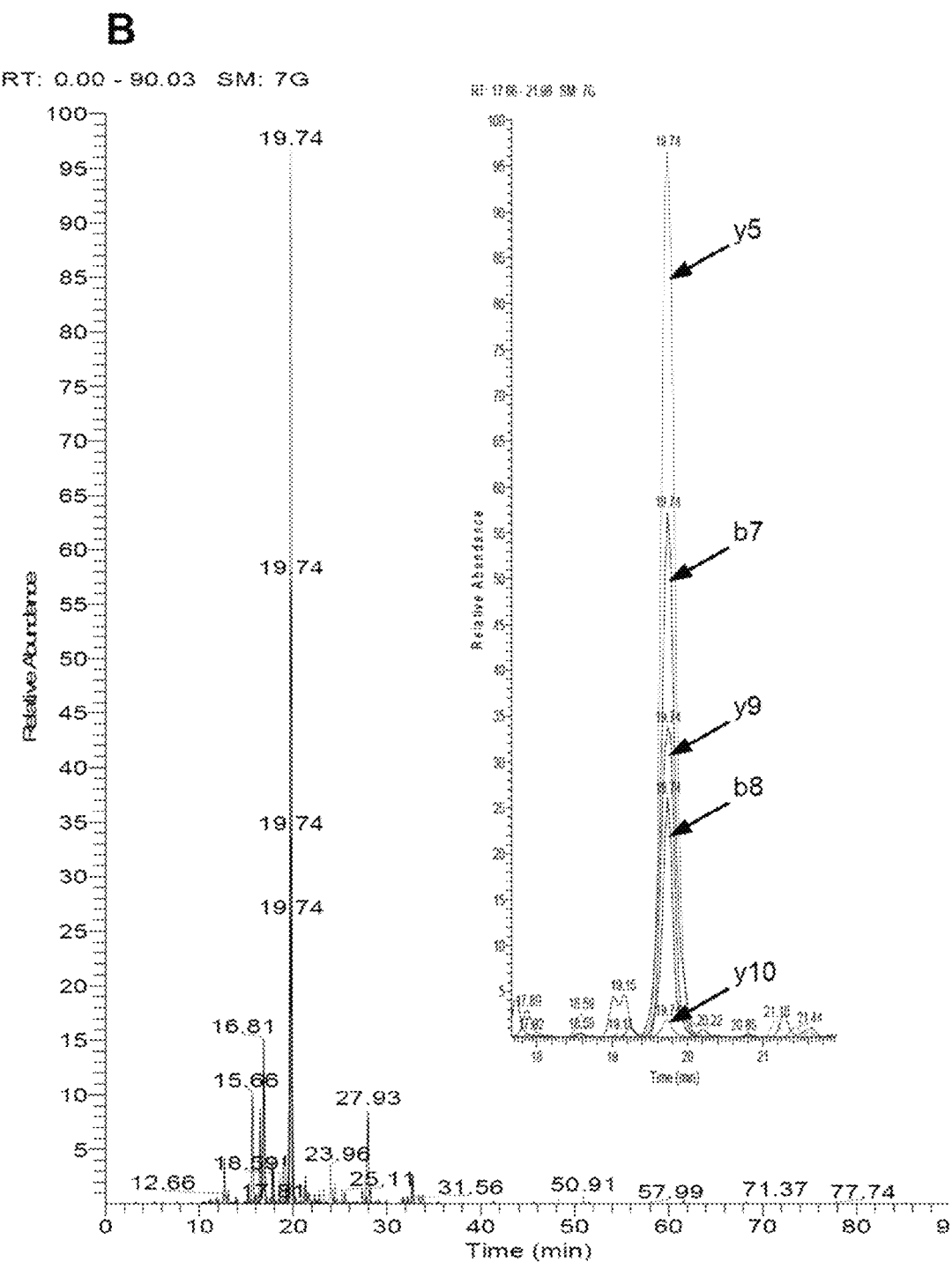
Figure 4:
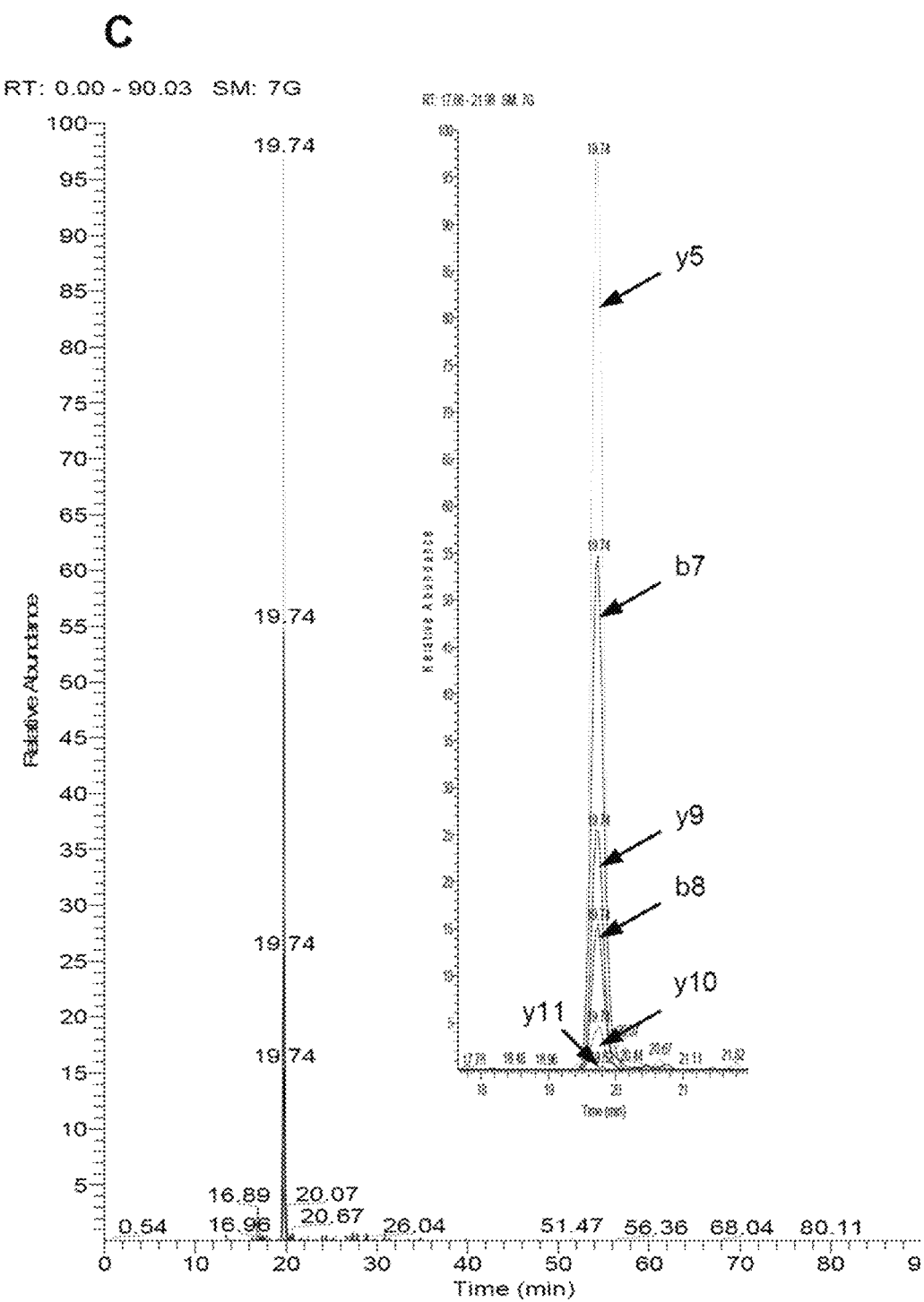
Figure 4:
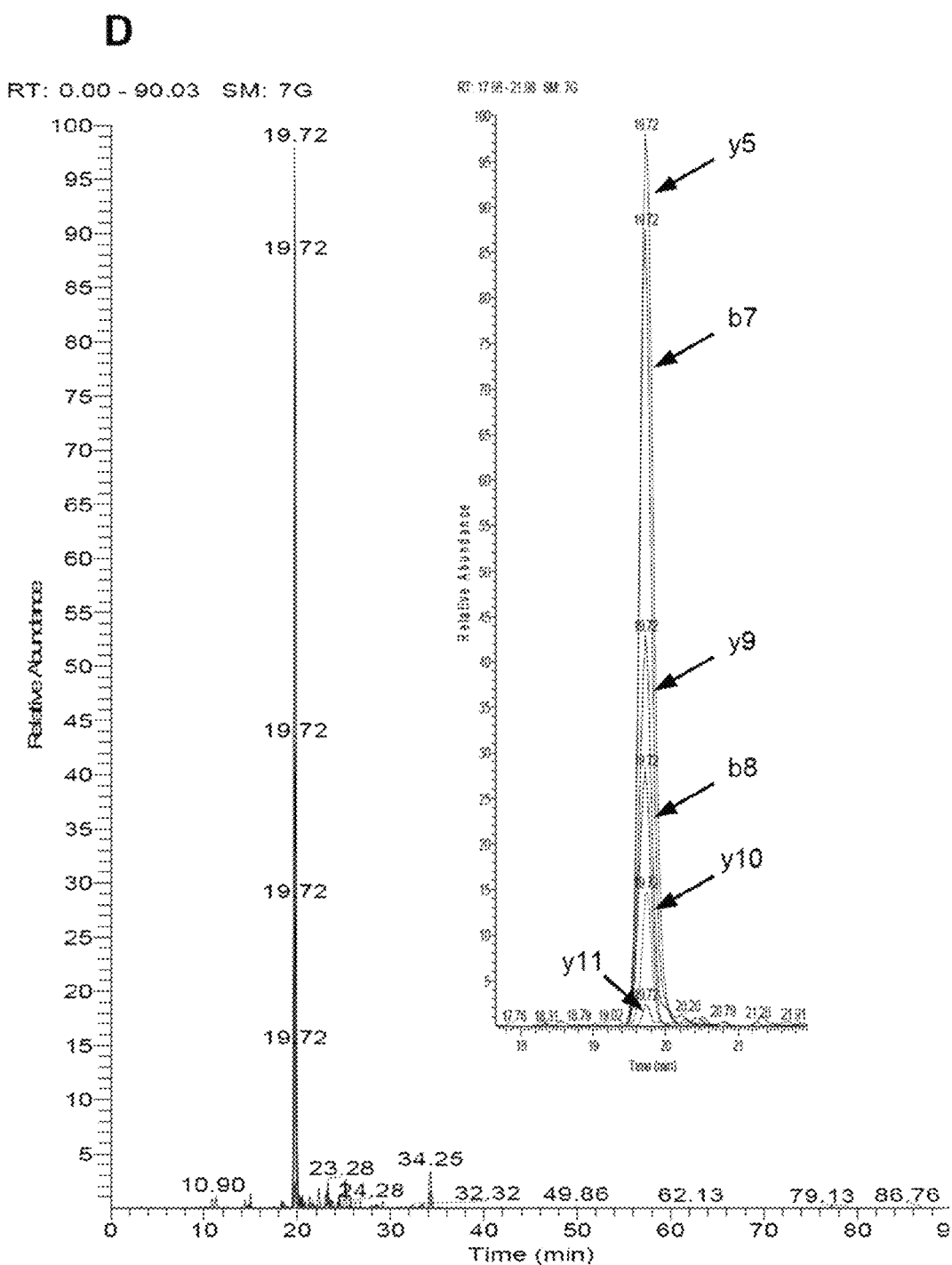
Figure 5:
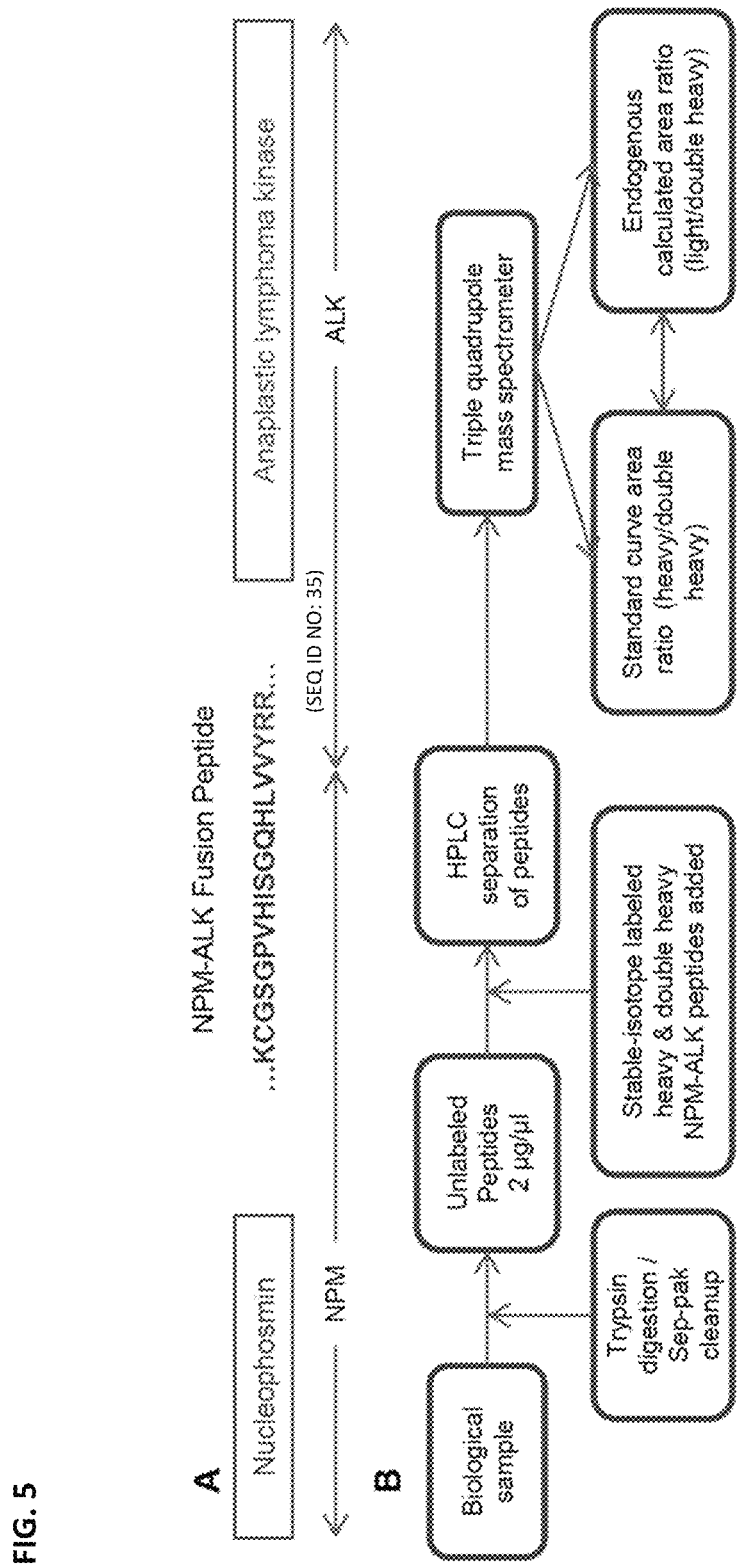
FIG. 5 shows a schematic of FP-MRM for the detection of NPM-ALK fusion peptide in cell lines and patient samples. An overview of the FP-MRM approach showing (A) an illustration of the tryptic NPM-ALK fusion peptide and (B) a schematic of the sample processing and FP-MRM analysis workflow. (C) An extracted ion chromatogram of the quantitation ion used for the NPM-ALK fusion peptide is shown. The entire chromatographic run is shown with retention times indicated at the top of the peaks. The inset to the right represents an expanded view of the NPM-ALK fusion peptide. The ion ($y_5$) used for quantitation is displayed for the endogenous, heavy and double heavy NPM-ALK fusion peptide. Representative nine point calibration curves prepared using (D) 2 µg/µL of an NPM-ALK positive cell lysate (SR786) with a correlation coefficient of 0.9947 and (E) 2 µg/µL of an NPM-ALK positive patient sample (418) with a correlation coefficient of 0.9986. Heavy NPM-ALK peptide ranged from 0.439 to 113 fmole/µL and double heavy NPM-ALK peptide was added to each standard level at 43.9 fmole/µL. An area ratio (Heavy/Double Heavy) is calculated for each point and a linear curve derived. No light NPM-ALK peptide is added.
Figure 5:
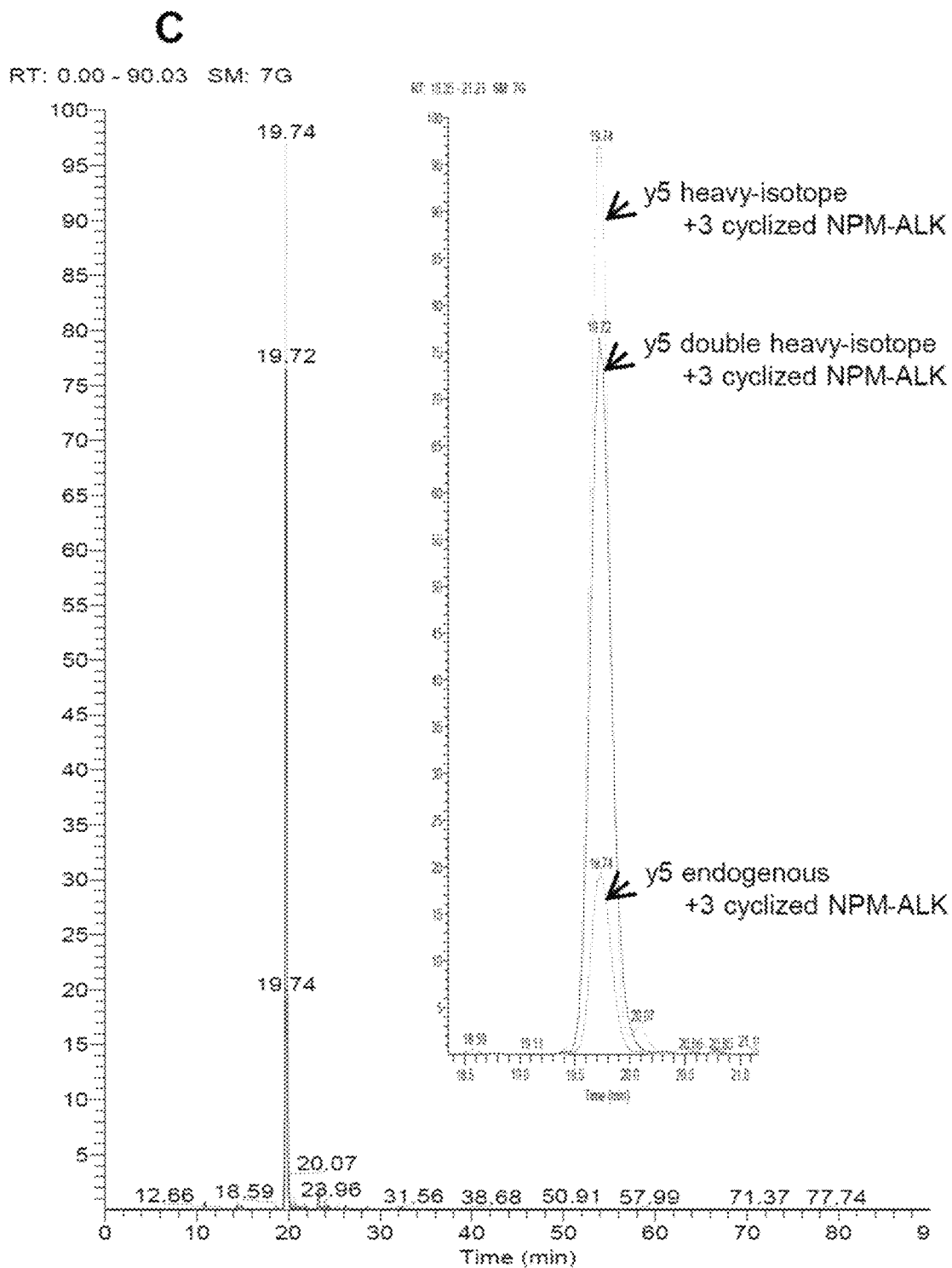
Figure 5:
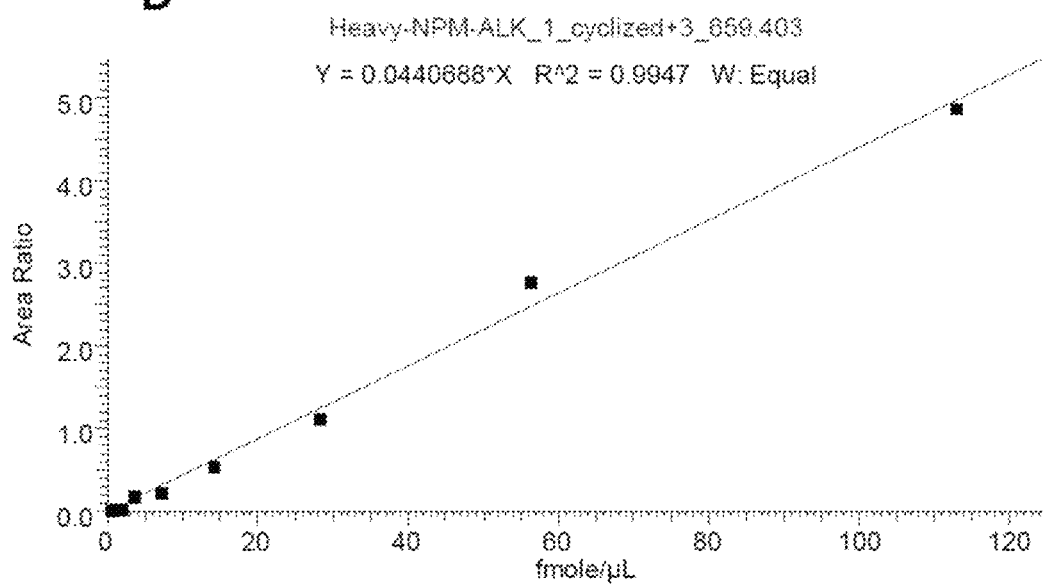
Figure 5:
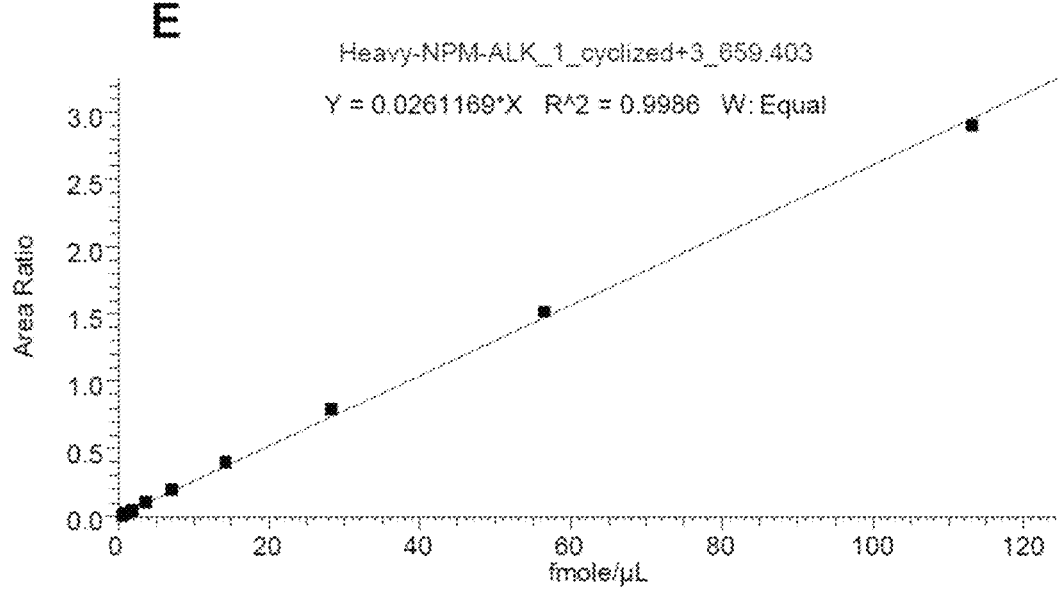

Both the cyclized and uncyclized +2 and +3 charged precursor ions were selected for monitoring along with 5 to 6 product ions for each isotopic variant. Only y and b ion series product ions with m/z greater than its precursor m/z were chosen (see, e.g., Keshishian H, et al.: Mol Cell Proteomics 8: 2339-49, 2009; herein incorporated by reference in its entirety). The optimized parameters in terms of collision energy and daughter ion selection for Q3 transition are presented in Table 2. Results presented are based upon the cyclized +3 form of the NPM-ALK fusion peptide which provided the greatest signal intensity. While several Q3 transitions were monitored for unambiguous identification of the target peptide, the y5 ion was chosen for quantitation as it was the most intense ion that exhibited a higher mass than the parent peptide (FIGS. 3 and 4). Representative extracted ion chromatograms are shown for the cyclized +3 charged NPM-ALK peptide (FIG. 5C and FIG. 4).

TABLE 2

MRM Parameters for NPM-ALK fusion peptides (SEQ ID NO: 33)

| NPM-ALK Peptide Sequence | Charge State | Light | | Heavy* | | Double Heavy* | | Collision Energy | Fragment ion |
|---|---|---|---|---|---|---|---|---|---|
| | | Q1 | Q3 | Q1 | Q3 | Q1 | Q3 | | |
| C(57.021454)GSGPVHISGQHLVVYR | +2 | 933.476 | 1058.574 | 938.480 | 1058.574 | 941.475 | 1074.574 | 38 | $y_9^\#$ |
| | | | 1050.459 | | 1050.489 | | 1080.489 | | $b_{11}$ |
| | | | 1171.656 | | 1181.656 | | 1187.656 | | $y_{12}$ |
| | | | 1308.717 | | 1318.717 | | 1324.717 | | $y_{11}$ |
| | | | 1330.632 | | 1330.532 | | 1330.532 | | $b_{12}$ |
| C(57.021454)GSGPVHISGQHLVVYR | +3 | 622.890 | 649.403 | 625.100 | 559.403 | 527.965 | 655.403 | 30 | $y_5^\#$ |
| | | | 786.462 | | 495.452 | | 602.452 | | $y_6$ |
| | | | 971.542 | | 981.542 | | 987.542 | | $y_8$ |
| | | | 1058.574 | | 1066.574 | | 1074.574 | | $y_8$ |
| | | | 1080.489 | | 1080.489 | | 1080.489 | | $b_{11}$ |
| | | | 1407.785 | | 1417.785 | | 1423.785 | | $y_{12}$ |
| C(39.994915)GSGPVHISGQHLVVYR Cyclized | +2 | 924.952 | 791.351 | 929.952 | 791.351 | 932.962 | 791.351 | 38 | $b_5$ |
| | | | 971.542 | | 981.542 | | 987.542 | | $y_6$ |
| | | | 1055.574 | | 1063.574 | | 1074.574 | | $y_8^\#$ |
| | | | 1171.558 | | 1181.558 | | 1167.558 | | $y_{10}$ |
| | | | 1308.717 | | 1315.717 | | 1324.717 | | $y_{11}$ |

TABLE 2-continued

MRM Parameters for NPM-ALK fusion peptides (SEQ ID NO: 33)

| NPM-ALK Peptide Sequence | Charge State | Light | | Heavy* | | Double Heavy* | | Collision Energy | Fragment ion |
|---|---|---|---|---|---|---|---|---|---|
| | | Q1 | Q3 | Q1 | Q3 | Q1 | Q3 | | |
| C(39.994915)GSGPVHISGQHLVVYR Cyclized | +3 | 617.31 | 649.403 | 620.410 | 659.403 | 522.31 | 655403 | 30 | yb$_5$# |
| | | | 678.255 | | 678.255 | | 678.255 | | b$_7$ |
| | | | 791.351 | | 791.351 | | 791.351 | | b$_8$ |
| | | | 1055.574 | | 1063.574 | | 1074.574 | | y$_9$ |
| | | | 1171.558 | | 1181.558 | | 1167.558 | | y$_{10}$ |
| | | | 1308.717 | | 1315.717 | | 1324.717 | | y$_{11}$ |

*"Heavy" and "Double Heavy" refer to the isotopic version of the peptide.
Represents the most intense fragment ion
The heavy peptides contain an isotopically labeled arginine ($^{13}C_8/^{15}N_4$) at the C-terminus making them 10 Da heavier than their light counterparts.
The double heavy peptides contain both an isotopically labeled arginine ($^{13}C_8/^{15}N_4$) at the C-terminus as well as an isotopically labeled valine ($^{13}C_8/^{15}N$) making them 16 Da heavier than their light counterparts.
Red: Amino acid residues contributed by fusion partner 1
Blue: Amino acid residues contributed by fusion partner 2

Multiple reaction monitoring (MRM) was carried out in positive ion mode with the following conditions: Scan width: 0.002 m/z, scan time: 0.020 s, Q1: 0.70 FWHM, Q3: 0.70 FWHM, collision gas pressure: 1.5 mTorr, chrom filter peak width: 5 s. Data was collected in centroid mode and processed using Xcalibur (v 2.0.6) (Thermo Electron Corporation). Processed data was then exported to Excel 2010 (Microsoft) where the endogenous NPM-ALK peptide values were calculated by inserting the light NPM-ALK peptide area ratios into the linear equation obtained from the heavy/double heavy NPM-ALK peptide curve.

The limit of detection (LOD) and limit of quantitation (LOQ) was determined for each curve. The LOD was determined by the lowest standard which gave a signal/noise ratio >10. The LOQ was determined by the lowest standard which gave a signal/noise ratio >10 and its calculated value based upon the standard curve was ≤20 percent different than the theoretical value.

Example II

This example describes identification of fusion peptides from chimeric fusions and selection of a model system. To determine if the chimeric fusion proteins arising from chromosomal translocations yield specific fusion peptides upon digestion with common proteases, 26 chimeric fusions known to occur in a spectrum of human cancers were evaluated. Two criteria for qualification of a peptide as suitable by FP-MRM analysis were required: 1) amino acids from both fusion partners contribute to the composition of the fusion peptide, and 2) commonly used proteolytic enzymes generate a fusion peptide that is suitable for MS analysis. As indicated in Table 3, all of the 26 chimeric fusions that were examined generated fusion peptides that met the criteria. Chromatography, linearity and MRM parameters were established for fusion peptides derived from NPM-ALK, API2-MALT1 and BCR-ABL1 which are diagnostic of NPM-ALK positive ALCL, extranodal marginal zone B-cell lymphoma of mucosa-associated lymphoid tissue and chronic myeloid leukemia, respectively (See Example I, FIG. 5C-E, FIG. 1-4 and Tables 1 and 2). NPM-ALK positive ALCL was then selected as the model system to demonstrate the utility of fusion peptides as biomarkers for specific cancer detection in a clinically relevant scenario. Over 90% of NPM-ALK positive ALCLs are characterized by the t(2;5)(p23;q35) aberration resulting in the fusion of the N-terminal domain of nucleophosmin, a ubiquitously expressed protein, to the C-terminal tyrosine kinase domain of ALK, a receptor tyrosine kinase expressed almost exclusively in cells of neuronal origin (see, e.g., Morris S W, et al.: Science 263: 1281-4, 1994; herein incorporated by reference in its entirety). Trypsin digestion of the protein was predicted to generate a fusion peptide consisting of amino acids from both NPM and ALK (FIG. 5A and Table 3).

TABLE 3

Examples of chimeric fusion proteins involved in cancers and their predicted fusion peptides

| | Cytogenetic abnormality | Fusion protein | Disease | Fusion peptide | Protease | |
|---|---|---|---|---|---|---|
| Hematological neoplasm (leukemia/lymphoma) | t(2;5)(p23;q35) | NPM-ALK* | ALK-positive ALCL | CGSGPVHISGQHLV-VYR | Trypsin | (SEQ ID NO: 1) |
| | t(9;22)(p34;q11.2) | BCR-ABL1 (E13A2)* | CML,B-ALL | TINKEEAL | Chymotrypsin | (SEQ ID NO: 2) |
| | t(9;22)(p34;q11.2) | BCR-ABL1 (E1A2)* | CML,B-ALL | HGDAEAL | Chymotrypsin | (SEQ ID NO: 3) |
| | t(11;18)(p21;q21) | AP12-MALT1 (ex7-ex5)* | MALT lymphoma | SRSVDGVSE | V8-DE | (SEQ ID NO: 4) |
| | t(11;18)(p21;q21) | AP12-MALT1 (ex7-ex5)* | MALT lymphoma | ESRSVDGVSESK | Lys-C | (SEQ ID NO: 5) |

TABLE 3-continued

Examples of chimeric fusion proteins involved in cancers and their predicted fusion peptides

| | Cytogenetic abnormality | Fusion protein | Disease | Fusion peptide | Protease | |
|---|---|---|---|---|---|---|
| | t(11;18)(p21;q21) | AP12-MALT1 (ex7-ex8)* | MALT lymphoma | ESNELNNLGHPDNK | Trypsin | (SEQ ID NO: 6) |
| | t(1;2)(p25;q23) | TPM3-ALK | ALK-positive ALCL | TIDDLEVYR | Trypsin | (SEQ ID NO: 7) |
| | t(2;17)(p23;q23) | CLTC-ALK | ALK-positive DLBCL, and ALCL | LPGHVAADHPPAVYR | Trypsin | (SEQ ID NO: 26) |
| | t(2;5)(p23;q35) | SQSTM1-ALK | ALK positive DLBCL | NVGESVAAALSPLVYR | Trypsin | (SEQ ID NO: 8) |
| | t(4;11)(p21;q23) | MLL-AF4 | Biphenotypic ALL, B-ALL | FKQTYSNE | V8-DE | (SEQ ID NO: 9) |
| | t(9;11)(p22;q23) | MLL-AF9 | AML | SDFVYCQVCCEPFHK | Trypsin | (SEQ ID NO: 10) |
| | t(8;21)(p22;q22) | AML1-MTG8 | AML | ITVDGPREPRNRTEK | Lys-C | (SEQ ID NO: 11) |
| | t(2;11)(p31;q15) | NUP98-HOXD13 | AML | GAPQAPVGDVAL | Chymotrypsin | (SEQ ID NO: 12) |
| | t(11;19)(p23;q13.3) | MLL-ELL | AML | VDFKDSVSLR | Arg-C | (SEQ ID NO: 13) |
| | t(15;17)(p22;q21) | PML-RARA | APL | LSSCITQGKAIE | V8-DE | (SEQ ID NO: 14) |
| Epithelial neoplasm (carcinoma) | inv(2)(p21;p23) | EML4-ALK (Variant 1) | NSCLC | PTPGKGPKVYRRKHQE | V8-DE | (SEQ ID NO: 15) |
| | inv(2)(p21;p23) | EML4-ALK (Variant 2) | NSCLC | YIMSNSGDYEILYLYR | Trypsin | (SEQ ID NO: 16) |
| | inv(2)(p21;p23) | EML4-ALK (Variant 3a) | NSCLC | KNSQVYRRKHQE | V8-DE | (SEQ ID NO: 17) |
| | inv(7)(p21;p34) | AKAP9-BRAF | Papillary thyroid carcinoma | SEQDLIR | Trypsin | (SEQ ID NO: 18) |
| Mesenchymal neoplasm (sarcoma) | t(X;18)(p11.2;q11.2) | SYT-SSX1 | Synovial sarcoma | QIMPKKPAE | V8-DE | (SEQ ID NO: 19) |
| | t(X;18)(p11.2;q11.2) | SYT-SSX2 | Synovial sarcoma | QIMPKKPAE | V8-DE | (SEQ ID NO: 19) |
| | t(21;22)(p21;q12) | EWS/WT1 | Ewing sarcoma | GQQSSGQIQL | Chymotrypsin | (SEQ ID NO: 20) |
| | t(2;13)(q35;q14) | PAX3-FOXO1 | Alveolar rhabdosarcoma | SPQNSIRHNL | Chymotrypsin | (SEQ ID NO: 21) |
| | t(11;22)(p23;p13;q12) | EWS/WT1 | DSRCT | GQQSEKPY | Chymotrypsin | (SEQ ID NO: 22) |
| | t(12;22)(p23;p13;q12) | EWSR1/ATF1 (fusion type 1) | Clear Cell sarcoma | GGMGKILKDLSSEDTR | Arg-C | (SEQ ID NO: 23) |
| | t(12;22)(p23;p13;q12) | EWSR1/ATF1 (fusion type 2) | Clear Cell sarcoma | GQQIAIAPNGAL | Chymotrypsin | (SEQ ID NO: 24) |
| | t(17;22)(p23;p22;q13) | COL1A1-PDGFB | Dermatofibrosarcoma protuberans | QGPSGASGPAGPRGD | V8-DE | (SEQ ID NO: 25) |

Key
*Detected by fusion peptide multiple reacton monitoring mass spectrometry in this study.
Red: Amino acid residues contributed by fusion partner 1
Blue: Amino acid residues contributed by fusion partner 2
Abbreviations: ALCL - Anaplastic large cell lymphoma, CML - Chronic myeloid leukemia, B-ALL - B-cell acute lymphoblastic leukemia,
MALT — Mucosa associated lymphoid tissue, DLBCL - Diffuse large B-cell lymphoma, AML - Acute myeloid leukemia,
APL — Acute promyelocytic leukemia, NSCLC - Non small cell lung cancer, DSCRCT - Desmoplastic small round cell tumor.

Example III

This example describes the development of a double stable isotope labeling strategy for quantitative assessment of endogenous NPM-ALK fusion peptide by LC-MRM. The presence of other peptides and small molecules in the matrix can suppress or enhance the signal of the target analyte (see, e.g., Keshishian H, et al.: Mol Cell Proteomics 6: 2212-29, 2007; herein incorporated by reference in its entirety). Pooled normal serum, body fluids or cell lines that do not express the target analyte are background matrices commonly used to generate a standard curve using liquid chromatography (LC)-MRM against which test sample response is compared. However, these are still prone to introduce matrix associated errors in quantitation (see, e.g., Keshishian H, et al.: Mol Cell Proteomics 6: 2212-29, 2007; herein incorporated by reference in its entirety). In order to ensure that the assay accurately measured endogenous NPM-ALK levels in different matrices, an innovative quantitation strategy was devised using two stable isotope-labeled NPM-ALK peptides along with LC-MS and multiple reaction monitoring (FP-MRM) (See Example I). In this assay, heavy and double heavy NPM-ALK peptides were used to generate a standard curve directly in each test matrix allowing endogenous NPM-ALK peptide response to be determined from the same injections (n=9) (FIGS. 5D and E). By establishing the standard curve directly in the sample matrix, potential quantitation errors seen when the analyte response between the standard curve matrix and sample matrix differs was eliminated (see, e.g., Keshishian H, et al.: Mol Cell Proteomics 6: 2212-29, 2007; herein incorporated by reference in its entirety).

Example IV

Figure 6:
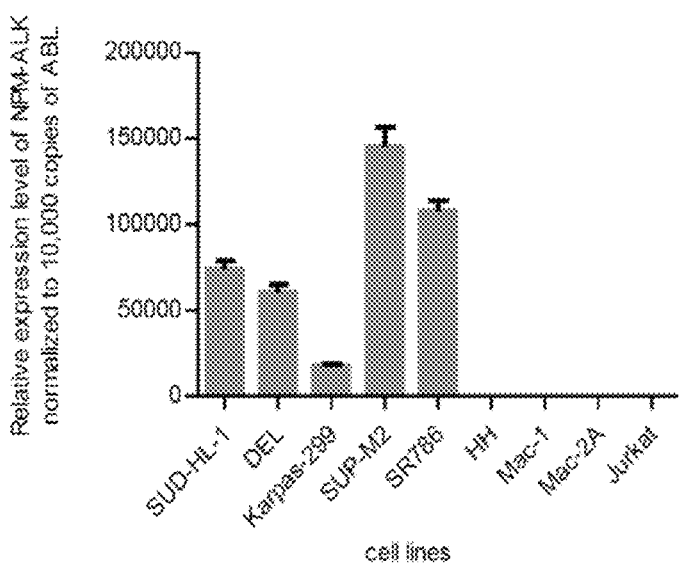
FIG. 6 shows detection of NPM-ALK fusion peptide in cell lines. Five NPM-ALK positive and four NPM-ALK negative cell lysates were analyzed using different techniques. (A) Cell lysate quantitation results obtained using the FP-MRM approach were in agreement with (B) those obtained by the quantitation of NPM-ALK expression by quantitative real-time PCR. mRNA was quantified using a TaqMan probe-based assay. The expression level of NPM-ALK transcript was normalized to the expression levels of ABL for each cell line. Data represents the mean of three biological replicates and error bars represent SD. (C) NPM-ALK expression by western blot analysis was also in agreement with the corresponding FP-MRM data. (D) Quantitation of the western blot results for NPM-ALK expression are shown. The expression level of NPM-ALK was normalized to the expression levels of β-actin for each cell line. Data represents the mean of three biological replicates and error bars represent SD.
Figure 6:
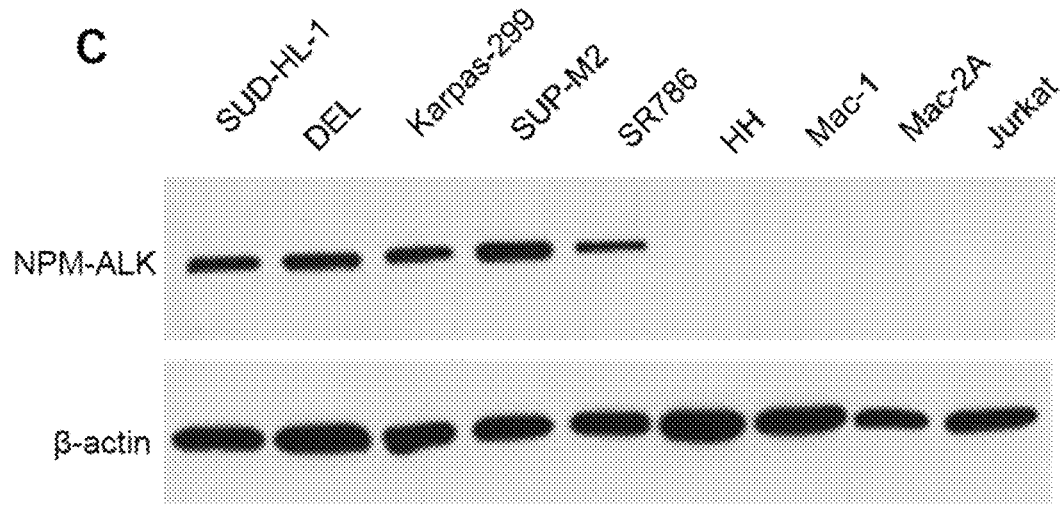
Figure 6:
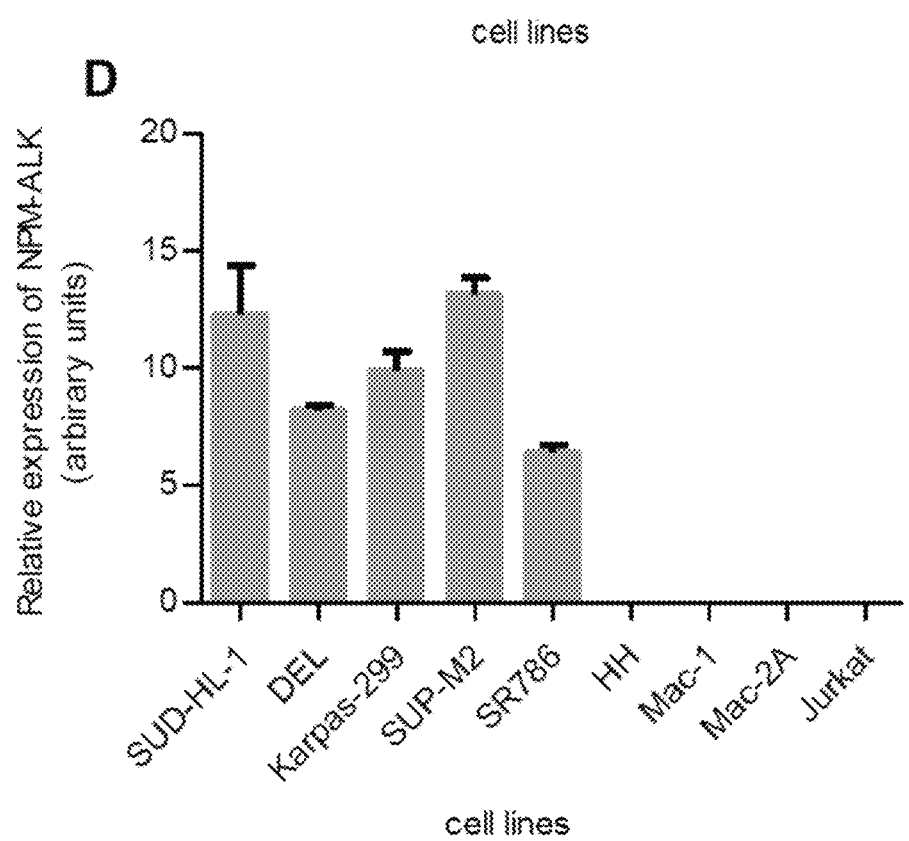
Figure 7:
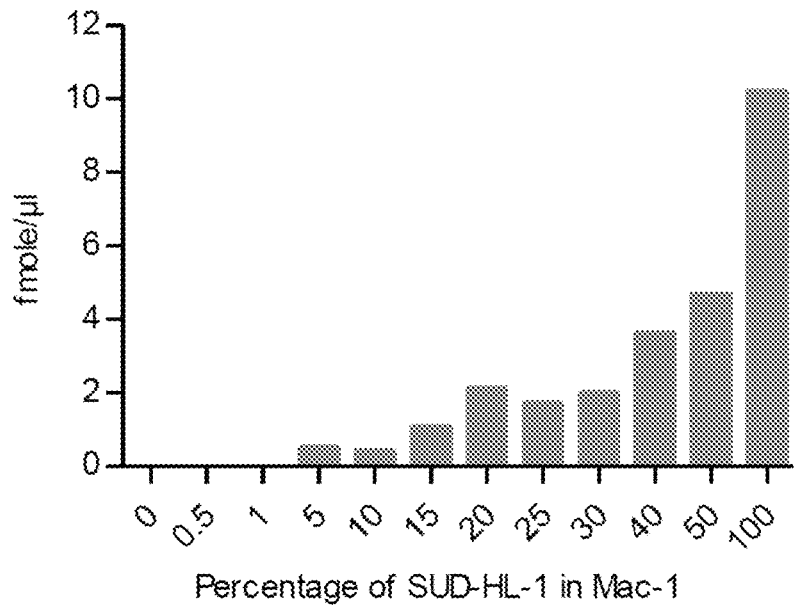
FIG. 7 shows cell lysate dilution studies. SUDHL1 cells (NPM-ALK +): Mac1 cells (NPM-ALK −). To assess the sensitivity at the cellular level at which FP-MRM analysis could detect the NPM-ALK fusion peptide, a series of dilutions were prepared using an NPM-ALK positive cell lysate (SUD-HL-1) and a negative cell lysate (Mac1). A standard curve was prepared in Mac1 using the heavy and double heavy NPM-ALK peptide as previously described against which all dilutions were quantitated. Twelve dilutions were prepared (0.5 mg each) including a 0% and a 100% SUD-HL-1. (A) LC-MRM analysis was done in technical triplicates for each dilution. The NPM-ALK fusion peptide was detectable above the LOD at 5% NPM-ALK positive cells (SUD-HL-1) in a background of NPM-ALK negative cells (Mac1) and above the LOQ at 15% NPM-ALK positive cells (SUD-HL-1) in a negative background (Mac1) (B) Quantitation of NPM-ALK expression by quantitative real-time PCR was also done. mRNA was quantified using a TaqMan probe-based assay. The expression level of NPM-ALK transcript was normalized to the expression levels of ABL for each cell line. Data represents the mean of three biological replicates and error bars represent SD. (C) NPM-ALK expression by western blot analysis with the corresponding FP-MRM values below. The FP-MRM results were in agreement with both quantitative real-time PCR and western blot data analysis. (D) Quantitation of the western blot results for NPM-ALK expression are shown. The expression level of NPM-ALK was normalized to the expression levels of β-actin. Data represents the mean of three biological replicates and error bars represent SD.
Figure 7:
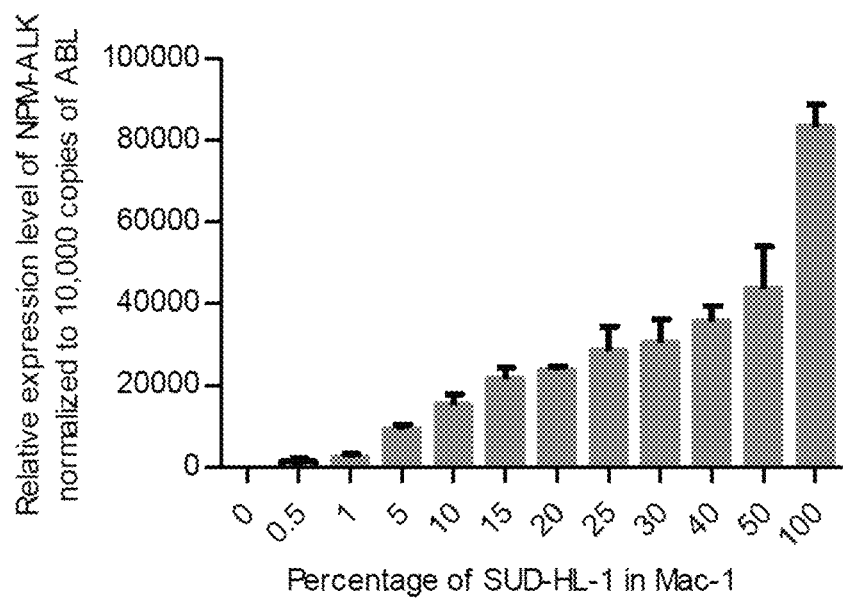
Figure 7:
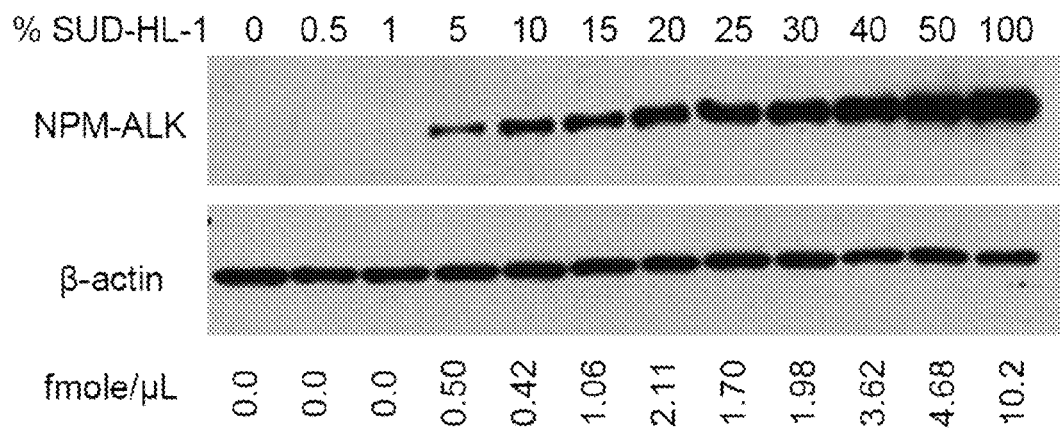
Figure 7:
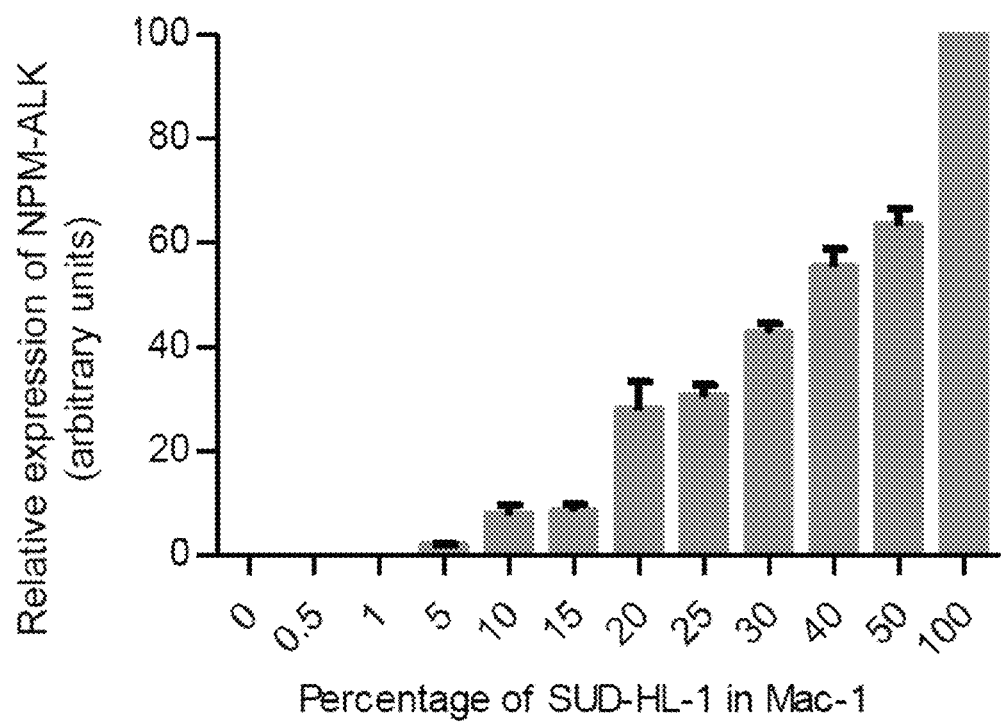

This example describes the quantitation of NPM-ALK fusion peptide expression by FP-MRM in cell lines. Having established the conditions for FP-MRM, a series of NPM-ALK positive and negative cell lysates were evaluated using the approach described (FIG. 5B). Protein lysates derived from five NPM-ALK positive cell lines (SUD-HL-1, Del, Karpas-299, Sup-M2 and SR786) and four NPM-ALK negative lymphoma cell lines (HH, Mac-1, Mac-2A and Jurkat) were analyzed. A representative standard curve in an NPM-ALK positive background (SR786) demonstrates linearity from 0.439 to 113 fmole/µL (220 to 56,500 fmole/mg lysate) (FIG. 5D). A representative extracted ion chromatogram (XIC) of the ion used for quantitation revealing co-elution of both endogenous and exogenously added peptides is shown in FIGS. 5C and 4A. Representative XIC's showing co-elution of all the ions monitored for the light, heavy and double heavy +3 cyclized form of the NPM-ALK fusion peptide are shown in FIG. 4 B-D. Using FP-MRM MS, endogenous NPM-ALK peptide in 5 NPM-ALK positive cell lines with a coefficient of variation (CV)<20% was successfully identified and quantitated (FIG. 6A). None of the 4 NPM-ALK negative cell lines exhibited detectable levels of the target analyte demonstrating absolute specificity (FIG. 6A). Across all cell lysates analyzed using this approach, the limit of detection (LOD) ranged from 0.439 to 0.879 fmole/µL (220 to 440 fmole/mg lysate) and the limit of quantitation (LOQ) ranged from 0.439 to 3.52 fmole/µL (220 to 1760 fmole/mg lysate) (FIG. 6A). The results of fusion peptide MRM analysis across the 9 cell lines were concordant with both quantitative real-time polymerase chain reaction (FIG. 6B) and western blot analysis (FIGS. 6C and D). Sensitivity and specificity for this method were calculated using cell lysate results which matched perfectly between experimental and expected. This resulted in a sensitivity of 5/5=100% and a specificity of 4/4=100%. The calculated standard concentrations across all 9 cell lysates are shown (Table 4A). To assess the sensitivity at the cellular level at which FP-MRM analysis could detect the NPM-ALK fusion peptide, a series of dilutions were prepared using an NPM-ALK positive cell lysate (SUD-HL-1) and a negative cell lysate (Mac1) (FIG. 7). The NPM-ALK fusion peptide was detectable above the limit of detection at 5% NPM-ALK positive cells (SUD-HL-1) in a background of NPM-ALK negative cells (Mac1) and above the limit of quantification at 15% NPM-ALK positive cells (SUD-HL-1) in a negative background (Mac1) (FIG. 7A). Fusion peptide MRM results for the dilutions were concordant with both quantitative real-time polymerase chain reaction (FIG. 7B) and western blot analysis (FIGS. 7C and D).

Table 4 shows a comparison of spiked heavy NPM-ALK fusion peptide concentrations to measured concentrations across all standard levels among cell lysates and patient samples. To assess the reproducibility obtained from the NPM-ALK fusion peptide MRM assay, the coefficient of variation (CV) and average percent difference of the spiked isotopically heavy NPM-ALK fusion peptide for each standard level was calculated comparing the measured concentrations to their actual concentrations. (A) A total of nine different cell lysates were evaluated over a one month period. Each lysate was analyzed with its own standard curve generated for internal calibration using the FP-MRM approach with a correlation coefficient>0.99. The percent CV across all nine cell lysate curves was 36.5% at the lowest concentration of 0.439 fmole/µL and 1.6% at the highest concentration of 113 fmole/µL. The average percent difference showed a similar trend of 40.1% at the low concentration and 0.6% at the high concentration. Given the large number of replicates across nine different cell lines, the results are considered representative of the true performance of the assay. (B) A total of twenty three different patient samples were evaluated over a six month period. Of these, eighteen had a standard curve generated using the FP-MRM approach with a correlation coefficient>0.99. The percent CV across all eighteen patient standard curves was 38.1% at the lowest concentration of 0.439 fmole/µL and 2.3% at the highest concentration of 113 fmole/µL. The average percent difference showed a similar trend of 11.9% at the low concentration and 0.1% at the high concentration. Given the large number of replicates across eighteen different clinical patient samples analyzed over several months, it was concluded that the assay was stable and exhibited acceptable between-run variability.

TABLE 4

Reproducibility of standard results across cell lines and patient samples

A

Spiked Heavy NPM-ALK fmole/µL

| Cell Line | Std 1 0.439 | Std 2 0.879 | Std 3 1.76 | Std 4 3.52 | Std 5 7.03 | Std 6 14.1 | Std 7 28.1 | Std 8 56.3 | Std 9 113 |
|---|---|---|---|---|---|---|---|---|---|
| | Calculated concentration (fmole/µL) of cyclized Heavy NPM-ALK + 3 (659.403) in cell lysates | | | | | | | | |
| SUD-HL-1 | 0.457 | 0.530 | 0.937 | 2.46 | 8.59 | 12.9 | 23.4 | 63.7 | 111 |
| Del | 0.256 | 0.711 | 1.36 | 2.93 | 6.33 | 11.6 | 27.8 | 58.2 | 113 |
| Karpas-299 | 0.132 | 1.22 | 2.02 | 3.76 | 7.16 | 18.2 | 28.3 | 49.3 | 116 |
| SUP-M2 | 1.39 | 0.804 | 1.94 | 5.03 | 8.54 | 17.8 | 31.0 | 53.3 | 150 |
| SR786 | 0.350 | 0.493 | 0.704 | 4.15 | 4.96 | 12.3 | 25.5 | 62.7 | 111 |
| HH | 0.209 | 0.509 | 1.23 | 3.30 | 6.51 | 12.3 | 24.7 | 61.0 | 112 |
| Mac-1 | 0.453 | 0.414 | 1.26 | 3.95 | 7.67 | 12.6 | 28.8 | 59.6 | 111 |
| Mac-2A | 0.288 | 0.440 | 1.74 | 3.78 | 8.14 | 15.1 | 27.5 | 54.1 | 114 |
| Jurkat | 0.355 | 0.711 | 1.19 | 3.09 | 8.66 | 14.0 | 26.8 | 58.7 | 112 |
| Avg fmole/µL | 0.292 | 0.648 | 1.38 | 3.61 | 7.40 | 14.1 | 27.1 | 57.8 | 112 |
| sd | 0.107 | 0.252 | 0.444 | 0.759 | 1.27 | 2.45 | 2.30 | 4.74 | 1.8 |

TABLE 4-continued

Reproducibility of standard results across cell lines and patient samples

| % CV | 36.5 | 39.0 | 32.2 | 21.1 | 17.2 | 17.4 | 8.5 | 8.2 | 1.6 |
|---|---|---|---|---|---|---|---|---|---|
| Avg % Difference | 40.1 | 30.3 | 24.5 | 2.4 | 5.1 | 0.0 | 3.7 | 2.7 | 0.6 |
| n = | 7 | 9 | 9 | 9 | 9 | 9 | 9 | 9 | 8 |

B

| | Spiked Heavy NPM-ALK fmole/μL | | | | | | | | |
|---|---|---|---|---|---|---|---|---|---|
| | Std 1 | Std 2 | Std 3 | Std 4 | Std 5 | Std 6 | Std 7 | Std 8 | Std 9 |
| | 0.439 | 0.879 | 1.76 | 3.52 | 7.03 | 14.1 | 28.1 | 56.3 | 113 |
| Patient ID | Calculated concentration (fmole/μL) of cyclized Heavy NPM-ALK + 3 (659.403) in patient samples | | | | | | | | |
| 1 | 0.624 | 0.849 | 2.45 | 4.74 | 6.96 | 16.6 | ~~39.4~~ | 61.2 | 110 |
| 2 | 0.611 | 1.05 | 1.58 | 4.24 | 7.38 | 16.0 | 30.8 | ~~70.4~~ | 112 |
| 3 | 0.461 | 0.408 | 1.88 | 2.23 | 7.06 | 14.5 | 29.0 | 55.8 | ~~89~~ |
| 4 | ~~0.116~~ | 0.678 | 1.56 | 2.08 | 7.70 | 14.2 | 24.4 | 50.3 | 117 |
| 6 | 0.352 | 0.478 | 0.696 | 3.25 | 6.73 | 12.1 | 22.3 | 51.5 | 117 |
| 7 | ~~0.306~~ | ~~0.570~~ | 1.76 | 3.22 | 6.81 | 13.6 | 31.7 | 50.0 | 115 |
| 8 | ~~0.315~~ | 0.736 | 0.660 | 3.34 | 7.29 | 16.8 | 32.5 | 56.5 | 111 |
| 13 | 0.520 | 0.417 | 1.81 | 3.12 | 5.72 | 14.6 | 25.0 | 58.5 | 113 |
| 14 | ~~0.000~~ | 0.708 | 1.24 | 2.12 | 5.42 | 11.0 | 29.3 | 47.8 | 117 |
| 15 | 0.293 | 0.713 | 1.88 | ~~0.000~~ | 6.92 | 12.2 | 31.4 | 55.9 | 113 |
| 16 | 0.319 | 1.95 | 0.935 | 3.31 | 6.52 | 12.7 | 26.0 | 63.7 | 110 |
| 17 | 0.777 | 1.21 | 1.53 | 4.30 | 7.38 | 15.3 | 29.3 | 61.7 | 110 |
| 18 | 0.332 | 0.727 | 1.98 | 4.02 | 7.47 | 15.6 | 30.5 | 58.2 | 111 |
| 19 | 0.604 | 1.01 | 1.51 | 3.73 | 7.03 | 15.8 | 29.9 | 56.4 | 112 |
| 20 | 0.250 | 0.847 | 1.80 | 4.04 | 9.79 | 15.7 | 27.6 | 61.5 | 110 |
| 21 | 0.792 | 0.944 | 2.64 | 3.84 | 6.37 | 16.8 | 30.1 | 53.4 | 114 |
| 22 | ~~0.364~~ | ~~1.086~~ | 1.50 | 3.45 | 7.96 | 15.5 | 27.8 | 52.8 | 115 |
| 23 | ~~0.170~~ | 1.20 | 1.60 | 2.56 | 9.53 | 15.4 | 25.9 | 50.6 | 116 |
| Avg fmole/μL | 0.494 | 0.871 | 1.61 | 3.39 | 7.22 | 14.7 | 28.4 | 55.6 | 113 |
| sd | 0.188 | 0.379 | 0.515 | 0.79 | 1.09 | 1.74 | 2.87 | 4.75 | 2.65 |
| % CV | 38.1 | 43.5 | 32.0 | 23.3 | 15.1 | 11.8 | 10.1 | 8.5 | 2.3 |
| Avg % Difference | 11.9 | 0.9 | 8.8 | 3.8 | 2.7 | 4.1 | 1.2 | 1.2 | 0.1 |
| n = | 12 | 16 | 18 | 17 | 18 | 18 | 17 | 17 | 17 |

Results ~~lined~~ out have been removed from the calculation for the following reasons; Value is below the limit of detection, a sample processing error or instrument malfunction occurred.

Example V

Figure 8:
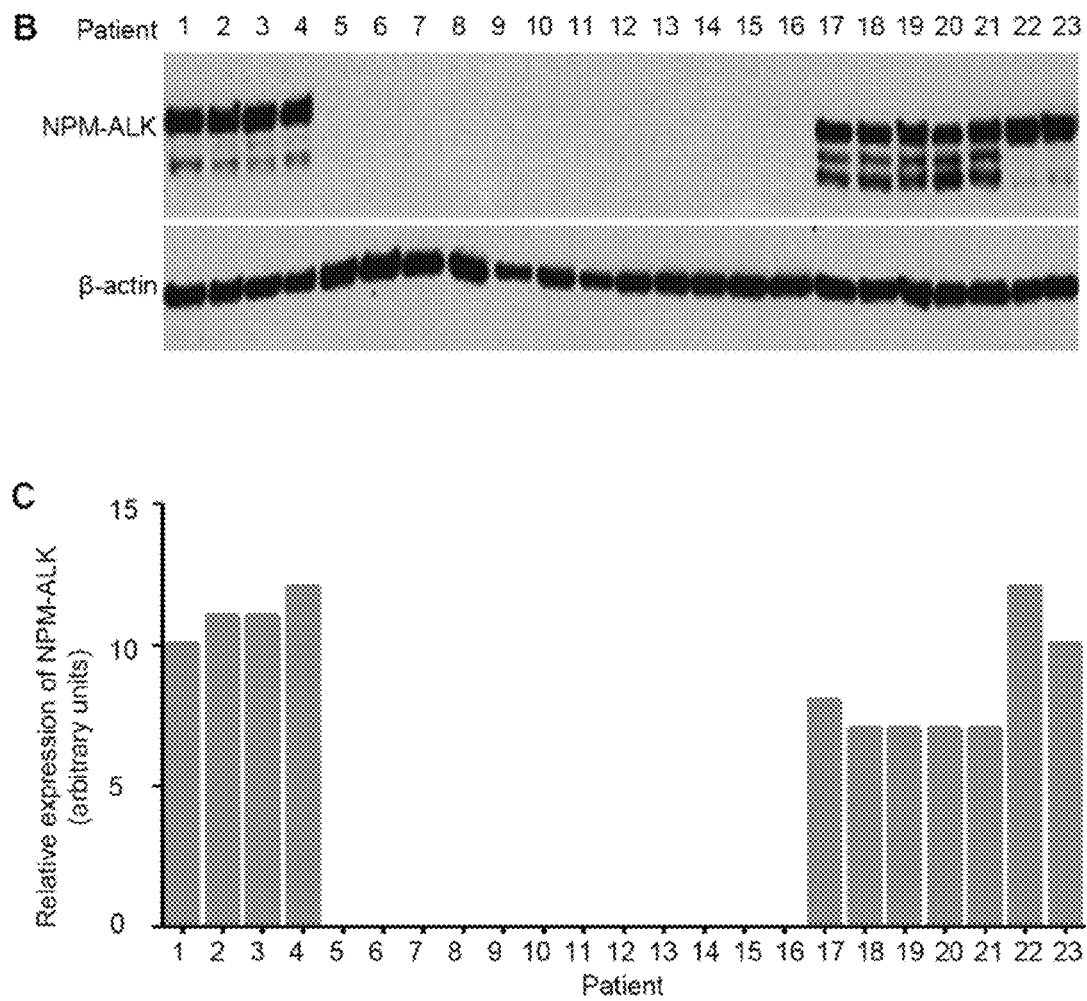
FIG. 8 shows FP-MRM quantitation of NPM-ALK fusion peptide from clinical patient samples. Twenty-three patient samples were analyzed using (A) FP-MRM to ascertain the presence of NPM-ALK fusion peptide. Clinical patient samples had previously been identified as being NPM-ALK positive ALCLs (11) or negative (12). Asterisks indicate patients evaluated against a single 50 fmole/µL heavy and double heavy internal standard and analyzed in triplicate. (B) NPM-ALK expression by western blot analysis is also shown. Four micrograms of protein were run for western blot analysis to detect and quantify NPM-ALK. (C) Quantitation of the western blot results for NPM-ALK expression are shown. The expression level of NPM-ALK was normalized to the expression levels of β-actin for each patient sample.

This example describes the quantitation of NPM-ALK fusion peptide expression by FP-MRM in patient samples. To assess the utility of the NPM-ALK fusion peptide MRM approach in routine clinical patient samples, a cohort of twenty-three patient samples by FP-MRM for NPM-ALK status on lysates obtained from benign and NPM-ALK positive ALCL lymph node biopsy specimens was blindly interrogated (Table 5). A representative standard curve in NPM-ALK positive patient sample #18 demonstrates linearity from 0.439 to 113 fmole/μL (220 to 56,500 fmole/mg lysate) (FIG. 5E). Across patient samples, LOD ranged from 0.439 to 1.76 fmole/μL (220 to 880 fmole/mg lysate), and LOQ ranged from 0.439 to 3.52 fmole/μL (220 to 1760 fmole/mg lysate) (FIG. 8A). FP-MRM analysis correctly determined the NPM-ALK peptide status in all 23 patient samples (FIG. 8A). Because of limited sample, 5 of the 23 patient samples were evaluated against a single 50 fmole/μL heavy and double heavy internal standard and analyzed in triplicate by LC-MRM. Eleven patient samples were NPM-ALK positive and 12 were negative. These results were perfectly concordant with those obtained by western blot analysis (FIGS. 8B and C) and consistent with the original histopathologic diagnoses. Thus, the FP-MRM approach yielded a sensitivity of 11/11=100% and a specificity of 12/12=100%. The calculated standard concentrations across patient samples are shown in Table 4B.

TABLE 5

Clinical data of patient samples

| Patient ID | Diagnosis | Age | Gender | Molecular Data | Classical Cytogenetics/FISH | Immunophenotypic data | Site of involvement |
|---|---|---|---|---|---|---|---|
| 1 | ALCL, ALK-positive | 3 | M | Monoclonal T-cell receptor (gamma) gene rearrangement | Classical cytogenetics t(2; 5) positive, /FISH; ALK-rearrangement positive | CD45+, CD20−, CD2−, CD3−, CD4+, CD5+, CD7−, CD8−, CD30+, Perforin+, ALK+ | Cervical lymph node |
| 2 | ALCL, ALK-positive | 11 | M | ND | FISH - ALK rearrangement positive | CD45−, CD20−, CD79a−, CD2−, CD3+, CD4+, CD5+, CD7−, CD8−, CD30+, ALK+ | Subcutaneous tissue |

TABLE 5-continued

Clinical data of patient samples

| Patient ID | Diagnosis | Age | Gender | Molecular Data | Classical Cytogenetics/FISH | Immunophenotypic data | Site of involvement |
|---|---|---|---|---|---|---|---|
| 3 | ALCL, ALK-positive | 12 | F | Monoclonal T-cell receptor (gamma) gene rearrangement | Classical cytogenetics t(2; 5) positive, /FISH; ALK-rearrangement positive | CD45−, CD45RO+, CD20−, CD2−, CD3−, CD4+, CD5−, CD7−, CD8−, CD30+, ALK+ | Cervical lymph node |
| 4 | ALCL, ALK-positive | 73 | M | Monoclonal T-cell receptor gene rearrangement | ND | CD45−, CD20−, CD2−, CD3−, CD43+, CD4+, CD5+, CD7−, CD8−, CD15−, CD30+, ALK+ | Supraclavicular lymph node |
| 5 | DLBCL | 59 | M | ND | ND | CD45+, CD20+, CD3−, CD10+ | Cervical lymph node |
| 6 | FL | 55 | M | ND | ND | CD45+, CD20+, CD3−, CD10+, BCL2+, BCL6+ | Cervical lymph node |
| 7 | DLBCL | 60 | F | ND | BCL6/IgH+, BCL2/IgH−, cmyc/IgH− | CD45+, CD20+, CD3−, CD10−, BCL2−, BCL6−, MIB1 (55%) | Supraclavicular lymph node |
| 8 | SMZL | 57 | F | Monoclonal IgH receptor gene rearrangement | ND | CD45+, CD20+, CD45RO−, CD3−, CD10−, BCL2+ | Spleen |
| 9 | SMZL | 70 | M | Monoclonal IgH receptor gene rearrangement | ND | CD45+, CD20+, CD3−, CD10−, BCL2+, BCL6− | Spleen |
| 10 | FL | 10 | M | ND | FISH - BCL2 rearrangement positive | CD45+, CD20+, CD3−, CD10+, BCL2+, BCL6+ | Mediastinal mass |
| 11 | T-ALL | 13 | | Monoclonal T-cell receptor gene rearrangement | Classical cytogenetics: Hyperdiploidy, t(1; 7)(p32; q34) | CD45+, CD19−, TdT+, CD3+, CD1a+, CD7−, CD5−, CD4−, CD8− | Mediastinal mass |
| 12 | CLL/SLL | 65 | M | Monoclonal IgH receptor gene rearrangement | ND | CD45+, CD19+, FMC7−, CD3−, CD5+, CD10−, CD23+, Cyclin D1− | Inguinal lymph node |
| 13 | Reactive follicular Hyperplasia | 15 | F | ND | ND | ND | Tonsil |
| 14 | Reactive follicular Hyperplasia | 10 | M | ND | ND | ND | Tonsil |
| 15 | Reactive follicular Hyperplasia | 13 | F | ND | ND | CD45+ (95%), CD19+ (45%), CD3 (40%), Ig (41%), Ig (19%) | Tonsil |
| 16 | Reactive lymphoid Hyperplasia | 45 | M | ND | ND | ND | Inguinal lymph node |
| 17 | ALCL, ALK-positive | 38 | F | ND | ND | CD45+, CD20−, CD2−, CD3−, CD4+, CD5+, CD7−, CD8−, CD30+, ALK+ | Soft tissue, back |
| 18 | ALCL, ALK-positive | 22 | M | Monoclonal T-cell receptor gene rearrangement | ND | CD45−, CD20−, CD2−, CD3−, CD4+, CD5+, CD7−, CD8−, CD30+, ALK+ | Axillary lymph node |
| 19 | ALCL, ALK-positive | 6 | F | ND | FISH - ALK rearrangement positive | CD45+, CD20−, CD2−, CD3−, CD4+, CD5+, CD7−, CD8−, CD30+, ALK+ | Subcutaneous tissue |
| 20 | ALCL, ALK-positive | 14 | M | Monoclonal T-cell receptor gene rearrangement | Classical cytogenetics t(2; 5) positive, /FISH; ALK-rearrangement positive | CD45−, CD20−, CD2−, CD3−, CD4+, CD5+, CD7−, CD8−, CD30+, ALK+ | Cervical lymph node |
| 21 | ALCL, ALK-positive | 21 | M | Monoclonal T-cell receptor gene rearrangement | FISH - ALK rearrangement positive | CD45 weak, CD20−, CD2−, CD3−, CD4+, CD5+, CD7−, CD8−, CD30+, ALK+ | Breast mass |
| 22 | ALCL, ALK-positive | 67 | F | Monoclonal T-cell receptor gene rearrangement | FISH - ALK rearrangement positive | CD45+, CD20−, CD2−, CD3−, CD4+, CD5+, CD7−, CD8−, CD30+, ALK+ | Axillary lymph node |
| 23 | ALCL, ALK-positive | 25 | M | Monoclonal T-cell receptor gene rearrangement | FISH - ALK rearrangement positive | CD45−, CD20−, CD2−, CD3−, CD4+, CD5+, CD7−, CD8−, CD30+, ALK+ | Mediastinal mass |

Key
ND = Not done
FL = Follicular lymphoma
DLBCL = Diffuse large B-cell lymphoma
SMZL = Reactive lymphoid hyperplasia
CLL/SLL = Chronic lymphocytic leukemia/Small lymphocytic lymphoma
T-ALL = T-lineage acute lymphoblastic leukemia All publications and patents mentioned in the above specification are herein incorporated by reference. Various modifications and variations of the described method and system of the invention will be apparent to those skilled in the art without departing from the scope and spirit of the invention.

Although the invention has been described in connection with specific preferred embodiments, it should be understood that the invention as claimed should not be unduly limited to such specific embodiments. Indeed, various modifications of the-described modes for carrying out the invention that are obvious to those skilled in the relevant fields are intended to be within the scope of the present invention.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A method for characterizing a biological sample, comprising:
   a) providing:
      a biological sample, wherein said biological sample is a blood sample and/or a tissue sample,
      one or more distinct groups of labeled peptides, wherein each distinct group of labeled peptides is specific for a particular fusion protein to be detected, wherein the labeled peptides within each distinct group have labeled peptides having an amino acid sequence that spans the fusion junction of said particular fusion protein encoded by a fusion of a first nucleic acid to a second nucleic acid,
         wherein said labeled peptides within each distinct group comprise peptides having one isotopically labeled amino acid residue and peptides having two isotopically labeled amino acid residues,
         wherein said amino acid sequence of said labeled peptides within each distinct group is identical with an amino acid sequence of a particular fusion protein peptide fragment generated through digestion of said particular fusion protein with a protease,
      one or more proteases known to generate upon digestion of said one or more fusion proteins to be detected particular fusion protein peptide fragments,
   b) digesting said biological sample with said one or more proteases resulting in generation of biological sample-based peptide fragments,
   c) combining said one or more distinct groups of labeled peptides with said generated biological sample-based peptide fragments,
   d) purifying said labeled peptides combined with said generated biological sample-based peptide fragments,
   e) conducting a multiple reaction monitoring mass-spectrometry (MRM-MS) analysis of said purified biological sample-based peptide fragments combined with said labeled peptides, and
   f) analyzing the results of said MRM-MS analysis, wherein said analyzing comprises detecting the presence or absence of a biological sample-based fusion protein peptide fragment having an amino acid sequence identical with the amino acid sequence for one of the distinct groups of labeled peptides specific for a particular fusion protein,
   wherein detected co-elution of
      i) a biological sample-based fusion protein peptide fragment having an amino acid sequence identical with the amino acid sequence for one of the distinct groups of labeled peptides specific for a particular fusion protein, and
      ii) said amino acid sequence for one of the distinct groups of labeled peptides specific for a particular fusion protein,
   indicates the presence of said particular fusion protein within said biological sample.

2. The method of claim 1, wherein said levels of fusion protein within said biological sample are approximately 0.4 fmole μL (222 fmoles/mg lysate) or higher.

3. The method of claim 1, wherein said MRM-MS is conducted with a triple quadrupole mass spectrometer.

4. The method of claim 1, wherein said analyzing further comprises quantifying the amount of expression of said detected fusion proteins within said biological sample.

5. The method of claim 1, wherein said one or more proteases is selected from the group consisting of trypsin, chymotrypsin, Arg-C, V8-DE, and Lys-C;
   wherein if one of said proteases is trypsin, then said amino acid sequences resulting from digestion with said protease are selected from the group consisting of:
   CGSGPVHISGQHLVVYR (SEQ ID NO: 1);
   ESNELNNLGHPDNK (SEQ ID NO: 6);
   TIDDLEVYR (SEQ ID NO: 3);
   NVGESVAAALSPLVYR (SEQ ID NO: 8);
   SDFVYCQVCCEPFHK (SEQ ID NO: 10);
   YIMSNSGDYEILYLYR (SEQ ID NO: 16);
   V8-DE, KNSQVYRRKHQE (SEQ ID NO: 17); and
   SEQDLIR (SEQ ID NO: 18);
   wherein if one of said proteases is chymotrypsin, then said amino acid sequences resulting from digestion with said protease are selected from the group consisting of:
   TINKEEAL (SEQ ID NO: 2);
   HGDAEAL (SEQ ID NO: 3);
   GAPQAPVGDVAL (SEQ ID NO: 12);
   GQQSSGQIQL (SEQ ID NO: 20);
   SPQNSIRHNL (SEQ ID NO: 21);
   GQQSEKPY (SEQ ID NO: 22); and
   GQQIAIAPNGAL(SEQ ID NO: 24);
   wherein if one of said protease is Arg-C, then said amino acid sequences resulting from digestion with said protease are selected from the group consisting of:
   GGMGKILKDLSSEDTR (SEQ ID NO: 23); and
   VDFKDSVSLR (SEQ ID NO: 13);
   wherein if said protease is V8-DE, then said amino acid sequences resulting from digestion with said protease are selected from the group consisting of:
   QGPSGASGPAGPRGD (SEQ ID NO: 25);
   SRSVDGVSE (SEQ ID NO: 4);
   LSSCITQGKAIE (SEQ ID NO: 14);
   PTPGKGPKVYRRKHQE (SEQ ID NO: 15);
   FKQTYSNE (SEQ ID NO: 9);
   QIMPKKPAE (SEQ ID NO: 19); and
   QIMPKKPAE (SEQ ID NO: 19);
   wherein said protease is Lys-C, and wherein said amino acid sequences resulting from digestion with said protease are selected from the group consisting of:
   Lys-C, ESRSVDGVSESK (SEQ ID NO: 5); and
   ITVDGPREPRNRTEK (SEQ ID NO: 11).

* * * * *